US009255283B2

(12) United States Patent
Curtiss, III et al.

(10) Patent No.: US 9,255,283 B2
(45) Date of Patent: Feb. 9, 2016

(54) COMPOSITIONS AND METHODS FOR BACTERIAL LYSIS AND NEUTRAL LIPID PRODUCTION

(75) Inventors: Roy Curtiss, III, Paradise Valley, AZ (US); Xinyao Liu, San Diego, CA (US)

(73) Assignee: The Arizona Board of Regents for and on behalf of Arizona State University, Tempe, AZ (US)

( * ) Notice: Subject to any disclaimer, the term of this patent is extended or adjusted under 35 U.S.C. 154(b) by 0 days.

(21) Appl. No.: 13/805,733

(22) PCT Filed: Jul. 1, 2011

(86) PCT No.: PCT/US2011/042821
§ 371 (c)(1),
(2), (4) Date: Apr. 15, 2013

(87) PCT Pub. No.: WO2012/003460
PCT Pub. Date: Jan. 5, 2012

(65) Prior Publication Data
US 2013/0196394 A1    Aug. 1, 2013

Related U.S. Application Data

(60) Provisional application No. 61/361,116, filed on Jul. 2, 2010.

(51) Int. Cl.
C12P 7/64        (2006.01)
C07K 14/195      (2006.01)
C12N 9/18        (2006.01)
C12N 9/20        (2006.01)
C12N 9/36        (2006.01)

(52) U.S. Cl.
CPC .............. *C12P 7/6463* (2013.01); *C07K 14/195* (2013.01); *C12N 9/18* (2013.01); *C12N 9/20* (2013.01); *C12N 9/2462* (2013.01)

(58) Field of Classification Search
CPC ............................... C12P 7/649; C12P 7/6409
USPC ................................................ 435/134, 257.2
See application file for complete search history.

(56) References Cited

U.S. PATENT DOCUMENTS

| 4,190,495 A | 2/1980 | Curtiss, III |
| 4,888,170 A | 12/1989 | Curtiss, III |
| 4,968,619 A | 11/1990 | Curtiss, III |
| 5,294,441 A | 3/1994 | Curtiss, III |
| 5,387,744 A | 2/1995 | Curtiss, III et al. |
| 5,389,368 A | 2/1995 | Curtiss, III |
| 5,424,065 A | 6/1995 | Curtiss, III et al. |
| 5,468,485 A | 11/1995 | Curtiss, III |
| 5,654,184 A | 8/1997 | Curtiss, III et al. |
| 5,656,488 A | 8/1997 | Curtiss, III et al. |
| 5,672,345 A | 9/1997 | Curtiss, III |
| 5,679,880 A | 10/1997 | Curtiss, III et al. |
| 5,686,079 A | 11/1997 | Curtiss, III et al. |
| 5,840,483 A | 11/1998 | Curtiss, III |
| 5,855,879 A | 1/1999 | Curtiss, III |
| 5,855,880 A | 1/1999 | Curtiss, III et al. |
| 5,888,799 A | 3/1999 | Curtiss, III |
| 6,024,961 A | 2/2000 | Curtiss, III et al. |
| 6,383,496 B1 | 5/2002 | Curtiss, III et al. |
| 6,610,529 B1 | 8/2003 | Curtiss, III et al. |
| 6,780,405 B1 | 8/2004 | Curtiss, III et al. |
| 6,872,547 B1 | 3/2005 | Curtiss, III |
| 7,083,794 B2 | 8/2006 | Curtiss, III et al. |
| 7,195,757 B2 | 3/2007 | Curtiss, III et al. |
| 7,341,860 B2 | 3/2008 | Curtiss, III et al. |
| 7,871,604 B1 | 1/2011 | Curtiss, III et al. |
| 8,133,493 B2 | 3/2012 | Curtiss, III |
| 2003/0031683 A1 | 2/2003 | Curtiss, III et al. |
| 2004/0054165 A1 | 3/2004 | Rainey et al. |
| 2004/0101531 A1 | 5/2004 | Curtiss, III et al. |
| 2004/0137003 A1 | 7/2004 | Curtiss, III |
| 2005/0106176 A1 | 5/2005 | Curtis, III et al. |
| 2006/0140975 A1 | 6/2006 | Curtiss et al. |
| 2006/0233829 A1 | 10/2006 | Curtiss, III |
| 2009/0061493 A1 | 3/2009 | Trimbur et al. |
| 2009/0203070 A1 | 8/2009 | Devroe et al. |
| 2009/0305942 A1 | 12/2009 | Day et al. |
| 2011/0250659 A1 | 10/2011 | Roberts et al. |
| 2012/0237987 A1 | 9/2012 | Curtiss, III et al. |

FOREIGN PATENT DOCUMENTS

| WO | 2008/113041 A2 | 9/2008 |
| WO | 2008/130437 A2 | 10/2008 |
| WO | 2009/155357 A1 | 12/2009 |
| WO | 2011/059745 A1 | 5/2011 |
| WO | 2012/003460 A2 | 1/2012 |

OTHER PUBLICATIONS

Jeffries, 2005; Ethanol Fermentation on the move. Nature Biotechnology 23(1): 40-41.*
Liu et al. 2009; Nickel-inducible lysis system in *Synechocystis sp.* PCC 6803. PNAS 106(51): 21550-21554.*
Liu et al. 2011; Fatty acid production in genetically modified cyantobacteria. PNAS 108(17): 6899-6904.*
Kucho, et al., CO2-Responsive Transcriptional Regulation of CAH1 Encoding Carbonic Anhydrase is Mediated by Enhancer and Silencer Regions in *Chlamydomonas reinhardtii*. Plant Physiol. Dec. 1999, vol. 121, No. 4, pp. 1329-1337, abstract 1329, right col, para 2.
Altschul et al., "Gapped Blast and PSI-Blast: a new generation of protein database search programs", Nucleic Acids Research, 1997, pp. 3389-3402, vol. 25, No. 17.
Bertani, "Studies on Lysogenesis, I. The Mode of Phage Liberation by Lysogenic *Escherichia Coli* ", Journal of Bacteriology, 1951, pp. 293-300, vol. 62, No. 3.
Chen, "Permeability issues in whole-cell bioprocesses and cellular membrane engineering", Appl Microbiol Biotechnol, 2007, pp. 730-738, vol. 74.

(Continued)

*Primary Examiner* — Karen Cochrane Carlson
(74) *Attorney, Agent, or Firm* — Rebecca C. Riley-Vargas; Polsinelli PC

(57) ABSTRACT

The present invention is directed to a cyanobacterium that produces neutral lipids or alkanes. Such neutral lipids or alkanes may be used for biofuel production.

18 Claims, 28 Drawing Sheets

(56) References Cited

OTHER PUBLICATIONS

Higuchi et al., "A general method of in vitro preparation and specific mutagenesis of DNA fragments: study of protein and DNA interactions", Nucleic Acids Research, 1988, pp. 7351-7367, vol. 16, No. 15.

International Search Report and Written Opinion from related International Application No. PCT/US2010/54494, dated Feb. 11, 2011; 14 pgs.

International Search Report and Written Opinion from related International Application No. PCT/US2011/42821, dated Feb. 1, 2012; 11 pgs.

Kang et al., "Transduction-Mediated Transfer of Unmarked Deletion and Point Mutations through Use of Counterselectable Suicide Vectors", Journal of Bacteriology, 2002, pp. 307-312, vol. 184, No. 1.

Karlin et al., "Applications and statistics for multiple high-scoring segments in molecular sequences", Proc. Natl. Acad. Sci. USA, 1993, pp. 5873-5877, vol. 90.

Lieman-Hurwitz et al., "A cyanobacterial AbrB-like protein affects the apparent photosynthetic affinity for CO2 by modulating low-CO2-induced gene expression", Environmental Microbiology, 2009, pp. 927-936, vol. 11, No. 4.

Office Action from related U.S. Appl. No. 13/459,774, dated Jan. 28, 2015; 10 pgs.

Pugsley et al., "Colicin E2 Production and Release by *Escherichia coli* K12 and Other Enterobacteriaceae", Journal of General Microbiology, 1985, pp. 2673-2686, vol. 131.

Roth et al., "Bacterial Viability and Antibiotic Susceptibility Testing with SYTOX Green Nucleic Acid Stain", Applied and Environmental Microbiology, 1997, pp. 2421-2431, vol. 63, No. 6.

Shortle et al., "Gap misrepair mutagenesis: Efficient site-directed induction of transition, transversion, and frameshift mutations in vitro", Proc. Natl. Acad. Sci. USA, 1982, pp. 1588-1592, vol. 79.

Vallette et al., "Construction of mutant and chimeric genes using the polymerase chain reaction", Nucleic Acids Research, 1989, pp. 723-733, vol. 17, No. 2.

Wu et al., "Versatile microbial surface-display for environmental remediation and biofuels production", Trends in Microbiology, 2008, pp. 181-188, vol. 16, No. 4.

\* cited by examiner

COMPOSITIONS AND METHODS FOR BACTERIAL LYSIS AND NEUTRAL LIPID PRODUCTION

REFERENCE TO SEQUENCE LISTING

A paper copy of the sequence listing and a computer readable form of the same sequence listing are appended below and herein incorporated by reference. The information recorded in computer readable form is identical to the written sequence listing, according to 37 C.F.R. 1.821 (f).

FIELD OF THE INVENTION

The invention encompasses a cyanobacterium that produces neutral lipids or alkanes. Such neutral lipids or alkanes may be used for biofuel production.

BACKGROUND OF THE INVENTION

The search for alternative fuel sources continues to be a high priority. Photosynthetic bacteria, such as the cyanobacteria, potentially provide a source of lipids that are relatively easy to harvest. The lipids may then be converted to biofuel. To increase the efficiency of the system, however, it would be beneficial to use a bacterial strain that produced lipids that are readily converted to a biofuel, such as neutral lipids. Hence, there is a need in the art for a photosynthesizing bacterium that produces high concentrations of neutral lipids or hydrocarbons like alkanes.

REFERENCE TO COLOR FIGURES

The application file contains at least one photograph executed in color. Copies of this patent application publication with color photographs will be provided by the Office upon request and payment of the necessary fee.

DETAILED DESCRIPTION OF THE INVENTION

Figure 1:
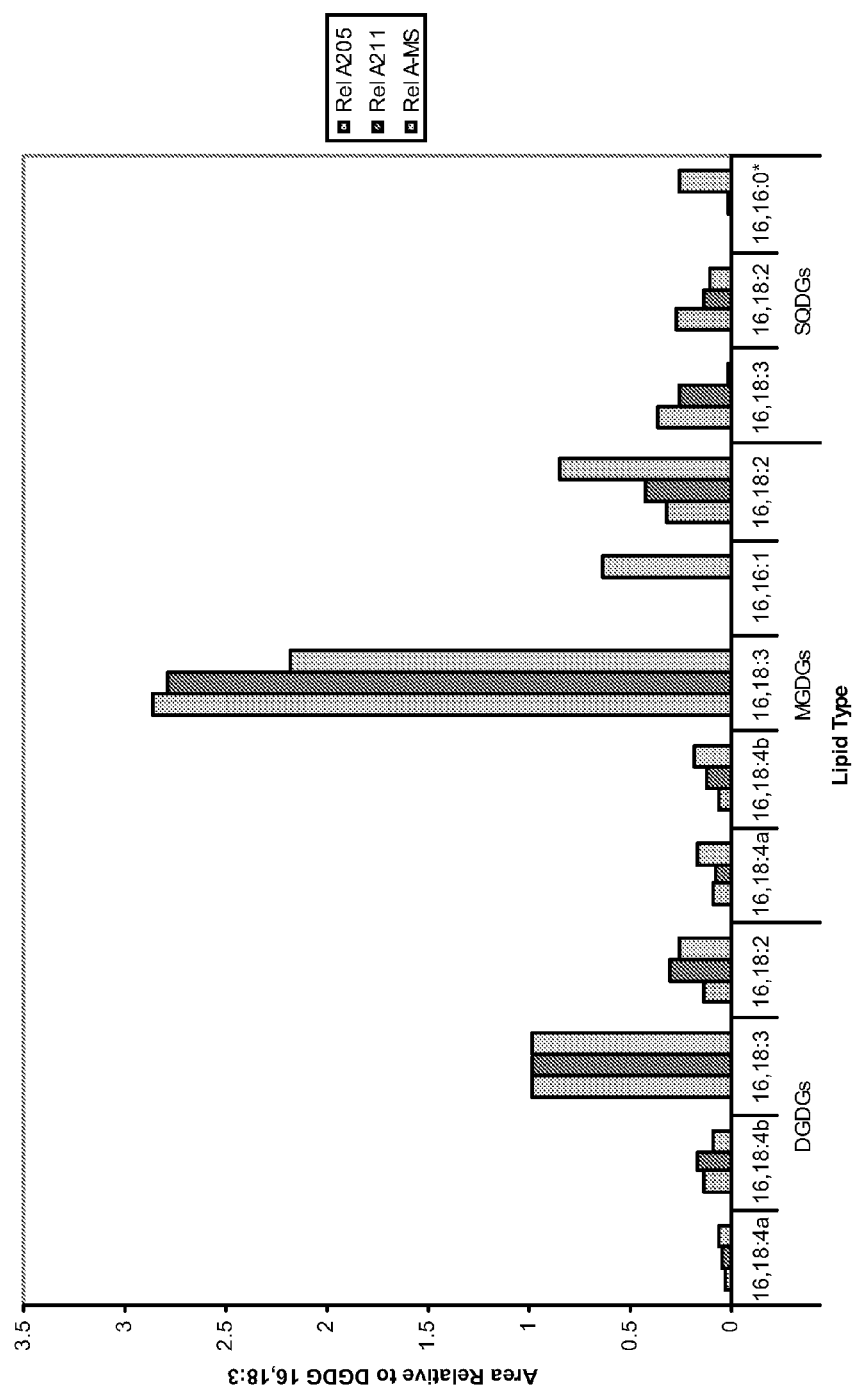
FIG. 1 depicts the native lipid comparisons in wild-type *Synechocystis*. Monogalactosyldiacylglycerol (MGDG), digalactosyldiacylglycerol (DGDG), and sulphoquinovosyldiacylglycerol (SQDG), were compared using UV absorbance (Rel A205, at the wavelength of 205 nm; and Rel A211, at the wavelength of 211 nm) and MS (mass spectrum) relative area (Rel A-MS). The subtypes of lipids are shown on the X axis, for example, '16, 18:3' means a DGDG molecule with a saturated C16 fatty acid and a C18 fatty acid with 3 double bonds. All the other lipid amounts were shown as relative amounts compared to the absorbance peak or MS area of 16, 18:3.

The present invention provides a cyanobacterium capable of producing neutral lipids. In certain embodiments, the cyanobacterium additionally comprises the regulated expression of a nucleic acid encoding a protein capable of hydrolyzing the lipid membranes, allowing at least one enzyme to degrade the cellular lipid membranes and the peptidoglycan layer of a bacterial cell wall. Such degradation allows for ready harvesting of the neutral lipids, which may be useful for developing biofuels.

I. Neutral Lipids

One aspect of the present invention encompasses a cyanobacterium capable of producing neutral lipids. As used herein, the phrase "neutral lipids" refers to non-polar lipids. Non-limiting examples of neutral lipids may include triacylglycerol (TAG), steryl esters (SEs), wax ester (WE), fatty acyl methyl ester (FAME), fatty acyl ethyl ester (FAEE) and poly (3-hydroxybutyrate) (PHB). Generally speaking, neutral lipids lack charged groups and are therefore unable to integrate into bilayer membranes in substantial amounts. They serve as intracellular storage molecules for sterols, free fatty acids, and diacylglycerols (DAGs).

In some embodiments, a cyanobacterium capable of producing neutral lipids comprises a nucleic acid sequence encoding a neutral lipid synthase. Generally speaking, a neutral lipid synthase is a synthase that aids in the expression of one or more neutral lipids. Neutral lipid synthases may be found in other prokaryotic or eukaryotic species. For instance, the first wax ester synthase (WS) as well as acyl-CoA:diacylglycerol acyltransferase (DGAT) (WS/DGAT) enzyme was identified in *A. baylyi* sp. ADP1, and its gene (atfA) was cloned into *E. coli* by Kalscheuer and Steinbüchel (2003 J. Biol. Chem. 287: 8075-82). This bacterium possesses only a single WS/DGAT enzyme. Numerous atfA homologs, however, can be found among the available genome databases of actinomycetes, especially in those of *Mycobacterium, Rhodococcus* and *Streptomycetes*. In particular, *Mycobacteria* possess a large number of conserved proteins with high homologies to the *A. baylyi* sp. ADP1 AtfA. By way of non-limiting example, 15 atfA homologous genes were identified and characterized in *M. tuberculosis* H37Rv. Genes with high homologies to the *Acinetobacter* sp. ADP1 atfA were also identified in the genome databases of several Gram-negative strains, including marine bacteria like *Hahella chejuensis*, psychrophilic strains like *Psychrobacter* sp. and *Polaromonas* sp. and even in *Bradyrhizobium japonicum*. Hence, suitable neutral lipid synthases may be derived, for example, from *Acinebacter baylyi, Rhodococcus opacus, Rhodococcus ruber, Ralstonia eutropha, Streptomyces coelicolor, Norcardia* sp., or *Mycobacterium smegmatis*. In one embodiment, the TAG synthase encoded by the atfA gene from *Acinebacter baylyi* is a non-limiting example of a neutral lipid synthase. Alternatively, suitable neutral lipid synthases may be synthesized in vitro based on a wild-type sequence derived from a prokaryotic or eukaryotic organism. Methods of introducing a nucleic acid sequence encoding a neutral lipid synthase to a cyanobacterium are known in the art and detailed in the examples.

In other embodiments, a cyanobacterium capable of producing neutral lipids comprises a nucleic acid sequence encoding a lipid body protein. Typically a lipid body protein aids in storing the neutral lipids within the cyanobacterium. A non-limiting example of a lipid body protein is a PHA inclusion protein such as PhaC, PhaZ, PhaR, and phasins such as PhaP1. Additionally, proteins associated with TAG inclusions have been referred to as granule-associated proteins (GAP) and exhibit apparent molecular masses ranging from to 31 kDa. By way of non-limiting example, in *R. opacus* PD630, these were GAP15, GAP17, GAP20, GAP26, and GAP31, with the numeration indicating the apparent molecular weight (Kalscheuer et al. 2001 Arch. Microbiol. 177:20-28.)

The nucleic acid encoding PhaP1 may be cloned from *Ralstonia eutropha*. Methods of introducing a nucleic acid sequence encoding a lipid body protein to a cyanobacterium are known in the art and detailed in the examples.

In certain embodiments, a cyanobacterium of the invention may lack a functional lipase that catalyzes the hydrolysis of a neutral lipid. For instance, a cyanobacterium may lack a functional lipase encoded by a lipA nucleic acid. Methods for modifying a cyanobacterium to lack a functional lipase are known in the art and may include deletion mutations and insertion-deletion mutations. In one embodiment, a cyanobacterium that lacks a functional lipase may comprise a nucleic acid cassette inserted into the coding region of lipA. For instance, the cassette may comprise a nucleic acid sequence encoding a neutral lipid synthase or a nucleic acid sequence encoding a lipid body protein. In certain embodiments, the cassette may comprise $P_{psbAII}$ atfA phaP1.

II. Release of Fatty Acids from Cellular Membranes

Another aspect of the invention encompasses the discovery that the regulated expression of a nucleic acid encoding a protein capable of hydrolyzing the lipid membranes to free fatty acids may be used to disrupt the cells and release intracellular neutral lipids. Hence, in one embodiment, the invention encompasses a cyanobacterium comprising an inducible promoter operably-linked to a nucleic acid encoding a first protein capable of hydrolyzing the lipid membranes of the bacterium and at least one endolysin protein. In another embodiment, the invention encompasses a cyanobacterium comprising a first nucleic acid, wherein the first nucleic acid comprises a first inducible promoter operably-linked to a nucleic acid encoding a first protein capable of hydrolyzing the lipid membranes of the bacterium; and a second nucleic acid, wherein the second nucleic acid comprises a second promoter operably-linked to a nucleic acid encoding at least one endolysin protein.

In certain instances, the invention encompasses a cyanobacterium comprising more than one integrated nucleic acid construct of the invention. For instance, the invention may encompass a cyanobacterium comprising a first inducible promoter operably-linked to a nucleic acid encoding a first protein capable of hydrolyzing the lipid membranes of the bacterium, a second inducible promoter operably-linked to a different nucleic acid encoding a first protein capable of hydrolyzing the lipid membranes of the bacterium, and at least two endolysin proteins. In a further embodiment, the nucleic acid sequences encoding the endolysin proteins may be operably linked to a constitutive promoter.

Methods of making cyanobacterium of the invention are known in the art. Generally speaking, a cyanobacterium is transformed with a nucleic acid construct of the invention. Methods of transformation are well known in the art, and may include electroporation, natural transformation, and calcium chloride mediated transformation. Methods of screening for and verifying chromosomal integration are also known in the art.

In one embodiment, a method of making a cyanobacterium of the invention may comprise first transforming the bacterium with a vector comprising, in part, an antibiotic resistance marker and a negative selection marker. Chromosomal integration may be selected for by selecting for antibiotic resistance. Next, the antibiotic strain is transformed with a similar vector comprising the target genes of interest. Chromosomal integration of the target genes may be selected for by selecting for the absence of the negative marker. For instance, if the negative marker is sacB, then one would select for sucrose resistance. For more details, see Kang et al., J. Bacteriol. (2002) 184(1):307-12, hereby incorporated by reference in its entirety.

(a) Nucleic Acid Constructs

The present invention encompasses a nucleic acid construct that, when introduced into a bacterium, may be used in a method for inducing the degradation of lipid membrane or the peptidoglycan layer of a bacterial cell wall. In one embodiment, the nucleic acid comprises an inducible promoter operably-linked to a nucleic acid sequence encoding a first protein capable of hydrolyzing bacterial lipid membranes into free fatty acids. In another embodiment, the nucleic acid comprises an inducible promoter operably-linked to a nucleic acid sequence encoding a first protein capable of forming a lesion in a bacterial lipid membranes. In yet another embodiment, the nucleic acid comprises a promoter operably-linked to at least one endolysin. In another embodiment, the nucleic acid comprises an inducible promoter operably-linked to both a nucleic acid sequence encoding a first protein and a nucleic acid sequence encoding at least one endolysin. In still another embodiment, the nucleic acid comprises an inducible promoter operably-linked to a nucleic acid sequence encoding a first protein and a second promoter operably-linked to a nucleic acid sequence encoding at least one endolysin. Each component of the above nucleic acid constructs is discussed in more detail below.

Methods of making a nucleic acid construct of the invention are known in the art. Additional information may be found in Sambrook et al., Molecular Cloning: A Laboratory Manual (New York: Cold Spring Harbor Laboratory Press, 1989)

i. Promoters

A nucleic acid construct of the present invention comprises a promoter. In particular, a nucleic acid construct comprises a first inducible promoter. In some embodiments, a nucleic acid also comprises a second promoter. When a nucleic acid comprises a first and a second promoter, the promoters may read in opposite directions, or may read in the same direction.

A. First Inducible Promoter

In certain embodiments, a nucleic acid of the invention encompasses a first inducible promoter. Non-limiting examples of inducible promoters may include, but are not limited to, those induced by expression of an exogenous protein (e.g., T7 RNA polymerase, SP6 RNA polymerase), by the presence of a small molecule (e.g., IPTG, galactose, tetracycline, steroid hormone, abscisic acid), by absence of small molecules (e.g., $CO_2$, iron, nitrogen), by metals or metal ions (e.g., copper, zinc, cadmium, nickel), and by environmental factors (e.g., heat, cold, stress), and by growth phase. In each of the above embodiments, the inducible promoter is preferably tightly regulated such that in the absence of induction, substantially no transcription is initiated through the promoter. Additionally, induction of the promoter of interest should not typically alter transcription through other promoters. Also, generally speaking, the compound or condition that induces an inducible promoter should not be naturally present in the organism or environment where expression is sought.

In one embodiment, the inducible promoter is induced by limitation of $CO_2$ supply to the cyanobacteria culture. By way of non-limiting example, the inducible promoter may be variant sequences of the promoter sequence of Synechocystis PCC6803 that are up-regulated under the $CO_2$-limitation conditions, such as the cmp genes, ntp genes, ndh genes, sbt genes, chp genes, and rbc genes.

In one embodiment, the inducible promoter is induced by iron starvation or by entering the stationary growth phase. By way of non-limiting example, the inducible promoter may be variant sequences of the promoter sequence of Synechocystis PCC6803 isiA gene. In some embodiments, the inducible promoter may be variance sequences of the promoter sequence of cyanobacterial genes that are up-regulated under Fe-starvation conditions such as isiA, or when the culture enters the stationary growth phase, such as isiA, phrA, sigC, sigB, and sigH genes.

In one embodiment, the inducible promoter is induced by a metal or metal ion. By way of non-limiting example, the inducible promoter may be induced by copper, zinc, cadmium, mercury, nickel, gold, silver, cobalt, and bismuth or ions thereof. In one embodiment, the inducible promoter is induced by nickel or a nickel ion. In an exemplary embodiment, the inducible promoter is induced by a nickel ion, such as $Ni^{2+}$. In another exemplary embodiment, the inducible promoter is the nickel inducible promoter from *Synechocystis* PCC6803. In another embodiment, the inducible promoter may be induced by copper or a copper ion. In yet another embodiment, the inducible promoter may be induced by zinc or a zinc ion. In still another embodiment, the inducible promoter may be induced by cadmium or a cadmium ion. In yet still another embodiment, the inducible promoter may be induced by mercury or a mercury ion. In an alternative embodiment, the inducible promoter may be induced by gold or a gold ion. In another alternative embodiment, the inducible promoter may be induced by silver or a silver ion. In yet another alternative embodiment, the inducible promoter may be induced by cobalt or a cobalt ion. In still another alternative embodiment, the inducible promoter may be induced by bismuth or a bismuth ion.

In some embodiments, the promoter is induced by exposing a cell comprising the inducible promoter to a metal or metal ion. The cell may be exposed to the metal or metal ion by adding the metal to the bacterial growth media. In certain embodiments, the metal or metal ion added to the bacterial growth media may be efficiently recovered from the media. In other embodiments, the metal or metal ion remaining in the media after recovery does not substantially impede downstream processing of the media or of the bacterial gene products.

In one embodiment, the nucleic acid comprises a metal or metal ion inducible promoter operably-linked to a nucleic acid sequence encoding a first protein capable of hydrolyzing a bacterial lipid membranes. In another embodiment, the nucleic acid comprises a metal or metal ion inducible promoter operably-linked to both a nucleic acid sequence encoding a first protein and a nucleic acid sequence encoding at least one endolysin. In yet another embodiment, the nucleic acid comprises a metal or metal ion inducible promoter operably-linked to at least one endolysin. In still another embodiment, the nucleic acid comprises a metal or metal ion inducible promoter operably-linked to a nucleic acid sequence encoding a first protein and a second promoter operably-linked to a nucleic acid sequence encoding at least one endolysin.

B. Second Promoter

Certain nucleic acid constructs of the invention may comprise a second promoter. The second promoter may be an inducible promoter, or may be a constitutive promoter. If the second promoter is an inducible promoter, it may or may not be induced by the same compound or condition that induces the first inducible promoter. In one embodiment, the same compound or condition induces both the first and the second inducible promoters. In another embodiment, the first inducible promoter is induced by a different compound or condition than the second inducible promoter. Non-limiting examples of inducible promoters that may be used are detailed in section I(a)(i) above.

Constitutive promoters that may comprise the second promoter are known in the art. Non-limiting examples of constitutive promoters may include constitutive promoters from Gram negative bacteria or a Gram negative bacteriophage. For instance, promoters from highly expressed Gram negative gene products may be used, such as the promoter for Lpp, OmpA, rRNA, and ribosomal proteins. Alternatively, regulatable promoters may be used in a strain that lacks the regulatory protein for that promoter. For instance $P_{lac}$, $P_{tac}$, and $P_{trc}$ may be used as constitutive promoters in strains that lack LacI. Similarly, P22 $P_R$ and $P_L$ may be used in strains that lack the P22 C2 repressor protein, and λ $P_R$ and $P_L$ may be used in strains that lack the λ C1 repressor protein. In one embodiment, the constitutive promoter is from a bacteriophage. In another embodiment, the constitutive promoter is from a *Salmonella* bacteriophage. In yet another embodiment, the constitutive promoter is from a cyanophage. In some embodiments, the constitutive promoter is a *Synechocystis* promoter. For instance, the constitutive promoter may be the $P_{psbAII}$ promoter or its variant sequences, the $P_{rbc}$ promoter or its variant sequences, the $P_{cpc}$ promoter or its variant sequences, and the $P_{rnpB}$ promoter or its variant sequences.

In one embodiment, a nucleic acid of the invention comprises a metal or metal ion inducible promoter operably-linked to a nucleic acid sequence encoding a first protein and a second constitutive promoter operably-linked to a nucleic acid sequence encoding at least one endolysin. In another embodiment, a nucleic acid of the invention comprises a metal or metal ion inducible promoter operably-linked to a nucleic acid sequence encoding a first protein and a second inducible promoter operably-linked to a nucleic acid sequence encoding at least one endolysin.

ii. First Protein

A nucleic acid construct of the invention also comprises a sequence encoding at least one first protein. Generally speaking, a first protein is a protein capable of degrading the lipid membranes into free fatty acid and release intracellular neutral lipids. For instance, the first protein may be a lipolytic enzyme that is able to hydrolyze acylglycerols. In one embodiment, the first protein may be a lipolytic enzyme that hydrolyzes diacylglycerols, including MGDG (monogalactosyl diacylglycerol), DGDG (digalactosyl diacylglycerol), PG (phosphatidylglycerol), and SQDG (sulfoquinovosyl diacylglycerol). In another embodiment, the first protein may be a lipase that hydrolyzes triacylglycerols. In yet another embodiment, the first protein may be a lipolytic enzyme that hydrolyzes monoacylglycerols. In still yet another embodiment, the first protein may be a lipolytic enzyme from a bacterium, e.g., *Staphylococcus hyicus*. In a further embodiment, the first protein may be a lipolytic enzyme from a fungus, e.g., *Fusarium oxysporum*. In one embodiment, the first protein may be a lipolytic enzyme from an animal, e.g, guinea pig.

In other embodiments, a first protein is a protein capable of hydrolyzing the lipid membranes that provides the endolysin access to the peptidoglycan layer of the cell wall. In these embodiments, the first protein may be a bacteriophage protein. For instance, the first protein may be a bacteriophage holin protein. In one embodiment, the first protein is a holin from a bacteriophage that infects gram-negative bacteria. In another embodiment, the first protein is a holin from a bacteriophage that infects gram-positive bacteria. In certain embodiments, the first protein is a holin from a cyanophage. In one embodiment, the first protein is a holin from a bacteriophage that infects *Synechocystis*. In another embodiment, the first protein may be from a bacteriophage that infects *Salmonella*. In still another embodiment, the first protein may be from a P22 phage. For example, the first protein may be gene 13 of the P22 phage. In yet another embodiment, the first protein may be from a λ phage. For example, the first protein may be encoded by gene S of the λ phage. In still another embodiment, the first protein may be from an *E. coli* phage. For instance, the first protein may be encoded by gene E of *E.*

*coli* phage PhiX174. In certain embodiments, a nucleic acid of the invention may comprise at least two holins. In one embodiment, a nucleic acid may comprise a holin from P22 and a holin from λ phage. For instance, the nucleic acid may comprise gene 13 and gene S.

Additionally, a first protein may be a holin described above with at least one, or a combination of one or more, nucleic acid deletions, substitutions, additions, or insertions which result in an alteration in the corresponding amino acid sequence of the encoded holin protein, such as a homolog, ortholog, mimic or degenerative variant. For instance, a first protein may be a holin described above encoded by a nucleic acid with codons optimized for use in a particular bacterial strain, such as *Synechocystis*. Such a holin may be generated using recombinant techniques such as site-directed mutagenesis (Smith Annu. Rev. Genet. 19. 423 (1985)), e.g., using nucleic acid amplification techniques such as PCR (Zhao et al. Methods Enzymol. 217, 218 (1993)) to introduce deletions, insertions and point mutations. Other methods for deletion mutagenesis involve, for example, the use of either BAL 31 nuclease, which progressively shortens a double-stranded DNA fragment from both the 5' and 3' ends, or exonuclease III, which digests the target DNA from the 3' end (see, e.g., Henikoff Gene 28, 351 (1984)). The extent of digestion in both cases is controlled by incubation time or the temperature of the reaction or both. Point mutations can be introduced by treatment with mutagens, such as sodium bisulfite (Botstein et al. Science 229, 1193 (1985)). Other exemplary methods for introducing point mutations involve enzymatic incorporation of nucleotide analogs or misincorporation of normal nucleotides or alpha-thionucleotide by DNA polymerases (Shortle et al. Proc. Natl. Acad. Sci. USA 79, 1588 (1982)). PCR-based mutagenesis methods (or other mutagenesis methods based on nucleic acid amplification techniques), are generally preferred as they are simple and more rapid than classical techniques (Higuchi et al. Nucleic Acids Res. 16, 7351 (1988); Vallette et al. Nucleic Acids Res. 17, 723 (1989)).

In addition to having a substantially similar biological function, a homolog, ortholog, mimic or degenerative variant of a holin suitable for use in the invention will also typically share substantial sequence similarity to a holin protein. In addition, suitable homologs, ortholog, mimic or degenerative variants preferably share at least 30% sequence homology with a holin protein, more preferably, 50%, and even more preferably, are greater than about 75% homologous in sequence to a holin protein. Alternatively, peptide mimics of a holin could be used that retain critical molecular recognition elements, although peptide bonds, side chain structures, chiral centers and other features of the parental active protein sequence may be replaced by chemical entities that are not native to the holin protein yet, nevertheless, confer activity.

In determining whether a polypeptide is substantially homologous to a holin polypeptide, sequence similarity may be determined by conventional algorithms, which typically allow introduction of a small number of gaps in order to achieve the best fit. In particular, "percent homology" of two polypeptides or two nucleic acid sequences is determined using the algorithm of Karlin and Altschul [Proc. Natl. Acad. Sci. USA 87, 2264 (1993)]. Such an algorithm is incorporated into the NBLAST and XBLAST programs of Altschul, et al. (J. Mol. Biol. 215, 403 (1990)). BLAST nucleotide searches may be performed with the NBLAST program to obtain nucleotide sequences homologous to a nucleic acid molecule of the invention. Equally, BLAST protein searches may be performed with the XBLAST program to obtain amino acid sequences that are homologous to a polypeptide of the invention. To obtain gapped alignments for comparison purposes, Gapped BLAST is utilized as described in Altschul, et al. (Nucleic Acids Res. 25, 3389 (1997)). When utilizing BLAST and Gapped BLAST programs, the default parameters of the respective programs (e.g., XBLAST and NBLAST) are employed. See http://www.ncbi.nlm.nih.gov for more details.

In one embodiment, a nucleic acid of the invention comprises a metal or metal ion inducible promoter operably-linked to a nucleic acid sequence encoding a P22 phage holin. In another embodiment, the nucleic acid comprises a metal or metal ion inducible promoter operably-linked to both a nucleic acid sequence encoding a P22 phage holin and a nucleic acid sequence encoding at least one endolysin. In yet another embodiment, the nucleic acid comprises a metal or metal ion inducible promoter operably-linked to a nucleic acid sequence encoding a P22 phage holin and a second promoter operably-linked to a nucleic acid sequence encoding at least one endolysin.

iii. Endolysin

In some embodiments, a nucleic acid of the invention comprises at least one endolysin. In other embodiments, a nucleic acid of the invention comprises at least two endolysins. In yet another embodiment, a nucleic acid of the invention comprises at least three endolysins. In still another embodiment, a nucleic acid of the invention may comprise at least four endolysins. As used herein, "endolysin" refers to a protein capable of degrading the peptidoglycan layer of a bacterial cell wall. Generally speaking, the term endolysin encompasses proteins selected from the group consisting of lysozyme or muramidase, glucosaminidase, transglycosylase, amidase, and endopeptidase. Exemplary endolysins do not affect the cell until after the first protein creates lesions in the lipid membranes. Stated another way, the accumulation of endolysins in the cytosol of a bacterium will typically not substantially impair the growth rate of the bacterium. In another exemplary embodiment, the endolysin has a high enzymatic turnover rate. In yet another exemplary embodiment, the endolysin is from a gram positive bacteria. Because the cell walls of gram positive bacteria typically have a thicker peptidoglycan layer, an endolysin from a gram positive bacteria might be expected to have a higher enzymatic turnover rate.

In one embodiment, at least one endolysin is from a bacteriophage. In certain embodiments, suitable endolysins may be from phages detailed in section I(b) above in reference to the first protein. In another embodiment, at least one endolysin is from a *Salmonella* bacteriophage. In yet another embodiment, at least one endolysin is from a P22 phage. In still yet another embodiment, at least one endolysin is from a λ phage. In an alternative embodiment, at least one endolysin is gp19 from a P22 phage. In another alternative, a nucleic acid of the invention comprises gp19 and gp15 from a P22 phage. In some embodiments, at least one endolysin is R from a λ phage. In other embodiments, a nucleic acid of the invention comprises R and Rz from a λ phage. In certain embodiments, a nucleic acid of the invention comprises gp19, gp15, R, and Rz.

Additionally, an endolysin may be a protein described above with at least one, or a combination of one or more, nucleic acid deletions, substitutions, additions, or insertions which result in an alteration in the corresponding amino acid sequence of the encoded endolysin protein, such as a homolog, ortholog, mimic or degenerative variant. Such an endolysin may be generated using recombinant techniques such as those described in section I(b) above in reference to a first protein. In addition to having a substantially similar biological function, a homolog, ortholog, mimic or degenerative variant of an endolysin suitable for use in the invention will also typically share substantial sequence similarity to an endolysin protein. In addition, suitable homologs, ortholog, mimic or degenerative variants preferably share at least 30% sequence homology with an endolysin protein, more preferably, 50%, and even more preferably, are greater than about 75% homologous in sequence to an endolysin protein. Alternatively, peptide mimics of an endolysin could be used that retain critical molecular recognition elements, although peptide bonds, side chain structures, chiral centers and other features of the parental active protein sequence may be replaced by chemical entities that are not native to the endolysin protein yet, nevertheless, confer activity. Percent homology may be calculated as described in section I(b) above.

iv. Additional Components

In certain embodiments, nucleic acids of the invention may further comprise additional components, such as a marker, a spacer domain, and a flanking sequence.

A. Markers

In one embodiment, a nucleic acid of the invention comprises at least one marker. Generally speaking, a marker encodes a product that the host cell cannot make, such that the cell acquires resistance to a specific compound, is able to survive under specific conditions, or is otherwise differentiable from cells that do not carry the marker. Markers may be positive or negative markers. In some embodiments, a nucleic acid of the invention may comprise both a positive marker and a negative marker. In certain embodiments, the marker may code for an antibiotic resistance factor. Suitable examples of antibiotic resistance markers may include, but are not limited to, those coding for proteins that impart resistance to kanamycin, spectromycin, neomycin, geneticin (G418), ampicillin, tetracycline, and chloramphenicol. Additionally, the sacB gene may be used as a negative marker. The sacB gene is lethal in many bacteria when they are grown on sucrose media. Additionally, fluorescent proteins may be used as visually identifiable markers. Generally speaking, markers may be present during construction of the strains, but are typically removed from the final constructs. Proteins can also be marked by adding a sequence such as FLAG, HA, His tag, that can be recognized by a monoclonal antibody using immunological methods. In some embodiments, a marker may be a unique indentifier of a genetically modified cyanobacterium.

B. Spacer Domain

Additionally, a nucleic acid of the invention may comprise a Shine-Dalgarno sequence, or a ribosome binding site (RBS). Generally speaking, a RBS is the nucleic acid sequence in the mRNA that binds to a 16s rRNA in the ribosome to initiate translation. For Gram negative bacteria, the RBS is generally AGGA. The RBS may be located about 8 to about 11 bp 3' of the start codon of the first structural gene. One skilled in the art will realize that the RBS sequence or its distance to the start codon may be altered to increase or decrease translation efficiency.

C. Flanking Sequence

Nucleic acid constructs of the invention may also comprise flanking sequences. The phrase "flanking sequence" as used herein, refers to a nucleic acid sequence homologous to a chromosomal sequence. A construct comprising a flanking sequence on either side of a construct (i.e. a left flanking sequence and a right flanking sequence) may homologously recombine with the homologous chromosome, thereby integrating the construct between the flanking sequences into the chromosome. Generally speaking, flanking sequences may be of variable length. In an exemplary embodiment, the flanking sequences may be between about 300 and about 500 bp. In another exemplary embodiment, the left flanking sequence and the right flanking sequence are substantially the same length. For more details, see the Examples.

v. Plasmids

A nucleic acid construct of the invention may comprise a plasmid suitable for use in a bacterium. Such a plasmid may contain multiple cloning sites for ease in manipulating nucleic acid sequences. Numerous suitable plasmids are known in the art.

III. Overproduction of Acyl-CoA

The critical substrate for neutral lipids synthesis is acyl-CoA. The *A. baylyi* sp. ADP1 WS/DGAT is able to transfer acyl-CoA to diacylglycerol to produce TAG, and also able to transfer acyl-CoA to methanol or ethanol to produce FAME or FAEE respectively. However, cyanobacteria do not possess the acyl-CoA synthesis pathway, and thus do not have a significant amount of acyl-CoA in the cell for the production of neutral lipids. In contrast, cyanobacteria normally use acyl carrier proteins (ACP) as the intermediate acyl carriers for fatty acid synthesis and metabolism.

To overproduce acyl-CoA in cyanobacteria, free fatty acids have to be released from acyl-ACP by thioesterases. In this invention, thioesterases are from bacteria and plants, e.g, tesA gene and its variants, and fatB genes and their variants. Then the free fatty acids have to be ligated to Coenzyme A by acyl-CoA ligases (ACL). In this invention, ACL genes are from bacteria (e.g., fadD from *E. coli*), and from yeast (e.g., faa2 from *Saccharomyces cerevisiae*). Acyl-CoA is the right substrate to produce an acyltransferase (e.g., WS/DGAT) to trans-esterify with an alcohol for a neutral lipid such as triacylglycerols (TAG here after), fatty acly methyl esters (FAME hereafter), or fatty acyl ethyl esters (FAEE hereafter).

A bacterium of the invention may comprise an alteration that enables the synthesis of at least one acyl-ACP thioesterase (hereinafter TE). Methods of altering a bacterium to synthesize a TE are known in the art. For instance, a bacterium may be altered to express a nucleic acid encoding a TE. Such a nucleic acid may be operably linked to a regulated promoter or a constitutive promoter. In certain embodiments, a bacterium may synthesize one, two, three, four or five TEs. A nucleic acid encoding a TE may be chromosomally integrated, or may be expressed on an extrachromosomal vector. Suitable vectors are known in the art. Similarly, methods of chromosomally inserting a nucleic acid are known in the art. For additional details, see the Examples.

In some embodiments, a bacterium may synthesize a TE that is restricted to the cytosol of the bacterium. For instance, in one embodiment, a bacterium of the invention may synthesize a variant of TesA that is restricted to the cytosol of the bacterium. By way of non-limiting example, a bacterium may synthesize *TesA. The expression of a nucleic acid encoding TesA may be regulated or constitutive. For instance, the nucleic acid may be operably linked to an inducible promoter. Non-limiting examples of a suitable inducible promoter include $P_{nrsB}$, $P_{cmpA}$, $P_{isiA}$, $P_{sigE}$, $P_{lrtA}$, or $P_{sbD2}$. $P_{nrsB}$ is nickely inducible, $P_{cmpA}$ is inducible by $CO_2$, $P_{isiA}$ is inducible under low Fe conditions, $P_{sigE}$ is inducible during the stationary phase, $P_{lrtA}$ is dark inducible, and $P_{sbD2}$ may be induced by strong light.

Alternatively, the nucleic acid encoding a TE may be operably linked to a constitutive promoter, such as $P_{psbA2}$, $P_{cpc}$, $P_{rbc}$, $P_{petB}$, $P_{psaAB}$, $P_{hspA}$, or $P_{sigA}$.

Other TE enzymes are known in the art and may be used in the present invention. For instance, a TE from *Cinnamomum camphorum, Umbellularia californica*, or *Cuphea hookeriana* may be used. In another embodiment, a TE outlined in WO 2009/076559 may be used.

The selection of the TE may be determined by the desired chain length of the resulting free fatty acid. For instance, see Example 13 below. In one embodiment, a TE with a preference for shorter free fatty acids may be used. For instance, a TE with a preference for C16, C14, C12, C10 or C8 fatty acids may be used.

A nucleic acid encoding a TE may be modified for high-level expression in a bacterium of the invention. As used herein, "modified" refers to an alteration of a nucleic acid sequence that results in a change in the level of transcription of a nucleic acid sequence, or that results in a change in the level of synthesis of encoded protein. For instance, in one embodiment, modify may refer to altering the start codon of a nucleic acid sequence. Generally speaking, a GTG or TTG start codon, as opposed to an ATG start codon, may decrease translation efficiency ten-fold. In another embodiment, modify may refer to altering the Shine-Dalgarno (SD) sequence of a nucleic acid sequence. The SD sequence is a ribosomal binding site generally located 6-7 nucleotides upstream of the start codon. The SD consensus sequence is AGGAGG, and variations of the consensus sequence may alter translation efficiency. In yet another embodiment, modify may refer to altering the distance between the SD sequence and the start codon. In still another embodiment, modify may refer to altering the −35 sequence for RNA polymerase recognition. In a similar embodiment, modify may refer to altering the −10 sequence for RNA polymerase binding. In an additional embodiment, modify may refer to altering the number of nucleotides between the −35 and −10 sequences. In an alternative embodiment, modify may refer to optimizing the codons of the nucleic acid sequence to alter the level of translation of the mRNA. For instance, non-A rich codons initially after the start codon of a nucleic acid sequence may not maximize translation of the corresponding mRNA. Similarly, the codons of the nucleic acid sequence may be altered so as to mimic the codons from highly synthesized proteins of a particular organism. In a further embodiment, modify may refer to altering the GC content of the nucleic acid sequence to change the level of translation of the corresponding mRNA. In still another embodiment, a nucleic acid may be optimized by altering the nucleic acid such that the ability of the encoded protein to form efficient enzyme complexes is affected.

IV. Methods

Yet another aspect of the invention encompasses a method for degrading the peptidoglycan layer of a bacterial cell wall to aid in the release of neutral lipids from the cyanobacterium. Generally speaking, the method comprises inducing the first promoter in a cyanobacterium of the invention that produces neutral lipids, such that the first protein is expressed. Methods of inducing a promoter are well known in the art. For more details when the promoter is induced by a metal or metal ion, see the Examples. The first protein, by forming lesions in the lipid membranes, allows the endolysin to degrade the peptidoglycan layer of a bacterial cell wall. The endolysin may be operably-linked to the first promoter, or alternatively, the endolysin may be operably-linked to a second promoter, as detailed above.

The second promoter may be an inducible promoter, or a constitutive promoter. In some embodiments, the second promoter is a constitutive promoter. In these embodiments, the endolysin(s) are expressed and accumulate in the cell, but are inactive because they do not have access to the peptidoglycan layer of the cell wall. After the induced expression of the holin(s), the endolysin(s) has access to the peptidoglycan layer of the cell wall, and subsequently, may degrade the peptidoglycan layer of the cell wall.

In other embodiments, the second promoter is an inducible promoter. The inducible promoter may be induced by a different compound or condition than the first promoter. In these embodiments, expression of the endolysin(s) may be induced first, with the subsequent induction of the holin(s) via the first promoter.

In certain embodiments, the peptidoglycan layer of the cell wall is substantially degraded in less than 12 hours, less than 10 hours, less than 8 hours, less than 7 hours, less than 6 hours, less than 5 hours, or less than 4 hours. In one embodiment, the peptidoglycan layer of the cell wall is substantially degraded in less than 6 hours.

After the peptidoglycan layer of a cell wall is degraded, the remaining lipid membranes may be further disrupted to release the neutral lipids of the cell into the media.

DEFINITIONS

The term "cell wall", as used herein, refers to the peptidoglycan layer of the cell wall. Stated another way, "cell wall" as used herein refers to the rigid layer of the cell wall.

The term "operably-linked", as used herein, means that expression of a gene is under the control of a promoter with which it is spatially connected. A promoter may be positioned 5' (upstream) of a gene under its control. The distance between the promoter and a gene may be approximately the same as the distance between that promoter and the gene it controls in the gene from which the promoter is derived. As is known in the art, variation in this distance may be accommodated without loss of promoter function.

The term "promoter", as used herein, may mean a synthetic or naturally-derived molecule which is capable of conferring, activating or enhancing expression of a nucleic acid in a cell. A promoter may comprise one or more specific transcriptional regulatory sequences to further enhance expression and/or to alter the spatial expression and/or temporal expression of same. A promoter may also comprise distal enhancer or repressor elements, which can be located as much as several thousand base pairs from the start site of transcription. In some embodiments, activators may bind to promoters 5' of the −35 RNA polymerase recognition sequence, and repressors may bind 3' to the −10 ribosome binding sequence.

The following examples are included to demonstrate preferred embodiments of the invention. It should be appreciated by those of skill in the art that the techniques disclosed in the examples that follow represent techniques discovered by the inventors to function well in the practice of the invention. Those of skill in the art should, however, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

The following examples illustrate various iterations of the invention.

Example 1

Lipid Content of Synechocystis Sp. PCC 6803

The cyanobacterium Synechocystis sp. PCC 6803 ("Synechocystis" or "6803" hereafter) was selected as the model microorganism to produce biodiesel in tube-like photobioreactors after genetic modification to increase the production of lipids and facilitate lipid recovery. The virtues of *Synechocystis*, such as rapid growth rate, environmental adaptability and ease of genetic modification, make this cyanobacterial strain a promising solar energy collector for future convertible energy production. However, in exploring the feasibility of technical routes for growth in the field bed photobioreactor with production of lipids for ease of conversion to biofuels, it was realized that several challenges would have to be addressed. The first problem was the natural lipid content of *Synechocystis*. According to results of HPLC-MS analyses, the main lipid contents are polar lipids (Wada and Murata 1990) such as glyco-lipids (monogalactosyldiacylglycerol, MGDG and digalactosyldiacylglycerol, DGDG), sulfo-lipids (sulphoquinovosyl-diacylglycerol, SQDG), and phospholipid (PG) as shown in FIG. 1. These polar lipids are the components of membranes (glyco-lipids and sulfo-lipids for the photosynthesis thykaloid membranes and phospholipids for the cell membranes), which would not form lipid drops in a polar solvent within the cells. In addition, the sugar, sulfate or phosphate molecules would cause problems in the downstream refinery processes in the production of biofuels.

The following examples describe the genetic changes engineered into *Synechocystis* to anticipate problems in downstream processing and refining into biofuels. *Synechocystis* was genetically engineered to store these neutral lipids in lipid drops or lipid bodies. Once the lipids are sequestered, their yields can be accumulated; once the lipids are accumulated, they could be easily recoverable. In addition, to facilitate the lipid recovery process, a nickel inducible lysis system for *Synechocystis* was developed. Briefly, as previously reported, we introduced a set of lysis genes from bacteriophages into the *Synechocystis* sp. PCC 6803 genome and placed them downstream of a $Ni^{2+}$ sensing and tightly regulating element, so that expression of the lysis genes would be induced by addition of $Ni^{2+}$. By combining these two systems in *Synechocystis*, neutral lipid production and nickel controllable lysis, a neutral lipid releasing *Synechocystis* recombinant was achieved, which would increase the production efficiency of lipids more readily modifiable into biofuels.

Example 2

Genetic Engineering of *Synechocystis* for TAG Production

Figure 2:
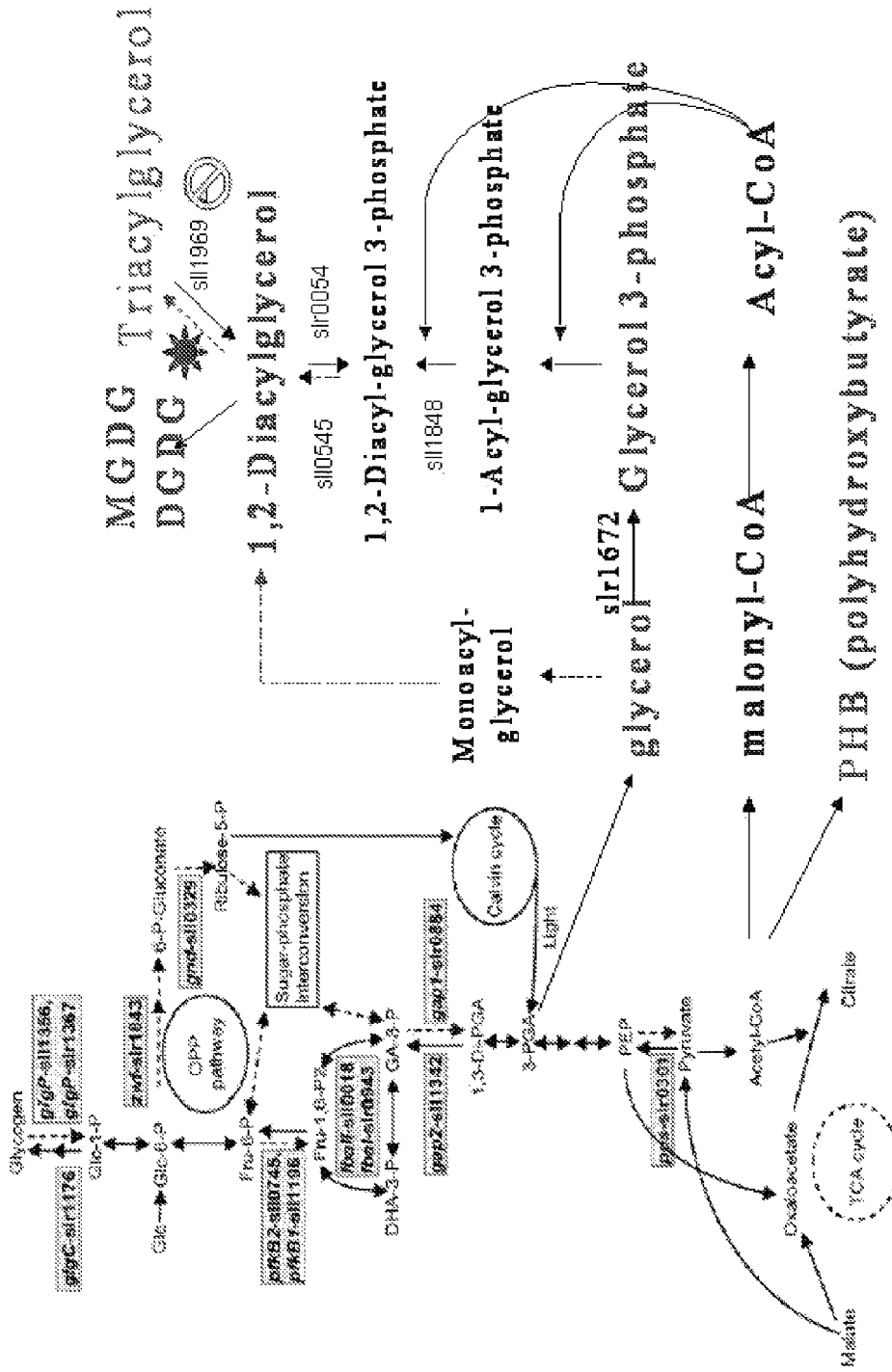
FIG. 2 depicts lipid metabolism in *Synechocystis*. Red suns indicate pathways toward TAG, which are in consideration for over-expression or introduction from other organisms. Yellow stop signs indicate pathways away from TAG, which are in consideration for knocking out (i.e., elimination).

Most lipids in *Synechocystis* are glyco-lipids (DGDG and MGDG) constituting photosynthesis thykaloid membranes (FIG. 1), and there are also some phospho- and sulfo-lipids. All of these lipids are polar membrane lipids. Storage neutral lipids such as in the form of triglycerides are rarely found in *Synechocystis*. As shown in FIG. 2, no triglyceride synthesis gene was identified in the genome of *Synechocystis* sp. PCC 6803. Also, the basic triglyceride signals obtained by HPLC-MS were only low-level noise. In plants and animals, energy is stored in the form of neutral lipids, mainly TAG (Dyer and Mullen 2008). Neutral lipids have a higher energy content than membrane lipids, which is the basis of interest in this form of lipid by energy companies.

Figure 3:
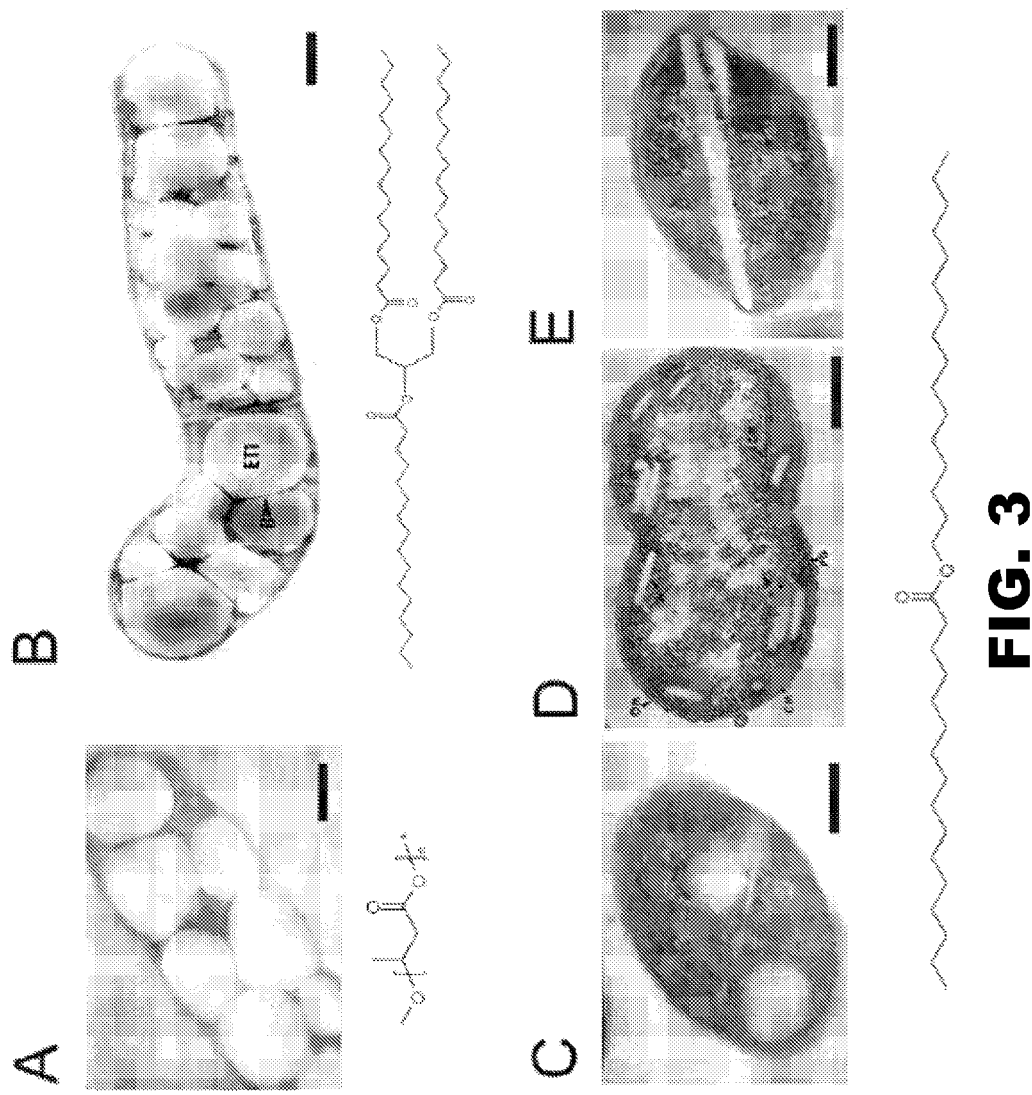
FIG. 3 depicts intracellular lipid inclusions in prokaryotes and general structures of the lipids. (A) Cell of *R. eutropha* H16 accumulating PHB inclusions; (B) cell of *R. opacus* PD630 from late stationary growth phase accumulating large amount of TAG inclusions; (C) cell of *A. calcoaceticus* ADP1 with three spherical WE inclusions; (D) *Acinetobacter* sp. strain HO1-N accumulating small rectangular WE inclusions; (E) *Acinetobacter* sp. strain M1 accumulating large, disclike WE inclusions. Bars, 0.2 µm. Cited from (Walternann and Steinbuchel 2005).
Figure 4:
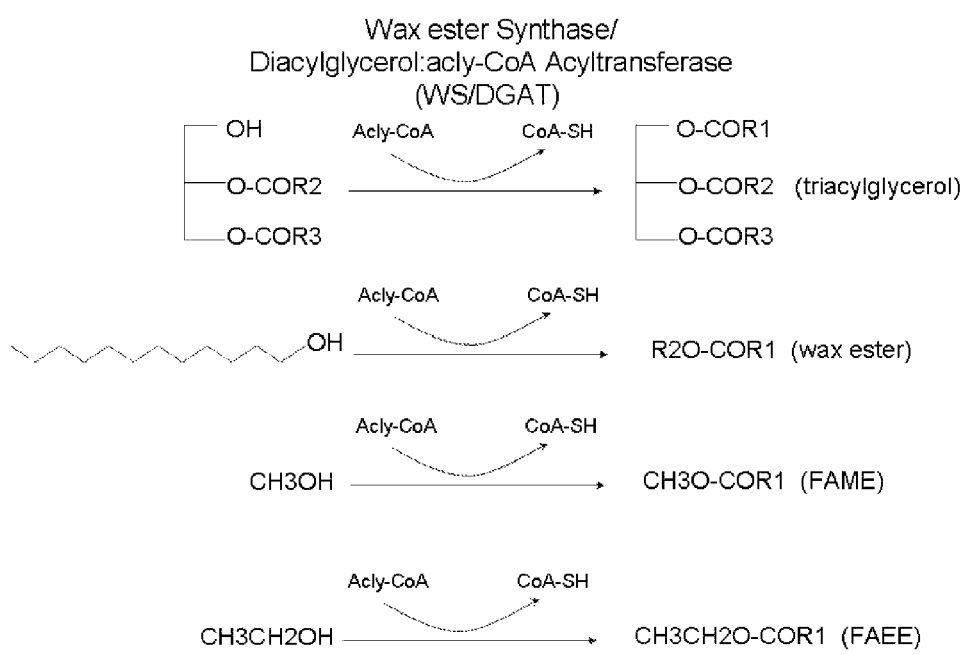
FIG. 4 depicts biosynthetic funtions of the wax ester synthase (WS)/acyl-CoA:diacylglycerol acyltransferase (DGAT) (WS/DGAT) enzyme identified in *A. baylyi* sp. ADP1.

From diverse petroleum polluted soils and water habitats, several groups of prokaryotes that accumulate neutral storage lipid compounds such as poly(3-hydroxybutyrate) PHB, triacylglycerol (TAG) and wax ester (WE) in their lipid bodies have been identified (Alvarez and Steinbuchel 2002; Walternann, Hinz et al. 2005). As shown in FIG. 3, (Walternann and Steinbuchel 2005), bacteria such as *Rhodococcus opacus, Rhodococcus ruber, Ralstonia eutropha, Streptomyces coelicolor, Norcardia* sp., and *Mycobacterium smegmatis*, store neutral lipids as lipid bodies in their cells. As shown in FIG. 4, the final step in WE and TAG biosyntheses in the bacterium *Acinetobacter baylyi* sp. ADP1 is catalyzed by a promiscuous (multifunctional) enzyme, which exhibits both WE synthase (WS) and diacylglycerol (DAG):acly-CoA aclytransferase (DGAT) activities (Kalscheuer and Steinbuchel 2003; Walternann, Stoveken et al. 2007).

Figure 5:
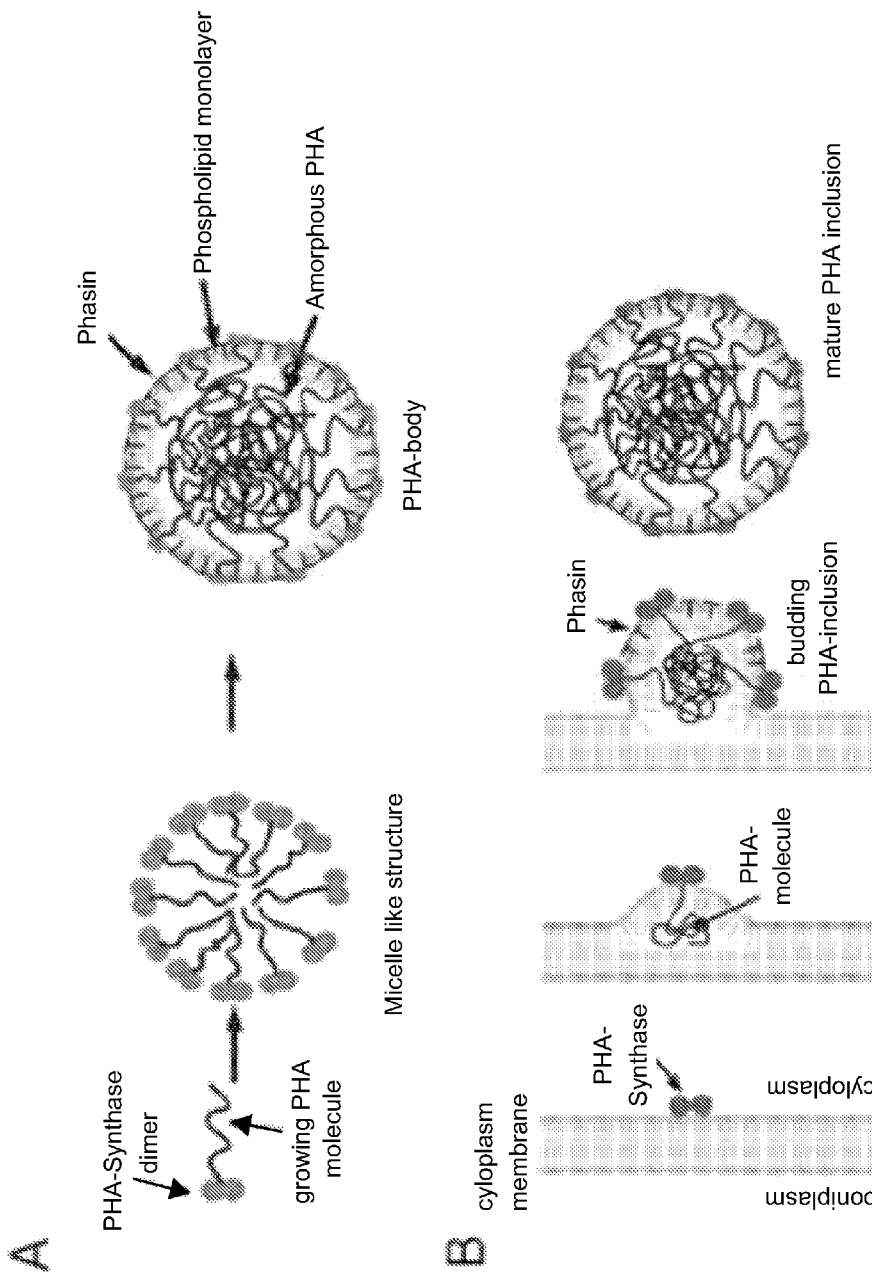
FIG. 5 depicts suggested models for the formation of PHA inclusions in bacteria. (A) The 'micelle' model; (B) the 'budding membrane' model. Cited from (Walternann and Steinbuchel 2005).

The TAG synthase gene (atfA) was cloned from *Acinetobacter baylyi* sp. ADP1, which encodes a promiscuous (multifunctional) enzyme (WS/DGAT) exhibiting both WE synthase (WS) and diacylglycerol (DAG):acly-CoA aclytransferase (DGAT) activities (Kalscheuer and Steinbuchel 2003). It was the first prokaryotic WS/DGAT enzyme, not related to any known acyltransferase enzyme families in eukaryotes. Its acyltransferase activities were successfully expressed in yeast (Kalscheuer, Luftmann et al. 2004) and *E. coli* (Kalscheuer, Stolting et al. 2006). It should be noticed that the substrates for TAGs are DAG and acly-CoA, which are also the substrates for the DGDG, MGDG, SQDG and PG, so the substrates for TAGs should be abundant in *Synechocystis* cells. For the purpose of neutral lipid production, the TAG synthase gene from *A. baylyi* sp. ADP1 was introduced into the *Synechocystis* genome. A gene encoding a prokaryotic lipid body protein, a phasin (PHA inclusion protein) PhaP1, was also introduced into the *Synechocystis* genome. The phaP1 gene was cloned from *Ralstonia eutropha* H16. PhaP1 is able to target and bind to intracellular TAG inclusions in other oil bacteria and provides an anchor to other target proteins (Hanisch, Walternann et al. 2006). As shown in FIG. 5, it was reported that the non-specificity of PhaP1 could be utilized to help the formation of TAG-containing lipid bodies.

Figure 6:
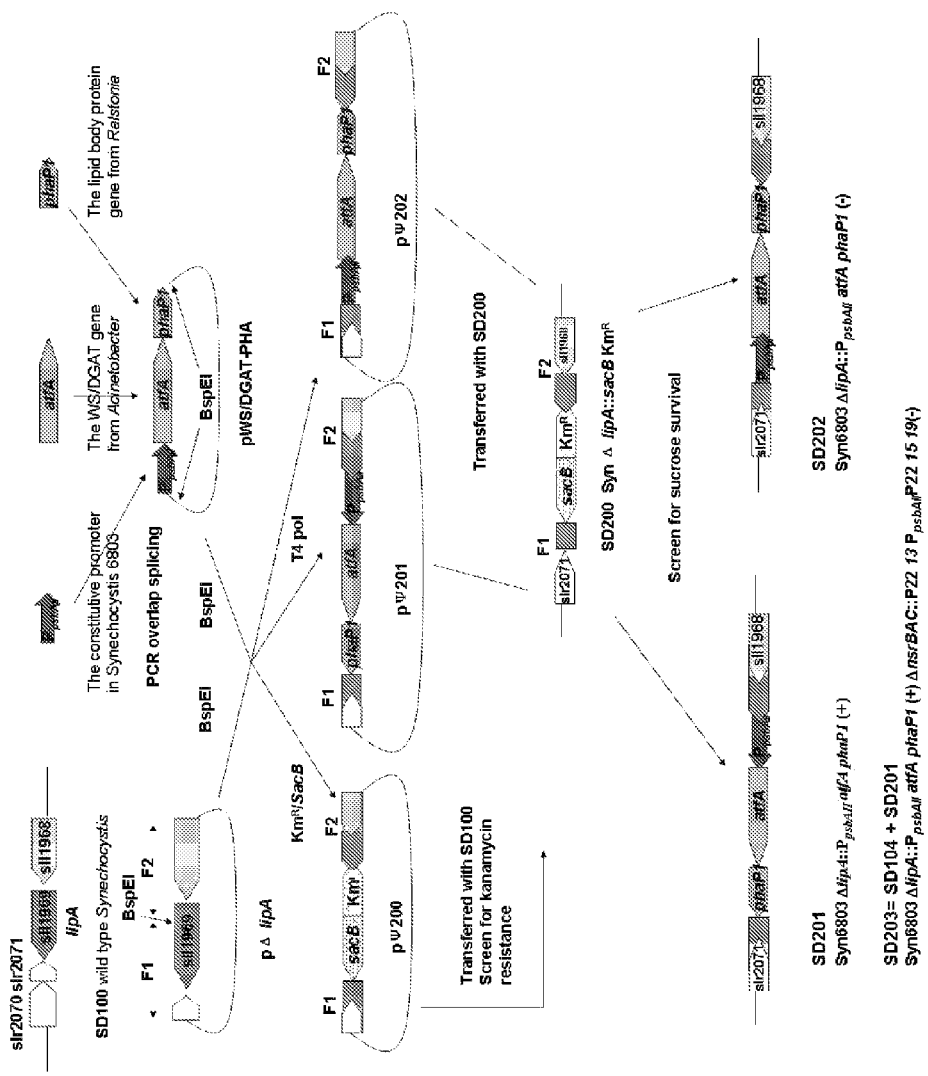
FIG. 6 depicts the construction of triglyceride-producing *Synechocystis* strains SD201, SD202 and SD203. The primers used in the construction can be referred to in Table 9.

In addition, the putative *Synechocystis* lipase gene (lipA, sll1969) was interrupted by inserting the genes for the lipid-producing operon cassette $P_{psbAII}$ atfA phaP1 in the coding region of lipA. The gene encodes an enzyme with acetyltransferase and hydrolase activities, which catalyzes the hydrolysis of TAGs. The construction of the strains SD201 and SD202 containing the genes for the lipid-producing cassette inserted into the coding region of lipA in opposite orientations are shown in FIG. 6 and Table 1. In this regard, the $P_{psbAII}$ promoter is a constitutive and active promoter in *Synechocystis*. The detailed methods of the constructions are described in Example 20.

TABLE 1

The *Synechocystis* strains used or developed for this invention

| SD # | Genotype | Parent plasmid | Description/Derivation |
|---|---|---|---|
| SD100 | *Synechocystis* sp. PCC 6803 wild type | | From Dr. Wim Vermaass' lab, School of Life Science, Arizona State University |

TABLE 1-continued

The *Synechocystis* strains used or developed for this invention

| SD # | Genotype | Parent plasmid | Description/Derivation |
|---|---|---|---|
| SD101 | ΔnrsBA21::$P_{nrsB20}$ 13 19 15 Km$^R$ | SD100 pψ101 | This is a testing strain obtained by transforming SD100 with pψ101 to make sure that the lysis genes from bacteriophage would work in cyanobacteria. |
| SD102 | ΔnrsBAC11::$P_{nrsB21}$ 13 Km$^R$ sacB | SD100 pψ102 | This is an intermediate strain obtained by transforming SD100 with pψ102, with a Km$^r$-sacB cassette, which can be replaced by further insertion. |
| SD104 | ΔnrsBAC11::$P_{nrsB22}$ 13 Inv($P_{psbA223}$ 19 15)-23 | SD102 pψ104 | Nickle inducible lysis strain. Obtained by transforming SD102 with pψ104. The P22 genes 15 and 19 (endolysin) were placed under a constitutive promoter ($P_{psbAll}$) in opposite orientation of the holin gene. |
| SD106 | ΔnrsBAC11::$P_{nrsB24}$ 13 S R Rz | SD102 pψ106 | Nickle inducible lysis strain. Obtained by transforming SD102 with pψ106. Lysis genes S, R, Rz from *E. coli* phage λ were inserted after P22 gene 13. |
| SD107 | ΔnrsBAC11::$P_{nrsB25}$ 13 RBS S R Rz | SD102 pψ107 | Nickle inducible lysis strain. Obtained by transforming SD 102 with pψ107. A RBS sequence (ribosome binding site) was inserted before lysis genes S, R, Rz. |
| SD111 | $P_{isiA26}$::13 19 15 Km$^R$ | SD100 pψ111 | Stationary autolysis strain, stocked. The lysis genes will befully induced at the first 5 days of the stationary growth phase, slightly induced at exponential growth phase ($10^{4-4.5}$ cells/ml), also fully induced at Fe deficiency (Fe <2 μM, 1/10 BG-11 concentration). Note that $P_{isiA}$ is a strong promoter in *E. coli*. The cassette 13 19 15 Km$^R$ was inserted in between $P_{isiA26}$ and isiA, so no mutation in sequence, but the isiA express should be interrupted. |
| SD121 | ΔnrsBAC11::$P_{nrsB27}$ 13 19 15 | SD102 pψ121 | Nickle inducible lysis strain. Nickel controlling P22 lysis cassette strain |
| SD122 | ΔnrsBAC11::$P_{nrsB28}$ S R Rz | SD102 pψ122 | Nickle inducible lysis strain. Nickel controlling lambda lysis cassette strain |
| SD123 | ΔnrsBAC11::$P_{nrsB29}$ 13 TT $P_{psbA223}$ 19 15 | SD102 pψ123 | Nickle inducible lysis strain. Strategy 2 strain using P22 lysozymes. TT means translational terminator. |
| SD124 | ΔnrsBAC11::$P_{nrsB29}$ 13 TT Inv($P_{psbA223}$ 19 15)-23 | SD102 pψ124 | Nickle inducible lysis strain. Strategy 2 strain using P22 lysozymes, different orientation for constitutive lysis cassette |
| SD128 | ΔnrsBAC11::$P_{nrsB29}$ 13 TT $P_{psbA231}$ 15 | SD102 pψ128 | Nickle inducible lysis strain. Strategy 2 strain using P22 endolysin |
| SD129 | ΔnrsBAC11::$P_{nrsB29}$ 13 TT $P_{psbA223}$ 19 15 Δsll1951-15::sacB Km$^R$ | SD123 pψ228 | Nickle inducible lysis strain. Strategy 2 strain using P22 lysozymes With S-layer deletion. Can not be constructed, suggesting that S-layer can not be deleted under a background of constitutive expression of the endolysin genes. |
| SD200 | ΔlipA22::sacB Km$^R$ | SD100 pψ200 | Intermediate strain for Optimization Strategy 1, to enable insertion of foreign genes at the lipA locus |
| SD201 | ΔlipA22::$P_{psbA231}$ atfA RBS phaP | SD200 pψ201 | Neutral lipid producing strain, stocked. The phaP here is directly PCRed from the bacteria, in which the original gene is assigned as phaP1. |

TABLE 1-continued

The *Synechocystis* strains used or developed for this invention

| SD # | Genotype | Parent plasmid | Description/Derivation |
|---|---|---|---|
| SD202 | ΔlipA22::Inv($P_{psbA231}$ atfA RBS phaP)-32 | SD200 pψ202 | Neutral lipid producing strain, stocked |
| SD203 | ΔlipA22::$P_{psbA231}$ atfA RBS phaP ΔnrsBAC11::$P_{nrsB22}$ 13 Inv($P_{psbA223}$ 19 15)-23 | SD201 pψ104 | Neutral lipid producing strain SD104 + SD 201, a double mutant strain, which can release TAG oil drops after $Ni^{2+}$ addition. Stocked. |
| SD204 | ΔlipA22::Inv($P_{psbA231}$ atfA RBS phaP)-32 ΔnrsBAC11::$P_{nrsB22}$ 13 Inv($P_{psbA223}$ 19 15)-23 | SD205 pψ104 | Neutral lipid producing strain SD104 + SD202, a double mutant strain, which can release TAG oil drops after $Ni^{2+}$ addition. Stocked. Unstable |
| SD205 | ΔlipA22::sacB $Km^R$ ΔnrsBAC11::$P_{nrsB22}$ 13 Inv($P_{psbA223}$ 19 15)-23 | SD104 pψ200 | SD104 + SD 200, Intermediate strain for SD 203, 204 and 211. To insert foreign gene at ΔlipA22 locus. For SD211 construction |
| SD206 | slr1704-50::sacB $Km^R$ | SD100 pψ206 | Intermediate strain for Optimization Strategy 2, SD209. The foreign genes will be inserted at the slr1704 locus. |
| SD207 | Δ(slr1993-slr1994)-14::sacB $Km^R$ | SD100 pψ207 | Intermediate strain for SD210, optimization Strategy 4, deleting the PHA synthesis genes |
| SD208 | ΔlipA22::$P_{rbc34}$ aftA69 RBS pha-68 | SD200 pψ208 | Neutral lipid producing strain. Optimized SD201 using new codons. Optimization Strategy 1. At the same locus. aftA69 pha-68 are two synthesized genes based on the codon optimization of aftA and phaP. |
| SD210 | Δ(slr1993-slr1994)-14::$P_{rbc34}$ aftA69 RBS pha-68 | SD207 | Neutral lipid producing strain Optimization Strategy 4 for oil production stability, deleting the PHA synthesis genes |
| SD211 | ΔlipA22::$P_{rbc34}$ aftA69 RBS pha-68 ΔnrsBAC11::P22 13 Inv($P_{psbA223}$ 15 19)-23 | | Neutral lipid producing strain with nickel inducible lysis. SD208 + SD 104, Optimized oil producing stain with Nickel inducing lysis. |
| SD212 | Δ(slr1993-slr1994)-14::$P_{rbc34}$ aftA69 RBS pha-68 slr1704-50::sacB $Km^R$ | SD210 | SD210 + SD206, intermediate strain for double mutant SD213. |
| SD213 | Δ(slr1993-slr1994)-14::$P_{rbc34}$ aftA69 RBS pha-68 slr1704-50::$P_{rbc34}$ aftA69 RBS pha-68 | SD212 | SD210 + SD209, double mutant with two copies of aftA69. |
| SD214 | Δaas-23::sacB $Km^R$ | SD100 pψ213 | Deletion of slr1609 |
| SD216 | Δaas-23::$P_{psbA236}$ tesA136 | SD214 pψ216 | FFA secretion strain. *E. coli* 'tesA gene fused with an HA tag is driven by $P_{psbA2}$, with the same orientation of $P_{aas}$, as the deleted aas gene. |
| SD217 | Δaas-23::Inv($P_{psbA236}$ tesA136)-44 | SD214 pψ217 | FFA secretion strain. *E. coli* 'tesA gene fused with an HA tag is driven by $P_{psbA2}$, with the opposite orientation of $P_{aas}$, as the deleted aas gene. |
| SD218 | Δ(slr1993-slr1994)-14::$P_{cpc37}$ accBC27(Ec)$P_{rbc38}$ accD(Ec) RBS accA30(Ec) | SD207 pψ218 | FFA secretion strain. From SD207, overexpression *E. coli* accBCDA genes in Syn at the locus deleting genes for PHB synthesis. |
| SD219 | ΔnrsBAC11::$P_{nrsR35}$ tesA136 Δ(slr1993-slr1994)-14::sacB $Km^R$ | SD215 pψ207 | FFA secretion strain. SD215 + S4KS deleting PHB synthesis genes slr1993 and slr1994 |
| SD220 | Δaas-23::$P_{psbA236}$ tesA136 Δ(slr1993-slr1994)-14::sacB $Km^R$ | SD216 pψ207 | FFA secretion strain. SD216 + S4KS deleting PHB synthesis genes slr1993 and slr1994 |
| SD221 | Δaas-23::Inv($P_{psbA236}$ tesA136)-44 Δ(slr1993-slr1994)-14::sacB $Km^R$ | SD217 pψ207 | FFA secretion strain. SD217 + S4KS deleting PHB synthesis genes slr1993 and slr1994 |
| SD222 | ΔnrsBAC11::$P_{nrsB35}$ tesA136 Δ(slr1993-slr1994)-14::$P_{cpc37}$ accBC27(Ec) $P_{rbc38}$ accD(Ec) RBS accA30(Ec) | SD219 pψ218 | FFA secretion strain. SD219 + EcoACCs overproduction |

TABLE 1-continued

The *Synechocystis* strains used or developed for this invention

| SD # | Genotype | Parent plasmid | Description/Derivation |
|---|---|---|---|
| SD223 | ΔnrsBAC11::$P_{nrsB35}$ tesA136 Δ(slr1993-slr1994)-14::$P_{cpc39}$ accB RBS accC70 $P_{rbc40}$ accD RBS accA | SD219 pψ225 | FFA secretion strain. SD219 + SynACCs overproduction |
| SD224 | Δaas-23::$P_{psbA236}$ tesA136 Δ(slr1993-slr1994)-14::$P_{cpc37}$ accBC27(Ec) $P_{rbc38}$ accD(Ec) RBS accA30(Ec) | SD220 pψ218 | FFA secretion strain. SD220 + EcoACCs overproduction |
| SD225 | Δaas-23::$P_{psbA236}$ tesA136 Δ(slr1993-slr1994)-14::$P_{cpc39}$ accB RBS accC70 $P_{rbc40}$ accD RBS accA | SD220 pψ225 | FFA secretion strain. SD220 + SynACCs overproduction |
| SD226 | Δaas-23::Inv($P_{psbA236}$ tesA136)-44 Δ(slr1993-slr1994)-14::$P_{cpc37}$ accBC27(Ec) $P_{rbc38}$ accD(Ec) RBS accA30(Ec) | SD221 pψ218 | FFA secretion strain. SD221 + EcoACCs overproduction |
| SD227 | Δaas-23::Inv($P_{psbA236}$ tesA136)-44 Δ(slr1993-slr1994)-14::$P_{cpc39}$ accB RBS accC70 $P_{rbc40}$ accD RBS accA | SD221 pψ225 | FFA secretion strain. SD221 + SynACCs overproduction |
| SD228 | ΔnrsBAC11::$P_{nrsB}$ tesA136 Δ(slr1993-slr1994)-14::$P_{cpc39}$ accB RBS accC70 $P_{rbc40}$ accD RBS accA Δsll1951-15::sacB Km$^R$ | SD223 pψ228 | FFA secretion strain. SD223 + deletion of genes for S-layer |
| SD229 | Δaas-23::$P_{psbA236}$ tesA136 Δ(slr1993-slr1994)-14::$P_{cpc39}$ accB RBS accC70 $P_{rbc40}$ accD RBS accA Δsll1951-15::sacB Km$^R$ | SD225 pψ228 | FFA secretion strain. SD225 + deletion of genes for S-layer |
| SD230 | Δaas-23::Inv($P_{psbA236}$ tesA136)-44 Δ(slr1993-slr1994)-14::$P_{cpc39}$ accB RBS accC70 $P_{rbc40}$ accD RBS accA Δsll1951-15::sacB Km$^R$ | SD227 pψ228 | FFA secretion strain. SD227 + deletion of genes for S-layer |
| SD231 | ΔnrsBAC11::$P_{nrsB35}$ tesA136 Δ(slr1993-slr1994)-14::$P_{cpc39}$ accB RBS accC70 $P_{rbc40}$ accD RBS accA Δsll1951-15::$P_{psbA210}$ fatB161(Uc) $P_{rbc41}$ fatB262(Ch) | SD228 pψ230 | FFA secretion strain. SD223 + deletion of genes for S-layer + short chain TEs The B1 and B2 mean these are mutated fatB genes. Since these were codon-optimized genes they were "mutated". |
| SD232 | Δaas-23::$P_{psbA236}$ tesA136 Δ(slr1993-slr1994)-14::$P_{cpc39}$ accB RBS accC70 $P_{rbc40}$ accD RBS accA Δsll1951-15::$P_{psbA210}$ fatB16 (Uc) $P_{rbc41}$ fatB262(Ch) | SD230 pψ230 | FFA secretion strain. SD225 + deletion of genes for S-layer + short chain TEs |
| SD233 | Δaas-23::$P_{psbA236}$ tesA136 Δ(slr1993-slr1994)-14::$P_{cpc39}$ accB RBS accC70 $P_{rbc40}$ accD RBS accA Δsll1951-15::$P_{psbA210}$ fatB161(Uc) $P_{rbc41}$ fatB262(Ch) ΔnrsBAC11::$P_{nrsB21}$ 13 Km$^R$ sacB | SD232 pψ102 | FFA secretion strain. On the basis of SD232, an intermediate strain for inserting genes under the control of Ni inducible promoter. |
| SD234 | $P_{cmp16}$::Km$^R$ sacB RBS | SD100 pψ234 | An intermediate strain for inserting genes under the control of $P_{cmp}$ |
| SD235 | Δaas-23::$P_{psbA236}$ tesA136 Δ(slr1993-slr1994)-14::$P_{cpc39}$ accB RBS accC70 $P_{rbc40}$ accD RBS accA Δsll1951-15::$P_{psbA210}$ fatB161(Uc) $P_{rbc41}$ fatB262(Ch) $P_{cmp16}$::Km$^R$ sacB RBS | SD232 pψ234 | On the basis of SD232, an intermediate strain for inserting genes under the control of $P_{cmp}$ |
| SD236 | ΔnrsBAC11::$P_{nrsB42}$ fol RBS shl | SD102 pψ236 | Nickel controlling lipolysis genes |
| SD237 | $P_{cmp43}$::fol RBS shl RBS | SD234 pψ237 | Green Recovery strain. $CO_2$ limitation controlling lipolysis genes |

TABLE 1-continued

The *Synechocystis* strains used or developed for this invention

| SD # | Genotype | Parent plasmid | Description/Derivation |
|---|---|---|---|
| SD238 | Δaas-23::$P_{psbA236}$ tesA136 Δ(slr1993-slr1994)-14::$P_{cpc39}$ accB accC70 $P_{rbc40}$ accD accA Δsll1951-15::$P_{psbA210}$ fatB161(Uc) $P_{rbc41}$ fatB262(Ch) ΔnrsBAC11::$P_{nrsB42}$ fol RBS shl | SD233 pψ236 | SD232 + Nickel controlling lipases |
| SD239 | Δaas-23::$P_{psbA236}$ tesA136 Δ(slr1993-slr1994)-14::$P_{cpc39}$ accB RBS accC70 $P_{rbc40}$ accD RBS accA Δsll1951-15::$P_{psbA210}$ fatB161(Uc) $P_{rbc41}$ fatB262(Ch) $P_{cmp43}$:: fol shl RBS | SD235 pψ237 | Green Recovery plus FFA secretion strain. SD232 + $CO_2$ controlling lipases |
| SD240 | Δaas-23::$P_{psbA236}$ tesA136 Δ(slr1993-slr1994)-14::$P_{cpc39}$ accB RBS accC70 $P_{rbc40}$ accD RBS accA Δsll1951-15::$P_{psbA210}$ fatB161(Uc) $P_{rbc40}$ fatB262(Ch) Δ(slr2001-slr2002)-17::$Km^R$ sacB | SD232 pψ240 | On the basis of SD232, an intermediate strain for inserting genes at the cyanophycin synthesis gene deletion site. |
| SD241 | ΔlipA22::Inv($P_{psbA231}$ atfA phaP)-32 Δ(slr1993-slr1994)-14::sacB $Km^R$ | SD202 pψ207 | On the basis of SD232, an intermediate strain for inserting genes at the PHB synthesis gene deletion site. |
| SD242 | ΔlipA22:: Inv($P_{psbA231}$ atfA phaP)-32 Δ(slr1993-slr1994)-14::$P_{cpc}$ fadD(Ec) $P_{psbA236}$ tesA136 | SD241 pψ242 | $2^{nd}$ neutral lipid exploration. Acyl-CoA overexpression on the basis of SD202 (WS/DGAT overproduction). The fadD(Ec) here is a real acyl-CoA synthetase gene (fadD) introduced from *Ecoli*. Failed in transformation by lethality, for the first time, suggesting that the atfA, fadD and tesA genes cannot be put together in 6803. |
| SD243 | Δaas-23::$P_{psbA2}$ tesA136 Δ(slr1993-slr1994)-14::$P_{cpc39}$ accB RBS accC70 $P_{rbc40}$ accD RBS accA Δsll1951-15::$P_{psbA210}$ fatB161(Uc) $P_{rbc41}$ fatB262(Ch) Δ(slr2001-slr2002)-17::$P_{psbA211}$ fatB262(Ch) | SD240 pψ243 | Further optimization for C8 C10 shorter chain fatty acid production and deletion of genes for cyanophycin synthesis, on the basis of SD232 |
| SD244 | $P_{sbtA18}$::sacB $Km^R$ RBS | SD100 pψ244 | Intermediate strain for $CO_2$ controlling, The sacB Km$^r$ cassette was inserted between $P_{sbtA}$ and sbtA. There is a duplicated RBS for the downstream sbtA gene. |
| SD245 | $P_{cmp16}$::$P_{cmp43}$ fol RBS shl RBS $P_{sbtA18}$::sacB $Km^R$ RBS | SD237 pψ244 | Intermediate strain for $CO_2$ controlling, Parent SD237 |
| SD246 | Δaas-23::$P_{psbA236}$ tesA136 Δ(slr1993-slr1994)-14::$P_{cpc39}$ accB RBS accC70 $P_{rbc40}$ accD RBS accA Δsll1951-15::$P_{psbA210}$ fatB161(Uc) $P_{rbc41}$ fatB262(Ch) $P_{cmp43}$::fol RBS shl RBS $P_{sbtA18}$::sacB $Km^R$ RBS | SD239 pψ244 | FFA secretion strain with Green Recovery. Intermediate strain for CO2 controlling, Parent SD239 |
| SD247 | Δaas-23::$P_{psbA236}$ tesA136 Δ(slr1993-slr1994)-14::$P_{cpc39}$ accB RBS accC70 $P_{rbc40}$ accD RBS accA Δsll1951-15::$P_{psbA210}$ fatB161(Uc) $P_{rbc41}$ fatB262(Ch) Δ(slr2001-slr2002)-17::$P_{psbA211}$ fatB262(Ch) ΔnrsBAC11::$P_{nrsB21}$ 13 $Km^R$ sacB | SD243 pψ102 | Intermediate strain for SD250 On the basis of 243, an intermediate strain for inserting genes under the control of Ni inducible promoters. |

TABLE 1-continued

The Synechocystis strains used or developed for this invention

| SD # | Genotype | Parent plasmid | Description/Derivation |
|---|---|---|---|
| SD248 | Δaas-23::$P_{psbA236}$tesA136 Δ(slr1993-slr1994)-14::$P_{cpc39}$ accB RBS accC70 $P_{rbc40}$ accD RBS accA Δsll1951-15::$P_{psbA210}$ fatB161(Uc) $P_{rbc41}$ fatB262(Ch) Δ(slr2001-slr2002)-17::$P_{psbA211}$ fatB262(Ch) Δslr1710-19::$Km^R$ sacB | SD243 pψ248 | Intermediate strain from SD243 On the basis of SD243, an intermediate strain for inserting genes at the penicillin binding protein 2 (PBP2) gene deletion site. |
| SD249 | Δaas-23::$P_{psbA236}$tesA136 Δ(slr1993-slr1994)-14::$P_{cpc39}$ accB RBS accC70 $P_{rbc40}$ accD RBS accA Δsll1951-15::$P_{psbA210}$ fatB161(Uc) $P_{rbc41}$ fatB262(Ch) Δ(slr2001-slr2002)-17::$P_{psbA211}$ fatB262(Ch) Δslr1710-19::$P_{psbA210}$ fatB163(Cc) | SD248 pψ249 | FFA secretion strain. $5^{th}$ generation modification strain SD243 with PBP2 deletion and Cc FatB1 (C14:0) overproduction |
| SD250 | Δaas-23::$P_{psbA236}$tesA136 Δ(slr1993-slr1994)-14::$P_{cpc39}$ accB RBS accC70 $P_{rbc40}$ accD RBS accA Δsll1951-15::$P_{psbA210}$ fatB161(Uc) $P_{rbc41}$ fatB262(Ch) Δ(slr2001-slr2002)-17::$P_{psbA211}$ fatB262(Ch) Δslr1710-19::$P_{psbA244}$ atfA $P_{cpc45}$ fadD(Ec) | SD248 pψ250 | $3^{rd}$ neutral lipid exploration Put FadD and WS/DGAT on the basis of SD243 Cannot be constructed, failed in transformation by lethality, for the second time, suggesting that the atfA, fadD and tesA genes cannot be put together in 6803. |
| SD251 | Δaas-23::$P_{psbA236}$tesA136 Δ(slr1993-slr1994)-14::$P_{cpc39}$ accB accC70 $P_{rbc40}$ accD accA Δsll1951-15::$P_{psbA210}$ fatB161(Uc) $P_{rbc41}$ fatB262(Ch) Δ(slr2001-slr2002)-17::$P_{psbA210}$ fatB262(Ch) ΔnrsBAC11::$P_{nrsB46}$ atfA $P_{cpc45}$ fadD(Ec) | SD247 pψ251 | $3^{rd}$ neutral lipid exploration backup, Controllable synthesis of FadD and WS/DGAT on the basis of SD243 |
| SD252 | $P_{sbtA46}$::gpl RBS | SD244 pψ252 | Green Recovery strain. GPL controlled by $P_{sbtA}$. I duplicated a RBS for sbtA if the ribosome can come down through gpl for sbtA. |
| SD253 | $P_{cmp43}$::fol RBS shl RBS $P_{sbtA46}$::gpl RBS | SD245 pψ252 | Green Recovery strain. Combination of SD252 and SD237 |
| SD254 | Δaas-23::$P_{psbA236}$tesA136 Δ(slr1993-slr1994)-14::$P_{cpc39}$ accB RBS accC70 $P_{rbc40}$ accD accA Δsll1951-15::$P_{psbA210}$ fatB161(Uc) $P_{rbc41}$ fatB262(Ch) $P_{cmp43}$::fol RBS shl RBS $P_{sbtA46}$::gpl RBS | SD246 pψ252 | Green Recovery strain with FFA secretion. Combination of SD252, SD237 and SD232 |
| SD256 | $P_{cmp47}$::fol RBS | SD234 pψ256 | Green Recovery strain. $1^{ST}$ CO2 limitation test strain for Fol individually |
| SD257 | $P_{cmp48}$::shl RBS | SD234 pψ257 | Green Recovery strain. $1^{ST}$ CO2 limitation test strain for Shl individually |
| SD258 | $P_{cmp49}$::gpl RBS | SD234 pψ258 | Green Recovery strain. $1^{ST}$ CO2 limitation test strain for Gpl individually |
| SD260 | $P_{cmp43}$::fol RBS shl RBS $P_{sbtA50}$::gpl RBS 13 19 15 RBS | SD245 pψ260 | Green Recovery strain. Looking for a faster lysis rate. |
| SD262 | Δaas-23::$P_{psbA236}$tesA136 Δ(slr1993-slr1994)-14::$P_{cpc39}$ accB RBS accC70 $P_{rbc40}$ accD RBS accA Δsll1951-15::$P_{psbA210}$ fatB161(Uc) $P_{rbc41}$ fatB262(Ch) $P_{cmp43}$::fol RBS shl RBS $P_{sbtA50}$::gpl RBS 13 19 15 RBS | SD246 pψ260 | Green Recovery strain. Fast autolysis FFA secreting strain. |

TABLE 1-continued

The *Synechocystis* strains used or developed for this invention

| SD # | Genotype | Parent plasmid | Description/Derivation |
|---|---|---|---|
| SD273 | Δaas-23::$P_{psbA236}$ tesA136<br>Δ(slr1993-slr1994)-14::$P_{cpc39}$ accB RBS accC70 $P_{rbc40}$ accD RBS accA<br>Δsll1951-15::$P_{psbA210}$ fatB161(Uc) $P_{rbc41}$ fatB262(Ch)<br>Δ(slr2001-slr2002)-17::$P_{psbA211}$ fatB262(Ch)<br>Δslr2132-22:: $P_{psbA212}$ faa138 $P_{cpc45}$ fadD(Ec) | SD269<br>pψ273 | Acyl-CoA overexpression strain. SD243 + S22Pa2FAA2PcpcFadD faa138 is a synthesized gene for Faa2p from *Saccharomyces cerevisiae*, a long chain fatty acyl-CoA synthetase accepts a wider range of acyl chain lengths than Faa1p, preferring C9:0-C13:0; involved in the activation of endogenous pools of fatty acids. fadD(Ec) is the acyl-CoA ligase from *E. coli*. |
| SD274 | Δaas-23::$P_{psbA236}$ tesA136<br>Δ(slr1993-slr1994)-14::$P_{cpc39}$ accB RBS accC70 $P_{rbc40}$ accD RBS accA<br>Δsll1951-15::$P_{psbA210}$ fatB161(Uc) $P_{rbc41}$ fatB262(Ch)<br>Δ(slr2001-slr2002)-17::$P_{psbA211}$ fatB262(Ch)<br>Δslr2132-22:: $P_{trc}$ tesA137 | SD269<br>pψ274 | FFA secretion strain. SD243 + $P_{trc}$ tesA137<br>See how $P_{trc}$ works in 6803. |
| SD277 | Δaas-23::$P_{psbA236}$ tesA136<br>Δ(slr1993-slr1994)-14::$P_{cpc39}$ accB RBS accC70 $P_{rbc40}$ accD RBS accA<br>Δsll1951-15::$P_{psbA210}$ fatB161(Uc) $P_{rbc41}$ fatB262(Ch)<br>Δ(slr2001-slr2002)-17::$P_{psbA211}$ fatB262(Ch)<br>Δslr1710-19::$P_{psbA210}$ fatB163(Cc)<br>Δslr2132-22:: $P_{trc}$ tesA137 | SD256<br>pψ274 | FFA secretion strain. SD249 + $P_{trc}$ tesA137<br>See how $P_{trc}$ works in 6803. |
| SD278 | Δaas-23::$P_{psbA236}$ tesA136<br>Δ(slr1993-slr1994)-14::$P_{cpc39}$ accB RBS accC70 $P_{rbc40}$ accD RBS accA<br>Δsll1951-15::$P_{psbA210}$ fatB161(Uc) $P_{rbc41}$ fatB262(Ch)<br>$P_{cmp47}$::fol RBS | SD235<br>pψ256 | FFA secretion strain with Green Recovery. SD232 + SD256 |

Example 3

Increasing the TAG Production by Optimizing Strain Construction and the Cyanobacteria Growth Conditions To increase the TAG production in 6803, two strategies were applied in this invention. The first is to insert an optimized WS/DGAT gene, which sequence has been codon optimized for the maximum protein synthesis in 6803. The second is to adjust the strain growth conditions.

For the first strategy, the *Acinetobacter baylyi* sp. ADP1 WS/DGAT gene atfA has been codon edited based on the codon bias of the highly expressed 6803 genes, also based on the secondary mRNA structure prediction that will eliminate the possible stem-loop structures, which would lead to shorter mRNA half lives. The redesigned gene was assigned as aftA69. In the redesigning, aftA69 was constructed as a part of the neutral lipid producing cassette $P_{rbc34}$ aftA69 RBS pha-68, where $P_{rbc34}$ is the promoter of 6803 rbc operon, RBS is ribosome binding site, and pha-68 is a redesigned from *Ralstonia eutropha* gene PhaP1. This cassette $P_{rbc34}$ aftA69 RBS pha-68 was inserted into a site close to slr1704-50 to generate SD209 slr1704-50::$P_{rbc34}$ aftA69 RBS pha-68. In another strain SD210, this cassette $P_{rbc34}$ aftA69 RBS pha-68 was inserted into replace the PHB synthesis genes slr1993 and slr1994 to generate strain SD210 Δ(slr1993-slr1994)-14::$P_{rbc34}$ aftA69 RBS pha-68. The detailed methods of the constructions are described in Example 11. The detailed strain constructions are described in Table 1.

The lipid profiles of the neutral lipid constructions are listed in Table 2 where the membrane lipids (PG, SQDG, MGDG, and DGDG) and the produced TAGs are measured by HPLC-MS. According to Table 1, the TAGs only count for 0.10% in WT, but the TAG percentages increased to 0.57%, 0.72% and 0.56% in the first generation TAG strains SD201, SD202, and SD203 respectively, and the TAG percentages kept increasing to 1.77% and 2.20% in the second generation strains SD209 and SD210 respectively. This result showed the success of increasing neutral lipid production by genetic optimization.

Figure 7:
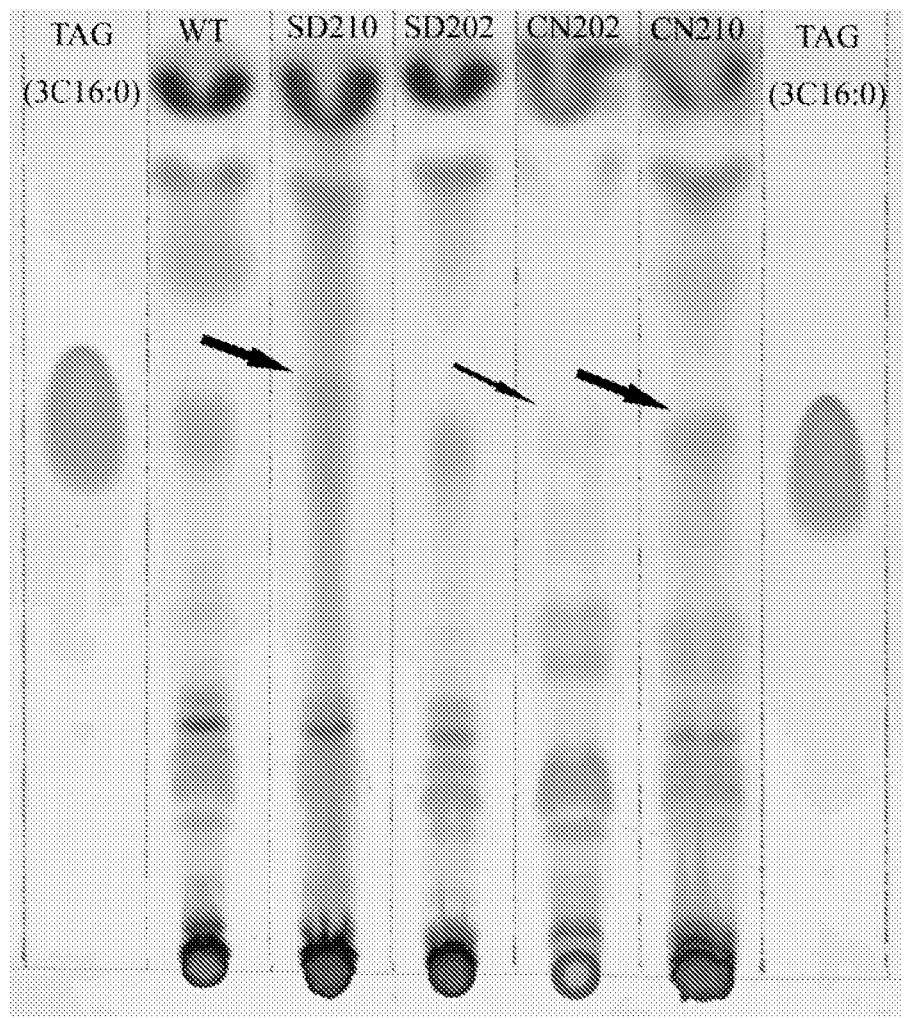
FIG. 7 depicts TLC analysis of the total lipids of SD210 and SD202 grown in BG-11 medium and high carbon-to-nitrogen BG-11 medium (CN210 and $CN_2O_2$), where 10 mM glucose was added to BG11 to increase carbon from 0.19 mM (0.2 mg/l $NaCO_3$) to 60.19 mM, and $NaNO_3$ was decreased from 3 g/L to 0.03 g/L. On the most right and left lanes TAG with three C16:0 serves as control. The arrows indicate overproduced TAGs from the total lipid extracts.

For the second strategy, the strain SD210 was grown in a high carbon-to-nitrogen medium, as most bacteria with TAG accumulation drastically increased the number of the TAG bodies and lipid content in the high carbon-to-nitrogen medium. For adjusting the carbon-to-nitrogen ratio, 10 mM glucose was added to BG11 to increase carbon from 0.19 mM (0.2 mg/l $NaCO_3$) to 60.19 mM, and $NaNO_3$ was decreased from 3 g/L to 0.03 g/L, which resulted a carbon-to-nitrogen ration increase of 31700 fold. The lipid profiles of SD210 grown in the high carbon-to-nitrogen medium is also shown in Table 2 (column CN210). According to Table 2, the TAG percentage of SD210 increased from 2.20% to 2.83% when cultivated in high carbon-to-nitrogen medium. The TLC (thin layer chromatography) analysis of SD210 also indicated that SD210 was capable of producing TAGs and the production was higher when this strain was cultivated in high carbon-to-nitrogen medium (FIG. 7).

As shown in Table 3, the lysis rate of the Strategy 2 strain is higher than that of the Strategy 1 strain. The results for SD204 suggest that the TAG-producing strain is able to be lyzed for TAG release by the nickel inducible lysis system.

TABLE 2

TLC analysis of the total lipids of SD210 and SD202 grown in BG-11 medium and high carbon-to-nitrogen BG-11 medium (CN210 and CN202), where 10 mM glucose was added to BG11 to increase carbon from 0.19 mM (0.2 mg/l NaCO$_3$) to 60.19 mM, and NaNO$_3$ was decreased from 3 g/L to 0.03 g/L. On the most right and left lanes TAG with three C16:0 serves as control. The arrows indicate overproduced TAGs from the total lipid extracts.

| LIPID TYPE | | m/z | WT | SD201 | SD202 | SD203 | SD209 | SD210 | CN210 |
|---|---|---|---|---|---|---|---|---|---|
| PG | 16-16:2 | 717.5 | ND | ND | ND | ND | 7.50 | 5.82 | 0.00 |
|  | 16-16:1 | 719.49 | 220.37 | 43.82 | 64.44 | 33.22 | 37.62 | 29.85 | 17.29 |
|  | 16-16:0 | 721.5 | 136.45 | 17.72 | 41.27 | 15.18 | 35.63 | 11.93 | 89.33 |
|  | 16-18:0 | 749.54 | 0.00 | 0.00 | 0.00 | 0.00 | 0.00 | 0.00 | 167.68 |
| SQDG | 16-16:3 | 787.47 | 21.00 | 39.35 | 226.68 | 36.50 | 167.03 | 60.08 | 0.00 |
|  | 16-16:0 | 793.51 | 3815.98 | 2324.70 | 4452.16 | 1718.27 | 3165.24 | 1420.43 | 1968.27 |
|  | 16-17:2 | 803.5 | 54.59 | 179.14 | 62.99 | 142.91 | 40.70 | 149.97 | 0.00 |
|  | 16-17:1 | 805.51 | 97.51 | 373.64 | 173.61 | 517.96 | 33.84 | 341.61 | 67.76 |
|  | 16-17:0 | 807.53 | 39.99 | 168.99 | 48.52 | 214.00 | 18.81 | 97.00 | 104.79 |
|  | 16-18:0 | 821.54 | 0.00 | 47.92 | 20.56 | 38.68 | 23.98 | 7.61 | 917.57 |
| MGDG | 16-16:2 | 749.52 | 146.61 | 50.79 | 63.16 | 30.05 | 43.59 | 24.01 | 0.00 |
|  | 16-16:1 | 751.53 | 796.91 | 155.08 | 413.08 | 124.59 | 147.57 | 91.40 | 32.24 |
|  | 16-16:0 | 753.55 | 581.16 | 93.74 | 306.03 | 92.14 | 184.38 | 71.17 | 388.23 |
|  | 16-18:1 | 779.56 | 515.08 | 97.27 | 314.55 | 129.01 | 43.72 | 57.43 | 170.99 |
|  | 16-18:0 | 781.58 | 0.00 | 0.00 | 0.00 | 0.00 | 0.00 | 0.00 | 695.36 |
| DGDG | 16-16:1 | 913.59 | 129.10 | 79.84 | 105.47 | 74.40 | 41.37 | 50.92 | 0.00 |
|  | 16-16:0 | 915.59 | 192.78 | 129.59 | 135.92 | 147.92 | ND | ND | 832.66 |
|  | 16-18:0 | 943.63 | ND | ND | ND | ND | ND | ND | 75.00 |
|  | Total membrane |  | 6747.53 | 3801.58 | 6428.42 | 3314.86 | 3990.97 | 2419.23 | 5527.16 |
| Triglycerides | 16-16-16:2 | 825.69 | 1.32 | 4.42 | 2.960 | 1.778 | 1.27 | 1.77 | 1.35 |
|  | 16-16-16:1 | 827.71 | 1.67 | 7.38 | 8.171 | 3.278 | 7.85 | 6.21 | 7.95 |
|  | 16-16-16:0 | 829.73 | 1.32 | 4.05 | 14.036 | 3.556 | 27.33 | 12.76 | 33.10 |
|  | 16-16-18:0 | 857.76 | 0.94 | 2.49 | 13.416 | 3.374 | 18.59 | 16.01 | 54.45 |
|  | 16-16-18:1 | 883.77 | 1.26 | 3.24 | 2.785 | 4.976 | 10.33 | 13.37 | 33.80 |
|  | 16-16-18:0 | 885.79 | 0.15 | 0.38 | 5.408 | 1.415 | 6.36 | 4.20 | 30.35 |
|  | Total TAGS |  | 6.67 | 21.97 | 46.78 | 18.38 | 71.74 | 54.32 | 161.00 |
|  | TAG/Total (%) |  | 0.10 | 0.57 | 0.72 | 0.55 | 1.77 | 2.20 | 2.83 |
| Chl a | NA |  | 1779.90 | 1850.10 | 1899.90 | 1389.90 | 1850.10 | 1140.00 | ND |

Example 4

Combining the Lipid Producing Ability and Inducible Lysis Ability into *Synechocystis*

A number of nickel inducible lysis SD strains were designed and constructed (Table 1). They showed significant cell lysis after addition of nickel to the cell cultures (Table 3). Of these SD strains, SD101 was made first to determine whether the phage-encoded lysis system would work in cyanobacteria. This preliminary design was named Strategy 1, and that is one of the reasons the kanamycin-resistance marker was not removed. For the next step, Strategy 2 was designed to try to achieve a more rapid cell disruption at lower $Ni^{2+}$ concentrations than needed to induce lysis with the Strategy 1 strain. Strategy 2 (SD104) was designed to over express the endolysin genes (P22 19 15) under a strong *Synechocystis* constitutive promoter PpsbAII, while the $Ni^{2+}$ inducible control was used for expression of the holin gene (P22 13). It was hoped that before induction of expression of the holin gene, the endolysins are accumulated in cells, but they cannot reach their substrates in the peptidoglycan layer of the cell wall. Once the holin gene 13 is expressed to produce holes in the lipid membranes from within, the endolysins now can gain access to the peptidoglycan cell wall layer and trigger the lysis process. The detailed strain constructions are described in Table 1.

TABLE 3

Comparison of different lysis strategies

| Strain SD No. | Lysis Strategies Descriptions | Doubling Time (hour) | Mutation Rates to $Ni^{2+}$ Resistance ($10_{-7}$/generation) | Lysis Rates (%/hour) |
|---|---|---|---|---|
| SD100 | Wild type *Synechocystis* | 8.65 | — | — |
| SD101 | Strategy 1, only use phage P22 lysis cassette | 9.8 | 1.39 | 10.05 |
| SD104 | Strategy 2, control P22 holin gene (13), while constitutively expressing endolysin genes (19 and 15) | 11.20 | 0.93 | 15.5 |
| SD204 | Combination of SD104 and SD 202, capable of both TAG production and nickel inducible lysis | 14.21 | 1.02 | 16.5 |

Example 5

Constructing a $CO_2$-Limitation Inducible Lipolytic Enzymes System for 'Green Recovery'

The following example describes how to develop a 'Green Recovery' system for cyanobacteria. With the Green Recovery system, no nickel addition is necessary for induction of lysis. The lysis and release of lipids will be induced by $CO_2$ limitation of the culture. This invention involves lipolytic enzymes that are able to hydrolyze the fatty acyl chains from the membrane lipids (e.g, PG, MGDG, DGDG, and SQDG) for free fatty acids, so that on the lipolytic degradation of the cell membranes (both cytoplastic and thylakoid), the overproduced neutral lipid will be released with the free fatty acid from the membrane lipids producing a lipid mixture.

We previously developed a nickel inducible lysis system for cyanobacterium Synechocystis sp. PCC 6803, which is able to induce the phage lysis genes to break down the cell walls by adding nickel as an inducer. However, this system does not release the cyanobacterial lipids as an easily-recoverable form like triacylglycerols or free fatty acids. Cyanobacterial lipids are mainly in the form of diacylglycerols as the components of membranes, including MGDG (monogalactosyl diacylglycerol), DGDG (digalactosyl diacylglycerol), PG (phosphatidylglycerol), and SQDG (sulfoquinovosyl diacylglycerol). To utilize the lipids in the cyanobacterial biomass, we developed a 'Green Recovery' system, where inducible lipolytic enzymes degrade the membrane lipids into free fatty acids (FFA hereafter) with the collapse of cell. The Green Recovery system controls the lipolytic genes with $CO_2$-limitation inducible promoters, which will switch on the lipolytic genes by stopping $CO_2$ aeration instead of adding eco-unfriendly nickel.

The lipolytic enzymes (EC 3.1.1) hydrolyzing the carboxylic ester bonds to release the fatty acids from the diacylglycerols include galactolipase and phospholipase B. Galactolipase (EC 3.1.1.26) catalyzes the hydrolysis of galactolipids, such as DGDG and MGDG by removing one or two fatty acids. Phospholipase B is an enzyme with a combination of both PLA1 (EC 3.1.1.32) and PLA2 (EC 3.1.1.4) activities; that is, it can cleave acyl chains from both the sn-1 and sn-2 positions of a phospholipid. For the purpose of fatty acid recovery from membrane lipids, we will test the performances of three lipolytic enzymes (from bacteria, fungi, and herbivorous animal digestive juice) in 6803. First, the lipase from Staphylococcus hyicus (Shl) is unique among the bacterial lipases in that it has a very broad substrate spectrum ranging from triacylglycerol lipids of various chain lengths to phospholipids and lysophospholipids. Second, the modified fungal phospholipase from Fusarium oxysporum (Fol) exhibited emerging galactolipase activity as well as increased phosopholipase activity. Third, guinea-pig lipase (Gpl, also called GPLRP2, guinea-pig pancreatic lipase-related protein 2) from the digestive juice of guinea-pig shows the highest galactolipase ever found, and plays a dual role in the digestion of galactolipids and phospholipids, the most abundant lipids occurring in plant thylakoid membranes.

We will use a 6803 inorganic carbon (Ci) limitation response mechanism to develop an inducible transcription system regulated by $CO_2$. Cells of 6803 aerated with $CO_2$-free air for 30 min in the light depleted the total Ci to near zero levels (McGinn et al., 2003). Under these conditions, transcripts for the three inducible Ci uptake systems, ndhF3, sbtA, and cmpA genes, showed near-maximal mRNA abundance at 15 min under Ci limitation. By utilizing their promoter sequences to control the lipase genes, Green Recovery of fatty acids could be initiated by $CO_2$ limitation by stopping aeration of the biomass. Gas supply to the photobioreactor is easy to regulate, and limiting the $CO_2$ supply will be an economical and eco-friendly method to initiate lipid hydrolysis.

Another advantage of the Green Recovery system emerges when combined with the cyanobacterial FFA secretion system. The FFA secretion avoids the energy intensive biomass processes (i.e., concentration and extraction) by directly recovering the secreted FFA from the culture medium. However, the FFA secreting system still requires substantial biomass to achieve cost-effective FFA production, which means a significant amount of fixed carbon has to be converted and stored as lipid membranes. It is expected that the Green Recovery system will convert the lipids into FFAs in the potential spent cyanobacterial biomass generated by the FFA secreting system, and also will cause cell lysis and release the unsecreted intracellular FFAs. With this combination approach, the secreted FFAs, unsecreted FFAs and the membrane FFAs will incorporate and be recovered by one single separation.

Example 6

Green Recovery Strain Construction and Test

Figure 8:
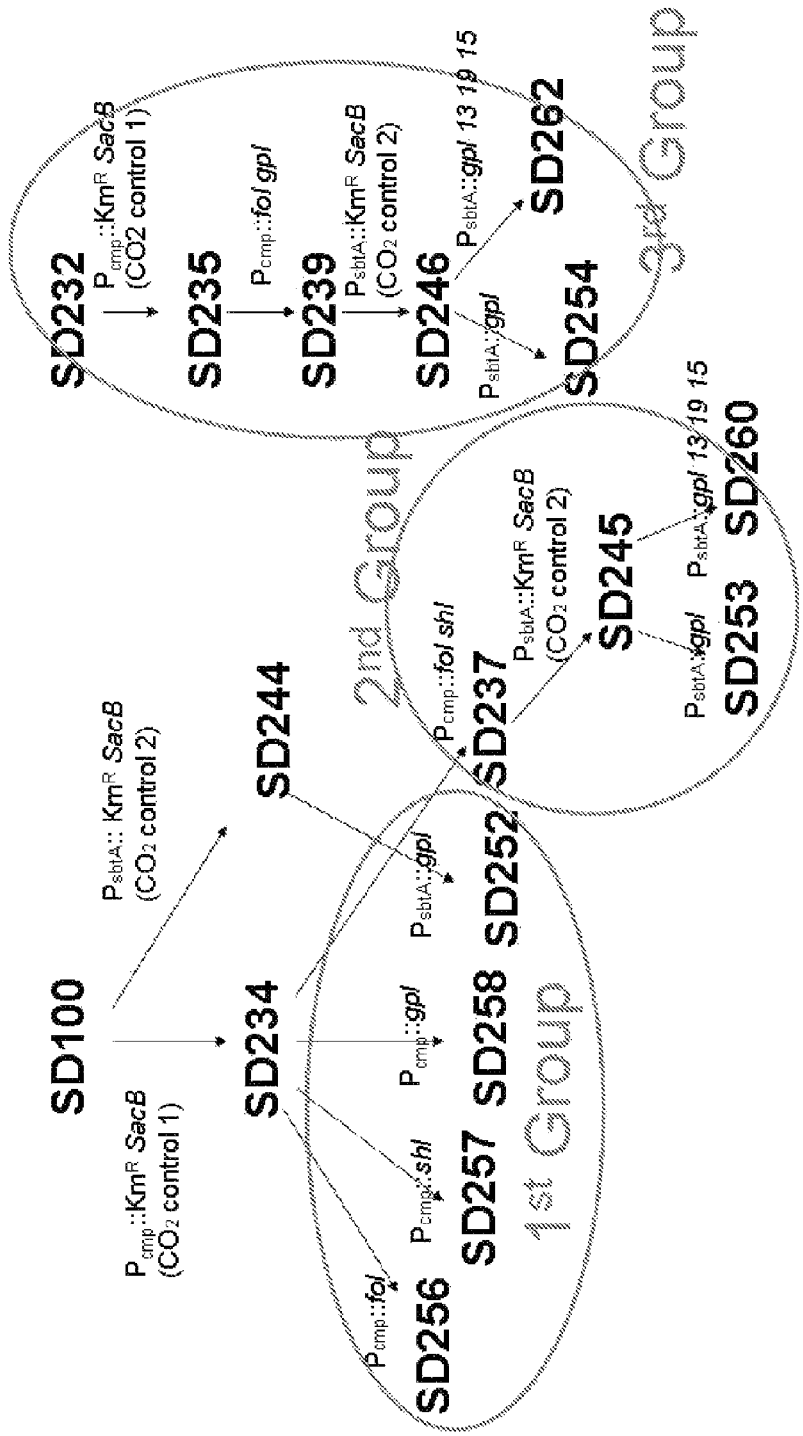
FIG. 8 depicts the genetic genealogy tree of constructing Green Recovery strains.

Three groups of strains were constructed for Green Recovery (Table 1, FIG. 8). The first group consists of four strains (SD256, SD257, SD258, and SD252) to evaluate performances of three lipolytic enzymes and two $CO_2$ responsive promoters in 6803. The second group consists of three strains (SD237, SD252, and SD260) which contain multiple lipolytic enzymes as well as lysozymes (13, 19, and 15) from Salmonella bacteriophage P22 to achieve faster lysis responses to $CO_2$ limitation, and to evaluate the optimal strategy for maximum lipid recovery. The third group consists of three strains (SD235, SD239 and SD246) that incorporate the lipid recovery system into FFA secreting strain (SD232) to evaluate the Green Recovery of FFA after FFA secretion. The genotypes of the experimental strains and their parent strain and intermediate strains are listed in Table 1, and their genealogy is shown in FIG. 8. The growth of the strains is comparable to the wild type, with doubling times of about 9 hours.

Figure 9:
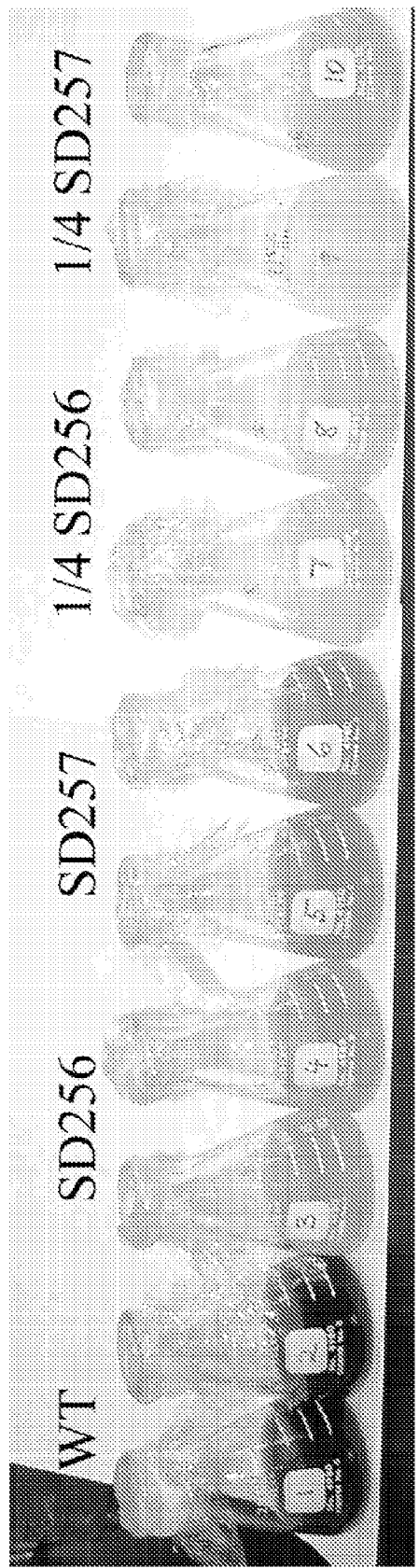
FIG. 9 depicts culture lysis of the Green Recovery strains induced by $CO_2$ limitation.
Figure 10:
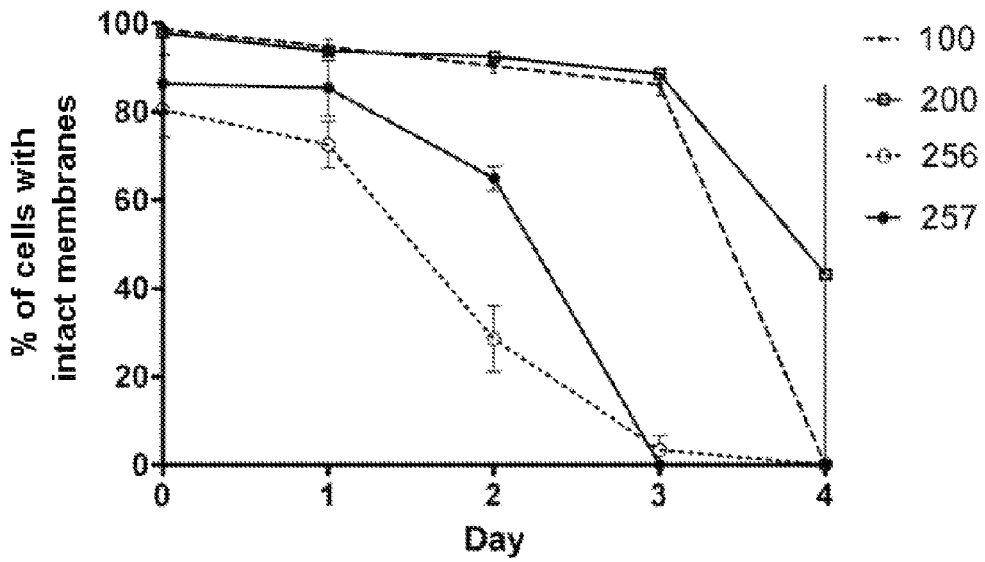
FIG. 10 depicts cell membrane permeability created in the Green Recovery strains by $CO_2$ limitation.

The Green Recovery of some of the strains has been tested for cell lysis and fatty acid release. FIG. 9 showed that the Green Recovery strain cultures significantly lysed after $CO_2$ limitation in flasks at the cell densities of $0.4-3.0 \times 10^9$ cells/ml. As shown in FIG. 10, two Green Recovery strains SD256 and SD257 demonstrated significantly increased membrane permeability after $CO_2$ limitation as revealed by Sytox staining. The 6803 wild-type (SD100) cells also showed membrane damages at high cell density and $CO_2$ limitation conditions. However, when a native lipase gene lipA (slr1969) is deleted from wild type strain 6803 to result in SD200, this lipA deficient strain showed a much lower level of membrane damage at high cell density and $CO_2$ limitation conditions. This suggests that the wild type 6803 cells have a background autolysis at high cell density because of the native lipase gene(s), but in the Green Recovery strains in which exogenous lipolytic genes are controlled by $CO_2$ limitation inducible promoters, the inducible membrane destruction is much stronger than the background autolysis.

The membrane destruction and release of fatty acids into the culture of the Green Recovery strains after $CO_2$ limitation are shown in Table 4. Based on the data in Table 4, the Green Recovery strains SD256 and SD257 released significantly increased fatty acid amounts from cell membranes (11.5 and $10.3 \times 10^{-15}$ g/cell, respectively) after $CO_2$ limitation compared to the amount of the wild-type strain (SD100, $6.3 \times 10^{-15}$ g/cell). Also, the background fatty acid release was dramatically reduced in the lipA deficient strain SD200, which suggests that the native lipase gene or genes caused the background membrane fatty acid release and high cell density autolysis. It is expected that the Green Recovery system can be more precisely controlled by changing the native promoter of lipA gene into a $CO_2$ limitation inducible promoter.

TABLE 4

$CO_2$ limitation inducible membrane destruction and release of fatty acids in the Green Recovery strains.

| Strain | SD100 | SD200 | SD237 | SD256 | SD257 | SD258 |
|---|---|---|---|---|---|---|
| Description | Wild Type | ΔlipA22::sacB $Km^R$ | $P_{cmp43}$::fol RBS shl RBS | $P_{cmp47}$::fol RBS | $P_{cmp48}$::shl RBS | $P_{cmp49}$::gpl RBS |
| Initial cell density ($10^{12}$ cells/L) | 1.37 | 3.42 | 1.96 | 1.92 | 1.69 | 4.03 |
| FFA/cell ($10^{-15}$ g) | 6.3 ± 1.1 | 0.79 ± 0.23 | 7.5 ± 2.1 | 11.5 ± 1.9 | 10.3 ± 0.7 | 1.9 ± 0.1 |
| Time (day) until 50% lysis after $CO_2$ limitation | 3.42 | 4.2 | 2.6 | 1.5 | 2.23 | 3.34 |

Example 7

Conditions for Green Recovery

Figure 11:
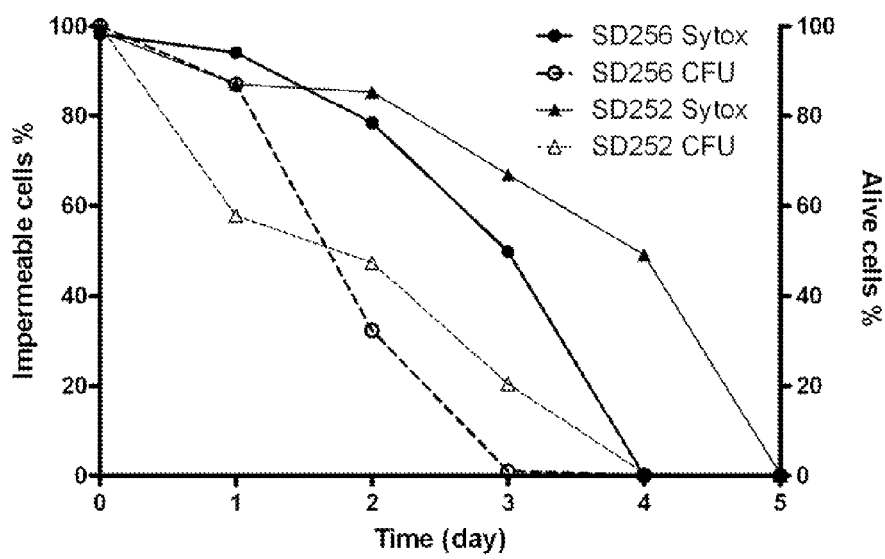
FIG. 11 depicts a plot of the relationship between membrane permeability (revealed by Sytox staining) and cell viability (revealed by CFU) during Green Recovery after $CO_2$ limitation.
Figure 12:
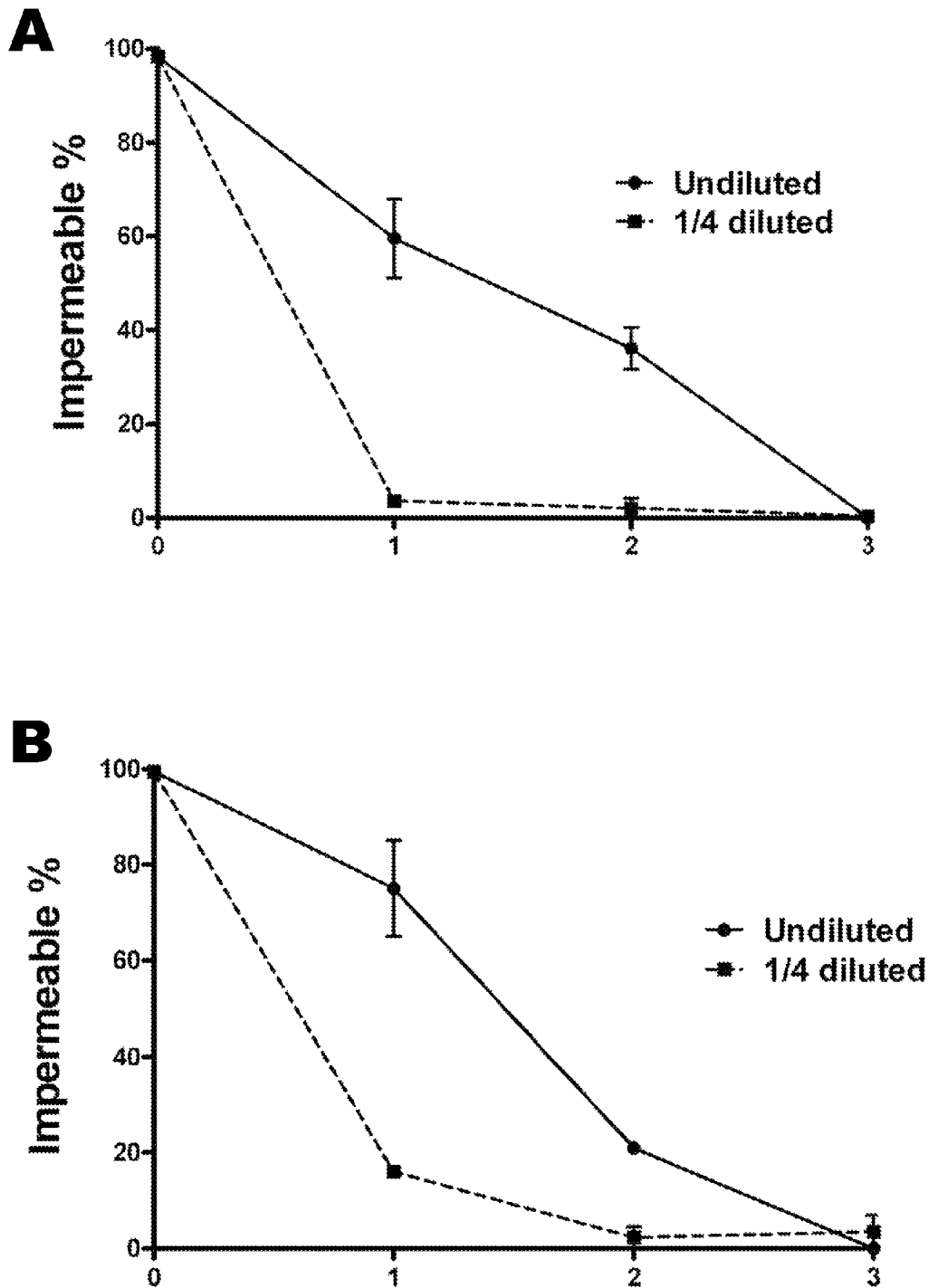
FIG. 12 depicts plots of membrane damage of different SD strains after $CO_2$ limitation with 1/4 and 1/16 dilution of the original culture. A) SD256; B) SD257; C) SD237; D) WT.
Figure 12:
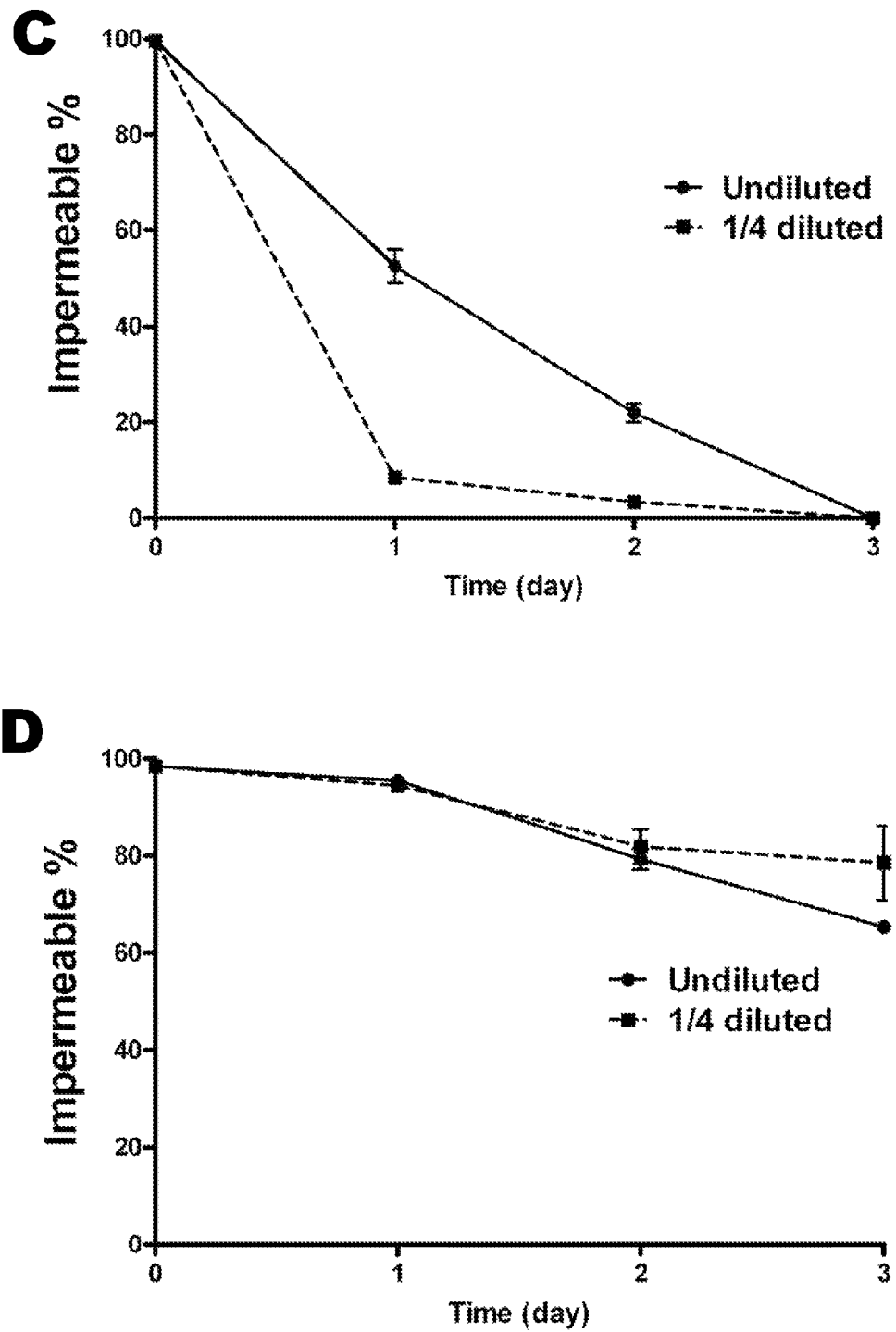
Figure 13:
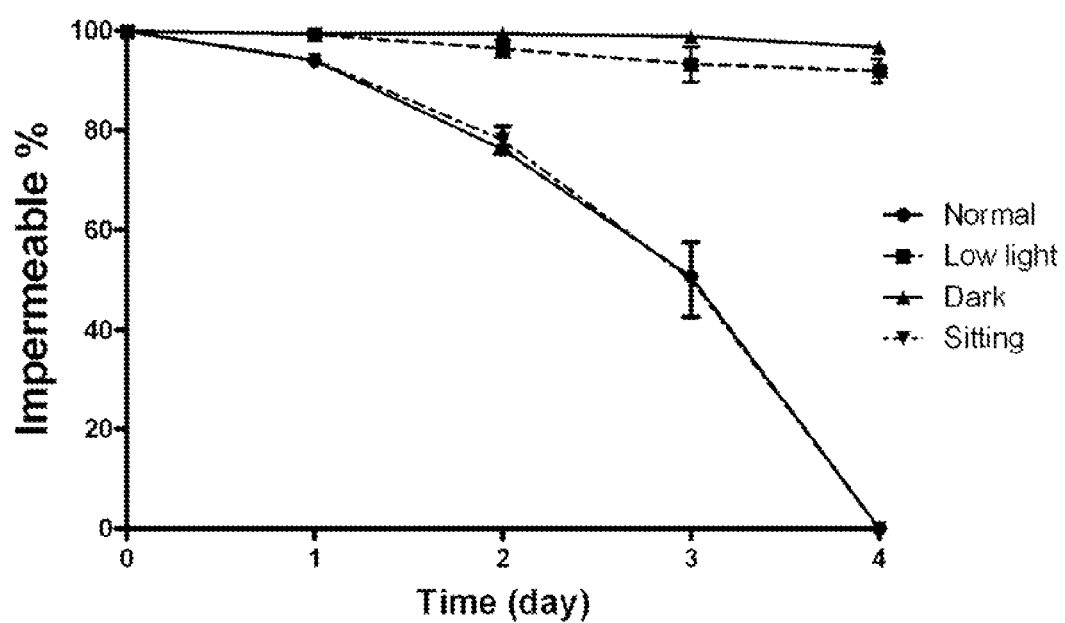
FIG. 13 depicts a plot of membrane damage of SD256 after $CO_2$ limitation under different conditions. Normal means the $CO_2$ limited cultures were rotated at 100 rpm under continuous illumination (140 µmol photons $m^{-2} s^{-1}$); low light means the $CO_2$ limited cultures were rotated at 100 rpm under illumination (20 µmol photons $m^{-2} s^{-1}$); dark means the $CO_2$ limited cultures were rotated at 100 rpm under illumination (2 µmol photons $m^{-2} s^{-1}$); sitting means the $CO_2$ limited cultures were shaken only once per day before sampling and under illumination (140 µmol photons $m^{-2} s^{-1}$).

We tested several optimal conditions for Green Recovery, such as cell density of the cultures (FIG. 11), intensity of illumination (FIG. 12), and agitation of the cultures (FIG. 13). It was observed that the membrane damage was faster and FFA release was higher after 1/4 dilution (about $10^8$ cells/ml) than at the original cell density (about $10^9$ cells/ml) (Table 5 and FIG. 11). Light is essential for Green Recovery, which is negligible in the dark (less than 2 μmol photons $m^{-2}$ $s^{-1}$), and much slower in low light (20 μmol photons $m^{-2}$ $s^{-1}$) than in higher light levels (140 μmol photons $m^{-2}$ $s^{-1}$) (FIG. 12). A probable explanation for these observations is that energy from photosynthesis is required for gene expression, synthesis and function of lipase enzymes. Because of self-shading, photosynthetic cells have a higher metabolic activity at low cell density than at high cell density. This is consistent with the higher FFA yields that we observed at low cell concentrations (Table 5). The intensity of agitation did not affect the rate of lysis; for example, continuous rotation at 60 rpm/min and intermittent shaking (once per day) produced similar membrane damage curves (FIG. 13).

TABLE 5

Membrane damage and FFA yields of SD strains for Green Recovery

| Strain | Genetic Description[a] | Starting cell density (CFU/ml) | Membrane damage[b] (%/day) | Recovered FFA[c] (mg/L) | FFA yield ($10^{-12}$ mg/ cell) |
|---|---|---|---|---|---|
| SD100 | Wild Type | $3.2 \times 10^9$ | 8.9 | 16.5 ± 2.5 | 5.1 ± 0.8 |
| SD200 | ΔlipA::sacB $Km^R$ | $3.4 \times 10^9$ | 2.5 | 2.7 ± 1.1 | 0.8 ± 0.3 |
| SD256 | $P_{cmp}$::fol | $1.6 \times 10^9$ | 35.1 | 19.3 ± 1.0 | 12.4 ± 0.6 |
|  |  | $3.9 \times 10^8$ (¼)[d] | 94.7 | 5.5 ± 0.7 | 14.0 ± 1.8 |
| SD257 | $P_{cmp}$::shl | $2.9 \times 10^9$ | 33.8 | 22.7 ± 1.0 | 7.9 ± 0.4 |
|  |  | $7.2 \times 10^8$ (¼)[d] | 83.4 | 5.7 ± 1.2 | 8.0 ± 1.7 |
| SD237 | $P_{cmp}$::fol RBS shl | $1.5 \times 10^9$ | 45.2 | 23.6 ± 1.1 | 15.7 ± 0.7 |
|  |  | $3.8 \times 10^8$ (¼)[d] | 91.3 | 10.6 ± 0.1 | 28.0 ± 0.4 |
| SD258 | $P_{cmp}$::gpl | $3.0 \times 10^8$ | 9.4 | 5.2 ± 0.6 | 17.4 ± 2.0 |
| SD252 | $P_{sbr}$::gpl | $3.5 \times 10^8$ | 13.5 | 3.1 ± 1.4 | 8.8 ± 4.1 |
| SD239 | Δslr1609::$P_{psbA2}$ 'tesA | $5.8 \times 10^8$ | 56.7 | 23.6 ± 0.02[e] | 40.7 ± 0.03[e] |
|  | Δ(slr1993-slr1994):: |  |  | 44.6 ± 2.8[f] | 76.8 ± 4.7[f] |
|  | $P_{cpc}$ accBC $P_{rbc}$ accDA |  |  | 21.0 ± 2.8[g] | 36.1 ± 4.7[g] |
|  | Δsll1951::*$P_{psbA2}$ Uc fatB1 $P_{rbc}$ Ch fatB2 |  |  |  |  |
|  | $P_{cmp}$::fol RBS shl |  |  |  |  |
| SD254 | Δslr1609::$P_{psbA2}$ 'tesA | $7.3 \times 10^8$ | 34.5 | 45.1 ± 0.4[e] | 61.7 ± 0.5[e] |
|  | Δ(slr1993-slr1994):: |  |  | 63.6 ± 0.4[f] | 87.2 ± 0.5[f] |
|  | $P_{cpc}$ accBC $P_{rbc}$ accDA |  |  | 18.6 ± 0.4[g] | 25.4 ± 0.5[g] |
|  | Δsll1951::*$P_{psbA2}$ Uc fatB1 $P_{rbc}$ Ch fatB2 |  |  |  |  |
|  | $P_{cmp}$::fol RBS shl |  |  |  |  |
|  | $P_{sbr}$::gpl |  |  |  |  |

TABLE 5-continued

Membrane damage and FFA yields of SD strains for Green Recovery

| Strain | Genetic Description[a] | Starting cell density (CFU/ml) | Membrane damage[b] (%/day) | Recovered FFA[c] (mg/L) | FFA yield ($10^{-12}$ mg/cell) |
|---|---|---|---|---|---|
| SD262 | Δslr1609::$P_{psbA2}$ 'tesA Δ(slr1993-slr1994):: $P_{cpc}$ accBC $P_{rbc}$ accDA Δsll1951::*$P_{psbA2}$ Uc fatB1 $P_{rbc}$ Ch fatB2 $P_{cmp}$::fol RBS shl $P_{sbt}$::gpl RBS 13 19 15 | $8.9 \times 10^8$ | 67.3 | $47.0 \pm 0.7^e$<br>$73.4 \pm 1.4^f$<br>$26.5 \pm 1.4^g$ | $52.8 \pm 0.8^e$<br>$82.5 \pm 1.5^f$<br>$29.7 \pm 1.5^g$ |

[a]Detailed genetic information is described in Table S1.
[b]Membrane damage was detected by SYTOX staining. The damage rates (%/day) were estimated from starting time point to the 50% permeable cell time point, when over 99.9% cells were dead. If the permeable cell percentage did not drop to 50%, the damage rates were estimated over the entire experimental period.
[c]Recovered FFAs were extracted by 10 ml hexane from 16 ml cultures after four days of $CO_2$ limitation.
[d]The data for 1/16 dilutions were similar to the data for 1/4 dilutions.
[e]The secreted FFAs before $CO_2$ limitation.
[f]Total FFAs after $CO_2$ limitation, including secreted FFAs and released FFAs.
[g]For combination strains, released FFAs were calculated by subtracting the total amount from the secreted amount.

Example 8

Green Recovery for FFAs

Figure 14:
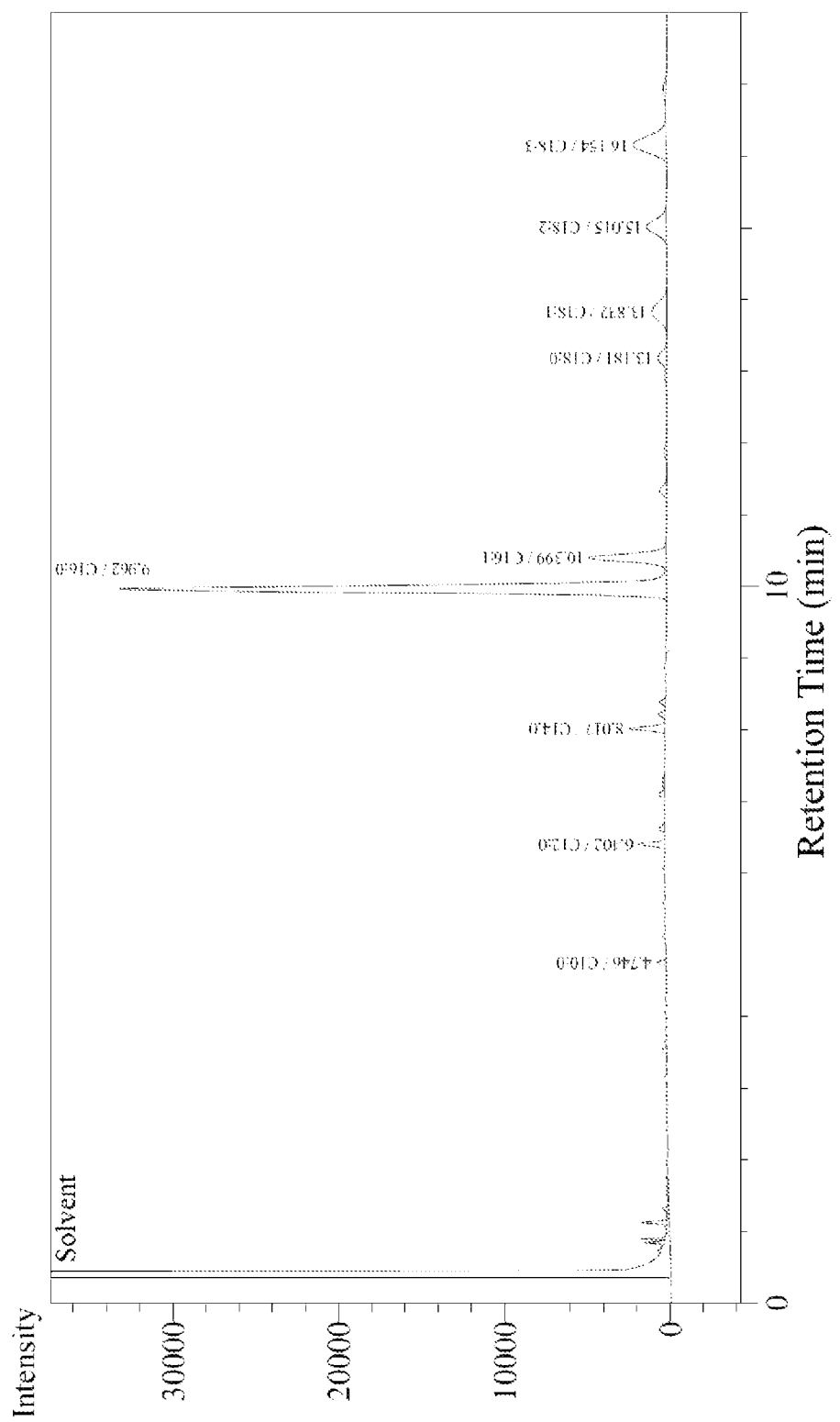
FIG. 14 depicts a gas chromatography plot of the analysis of the FFA samples extracted by hexane from the SD237 culture after $CO_2$ limitation. The retention time and the types of released FFAs are marked on the peaks.
Figure 15:
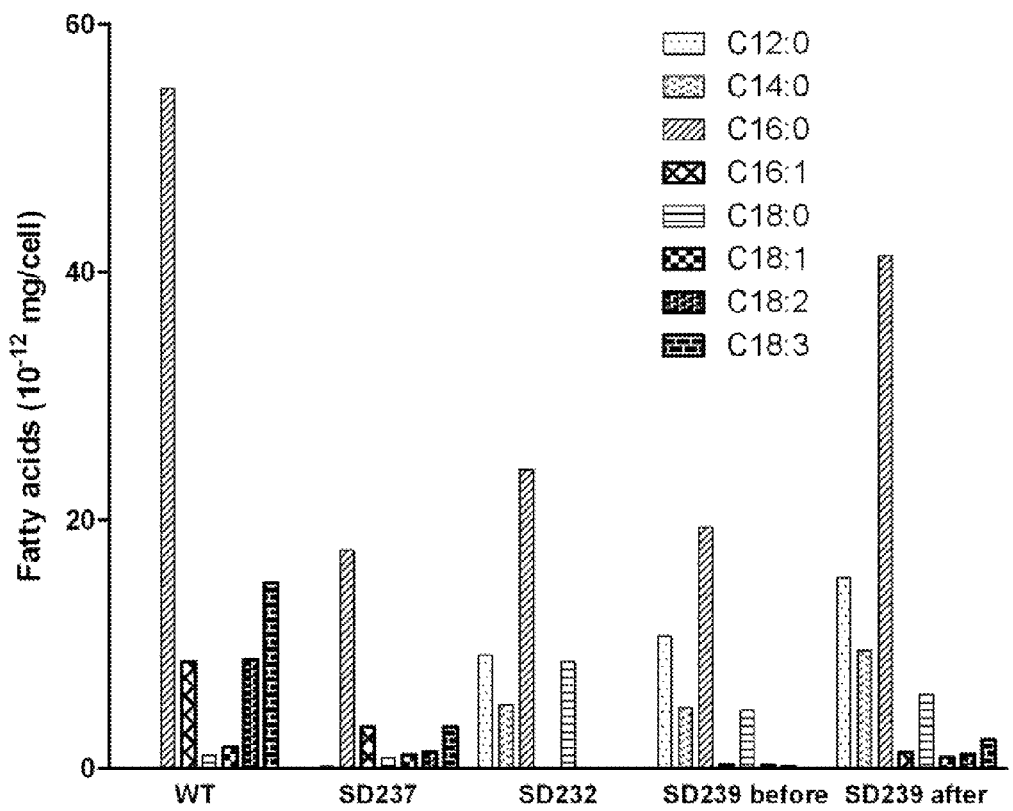
FIG. 15 depicts the fatty acid profiles of SD strains. All the cultures were grown to about $4 \times 10^8$ cells/ml at 30° C. For wild-type, the columns show the fatty acid profile of total membrane lipids. For SD237, the columns show the released FFA profile by Green Recovery, which is similar to that of wild-type with abundant unsaturated fatty acids. For SD232, the columns show the profile of secreted FFAs, which are highly saturated with significant amounts of C12:0 and C14: 0. For SD239 before (Green Recovery), the columns show the profile of secreted FFAs before $CO_2$ limitation, which is similar to that of the FFA secretion strain SD232. For SD239 after (Green Recovery), the columns show the profile of all the FFAs contributed by SD239 after $CO_2$ limitation, which is a mixture of secreted FFAs (e.g., C12:0 and C14:0) and released FFAs (e.g., C18:2 and C18:3).
Figure 16:
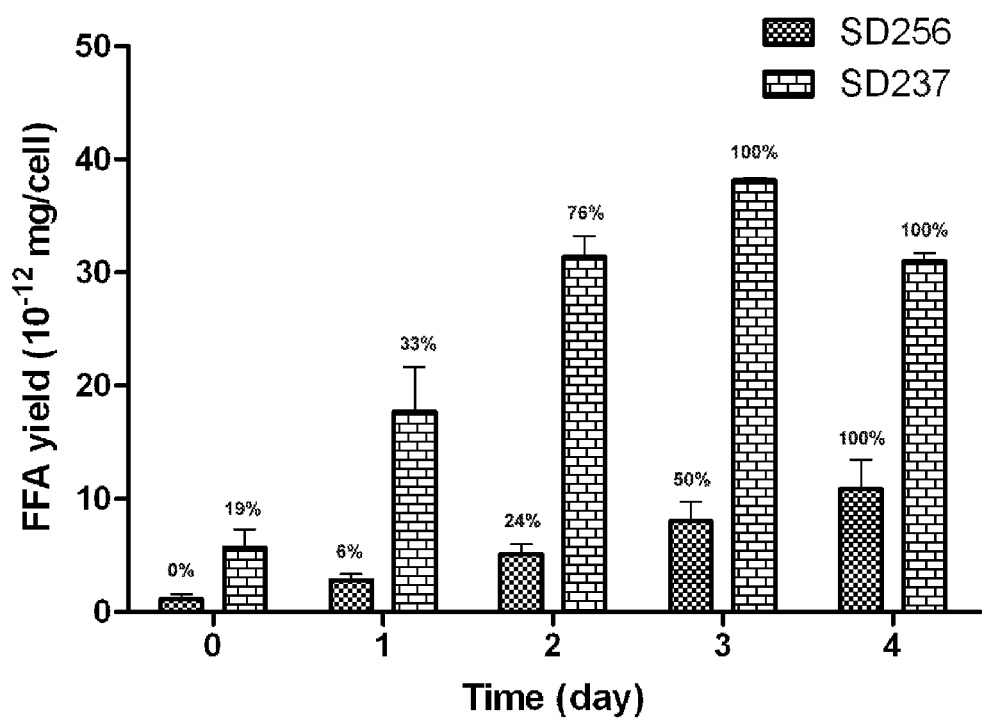
FIG. 16 depicts FFA yields of SD256 and SD237 during Green Recovery. Ten $CO_2$-limiting flasks with 16 ml cultures were set in the same conditions on day zero for each strain. Every day, the whole cultures in duplicate flasks were extracted by hexane for FFA yields. The cell membrane damage was observed after SYTOX staining, and the permeable cell percentages are indicated above the columns.

Gas Chromatography (GC) showed that a significant amount of FFAs were released by lipolytic degradation of the membrane lipids (FIG. 14 and Table 5). Green Recovery FFA yield of $36.1 \times 10^{-12}$ mg/cell were measured in SD239, compared to $200 \times 10^{-12}$ mg FFA/cell secreted by an FFA-secretion SD277 grown in the same conditions. The FFA yields of Green Recovery were closely related to the membrane damage even under different conditions (Table 5). GC also showed that the profile of the released FFA was close to the fatty acid profile of the 6803 membrane lipids with abundant unsaturated fatty acids (FIG. 15), suggesting that the released FFAs were degraded from membrane lipids. FFA release occurred concomitantly with membrane damage during Green Recovery, and the released FFA amount reached the maximum when most cells became permeable to the SYTOX stain (FIG. 16).

Example 9

Green Recovery with FFA Secretion

The FFA-secretion strains that harbor the Green Recovery system (SD239, SD254 and SD262 in Table 5) are still able to release membrane lipids as FFAs at rates faster than non-FFA-secretion strains following $CO_2$ limitation. GC analysis showed that the profile of the FFAs overproduced by acyl-ACP thioesterases by FFA-secretion strains was different from the profile of the membrane-released lipids. The FFAs recovered from overproducing strains are highly saturated and rich in C12:0 and C14:0, whereas FFAs obtained via the Green Recovery system contained substantial amounts of unsaturated fatty acids and only a small portion of C12:0 and C14:0, which is the same composition observed in membrane lipids (FIG. 15). The released FFA amount from membrane lipids is similar to the amount of secreted FFA from thioesterases (Table 5, SD239). As anticipated, the FFAs recovered from the combination strains (e.g., SD239 and SD262) after $CO_2$ limitation was a mixture of the overproduced FFAs and the released membrane FFAs.

Example 10

Application Discussions

The Green Recovery system was designed for production of scalable and cost-effective renewable biofuels in photobioreactors. Productive photobioreators require aeration systems to supply the photosynthetic microorganisms with $CO_2$. Lipid recovery from biomass by limiting $CO_2$ supply is clearly an efficient and effective method. The system we describe here does not require traditional biomass processes, such as cell harvesting, dewatering, cell disruption, solvent extraction or inducer molecules like those employed in our previous inducible cyanobacteria lysis system, thus considerably reducing the cost of lipid recovery. Since continuous agitation is not required for Green Recovery (FIG. 13), this system only needs sunlight and possibly intermittent agitation to convert biomass into FFAs. Another advantage of Green Recovery is that lipolytic enzymes convert diacylglycerols in the membranes into FFAs, which due to their low density and low solubility in water are easier to harvest and refine than the diacylglycerol lipids. Although it was reported that the guinea pig lipase Gpl had the strongest galactolipase activities ever identified, our experiment showed that Gpl was not as effective as the others in 6803 (Table 5). We speculate that the compromised performance of Gpl in 6803 was due to different lipid substrates in cyanobacteria and plants or improper protein folding of an animal protein in a cyanobacterial protein synthesis system. We anticipate that Green Recovery would provide the same advantages when applied in other microbial bioreactors such as algae, E. coli, and yeast.

Green Recovery exhibits other advantages when combined with the previously described cyanobacterial FFA secretion system. The FFA secretion system avoids the energy intensive biomass processes such as concentration and extraction by directly recovering the secreted FFA from the culture medium. However, the FFA secretion system still requires substantial biomass to achieve cost-effective FFA production, which means a significant amount of fixed carbon has to be converted and stored as lipid membranes. It is expected that the Green Recovery system will recover the membrane lipids in the potential spent cyanobacterial biomass generated by the FFA secretion system, and also will cause cell lysis and release of the unsecreted intracellular FFAs. To our surprise, incorporation of the Green Recovery system into the FFA secretion strains resulted in an increased damage rate upon $CO_2$ limitation (Table 5, SD239 and SD262). We postulate that secretion of FFAs through the cytoplamstic membranes creates some lesions in the membranes which facilitate the contact of lipolytic enzymes to the acyl glycerol ester bonds. These findings demonstrate the practical combination of the FFA-secretion system and Green Recovery in photobioreactors, where the old cultures or the spent biomass can be utilized for extra FFA yield. We believe that cyanobacterial biofuel will be instrumental in developing a carbon neutral source of sustainable fuels.

Example 11

Alkane Biosynthesis in Cyanobacteria

Figure 17:
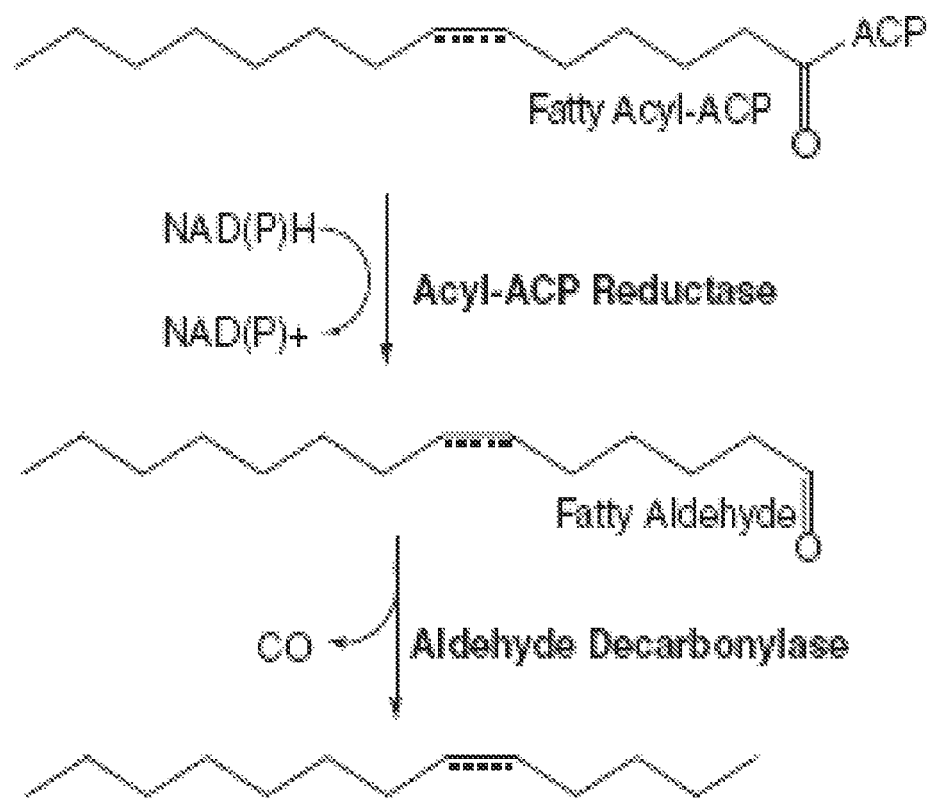
FIG. 17 depicts the alkane biosynthesis pathway in cyanobacteria.

Alkanes, the major constituents of gasoline, diesel, and jet fuel, are naturally produced by diverse species. Alkanes have been reported in a diversity of microorganisms, and the most consistent reports are from the cyanobacteria. An alkane biosynthesis pathway from cyanobacteria was well known (FIG. 17). The pathway consists of an acyl-acyl carrier protein reductase and an aldehyde decarbonylase, which together convert intermediates of fatty acid metabolism to alkanes and alkenes. The aldehyde decarbonylase is related to the broadly functional nonheme diiron enzymes. Heterologous expression of the alkane operon in *Escherichia coli* leads to the production and secretion of C13 to C17 mixtures of alkanes and alkenes. These genes and enzymes can now be leveraged for the simple and direct conversion of renewable raw materials to fungible hydrocarbon fuels.

Example 12

Alkane Genes in Cyanobacteria

Figure 18:
FIG. 18 depicts a phylogentic tree of alkane biosynthesis genes in cyanobacteria. Of these alkane biosynthesis genes, ten genes from *Synechococcus* sp. PCC 7942, *Prochlorococcus marinus* subsp. *Pastoris* str. CCMP 1986, *Nostoc punctiorme* PCC 73102, *Thermosynechococcus elongatus* BP-1, and *Gloebacter violaceus* PCC 7421, were chose for alkane overproduction in *Synechocystis* PCC sp. 6803.

With bioinformatics analysis, we found the phylogenetic relationship of the alkane production genes in cyanobacteria as shown in FIG. 18. From these alkane production genes, we chose ten alkane biosynthesis genes from five cyanobacterial species (i.e, *Synechococcus* sp. PCC 7942, *Prochlorococcus marinus* subsp. *Pastoris* str. CCMP 1986, *Nostoc punctiorme* PCC 73102, *Thermosynechococcus elongatus* BP-1, and *Gloebacter violaceus* PCC 7421) for overexpression in *Synechocystis* PCC sp. 6803. The strain constructions are listed in Table 6. Some of these alkane overproduction strains are built on the base of a Green Recovery strain such as SD237, so that they are able to release intracellular alkanes with $CO_2$ limitation.

TABLE 6

Alkane overexpression strain constructions.

| Alkane Strains | Genotype | Alkane gene sources |
|---|---|---|
| SD293 | Δsll1951-15::PpsbA210 orf1593 orf1594 | *Synechococcus* 7942 (original) |
| SD294 | Pcmp43::fol RBS shl RBS Δsll1951-15::PpsbA210 aac (7942) Ptrc adc (73102) | *Synechococcus* 7942 *Nostoc* 73102 |
| SD295 | Pcmp43::fol RBS shl RBS Δsll1951-15::PpsbA210 orf1593 orf1594 | *Synechococcus* 7942 (original) |
| SD298 | Pcmp43::fol RBS shl RBS Δ(slr1993-slr1994)-14:: PpsbA210 aac (7942) Ptrc adc (73102) | *Synechococcus* 7942 *Nostoc* 73102 |
| SD303 | Pcmp43::fol RBS shl RBS Δ(slr1993-slr1994)-14:: PpsbA210 aac (7942) Ptrc adc (73102) Δsll1951-15:: PpsbA210 orf1593 orf1594 | *Synechococcus* 7942 *Nostoc* 73102 |
| SD307 | Pcmp43::fol RBS shl RBS Δ(slr1993-slr1994)-14:: PpsbA210 aac (7942) Ptrc adc (73102) Δsll1951-15:: PpsbA210 orf1593 orf1594 Δ(slr2001-slr2002)-17::P psbA210 Ptrc aac (BP-1) Ptrc adc(BP-1) | *Synechococcus* 7942 *Nostoc* 73102 *Thermosynchococcus* BP-1 |
| SD308 | Δ(slr2001-slr2002)-17:: P psbA210 Ptrc aac (BP-1) Ptrc adc(BP-1) | *Thermosynchococcus* BP-1 |
| SD309 | Δ(slr2001-slr2002)-17::EHC1 Ptrc aac (1986) Ptrc adc(1986) | *Prochococcus* 1986 |
| SD310 | Δ(slr2001-slr2002)-17::EHC1 Ptrc aac (7421) Ptrc adc(7421) | *Gloebacter* 7421 |

Example 13

Alkane Overproduction in Genetic Modified *Synechocystis* SD Strains

Figure 19:
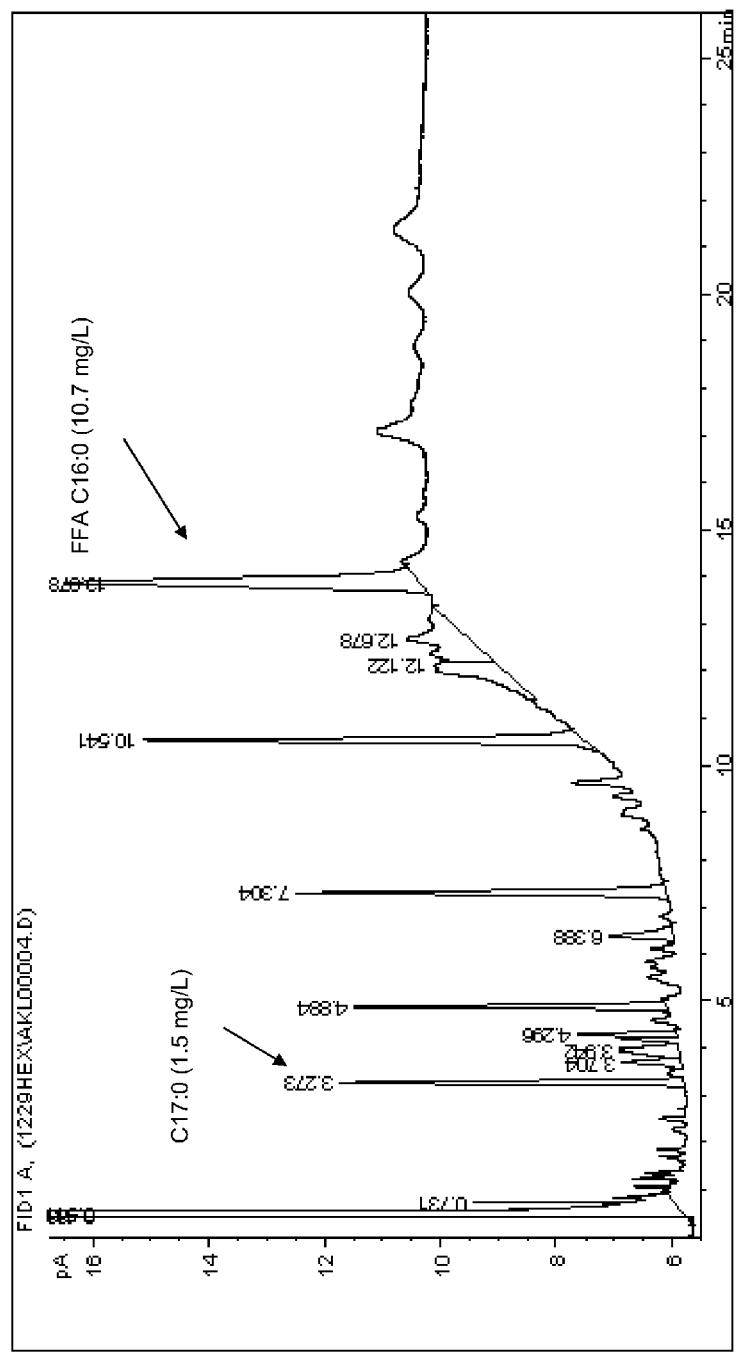
FIG. 19 depicts GC analysis of the alkane production in SD294 culture.

As shown in Table 6, nine strains were constructed for expressing the alkane biosynthesis genes from *Synechococcus* sp. PCC 7942, *Prochlorococcus marinus* subsp. *Pastoris* str. CCMP 1986, *Nostoc punctiorme* PCC 73102, *Thermosynechococcus elongatus* BP-1, and *Gloebacter violaceus* PCC 7421. Alkane biosynthesis was detected in their cultures. The GC analysis of the alkane production in SD294 culture was shown in FIG. 19, with a Heptadecane yield of 1.5 mg/L and $83.3 \times 10^{-13}$ mg/cell, which is a 55.5 fold increase from wild-type SD100 (with a yield of $1.5 \times 10^{-13}$ mg/cell) (Table 7).

TABLE 7

Alkane production in genetically modified *Synechocystis* SD strains

| Strains | WT | SD293 | SD294 | SD295 | SD298 | SD303 |
|---|---|---|---|---|---|---|
| Gene sources and modification | | Syn7942 (original) ΔS-layer | Syn7942 *Nostoc* 73102 ΔS-layer Green Recovery | Syn7942 (original) ΔS-layer Green Recovery | Syn 7942 *Nostoc* 73102 ΔPHB Green Recovery | Syn 7942 *Nostoc* 73102 ΔS-layer ΔPHB Green Recovery |
| Cell density on Day 5 (CFU 108/mL) | 6.5 | 4.3 | 1.8 | 1.4 | 1.4 | 3.0 |
| Heptadecane (C17:0) (mg/L) | 0.1 | 0.6 | 1.5 | 0.9 | 0.36 | 0.83 |
| 10-13 mg/cell | 1.5 | 14.0 | 83.3 | 64.3 | 25.7 | 27.7 |

Example 14

Alkane Overproduction with Green Recovery

Figure 20A:
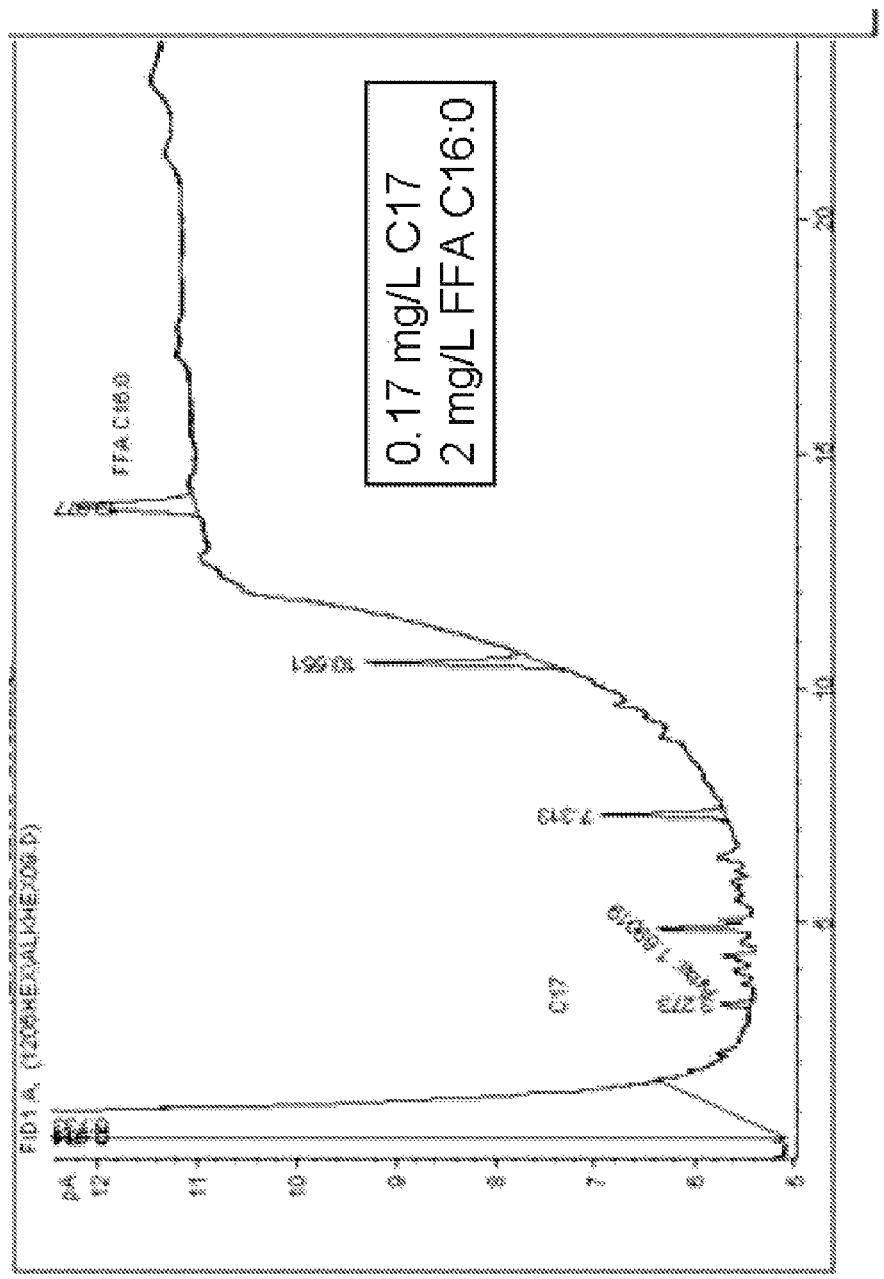
FIG. 20 depicts GC analysis of alkane production and release of alkane by Green Recovery in the SD303 culture. A, GC analysis of a culture of SD303, which has been grown for 3 day with a cell density of $3 \times 10^8$ cells/ml. B, GC analysis of the SD303 culture after Green Recovery induced by $CO_2$ limitation.
Figure 20B:
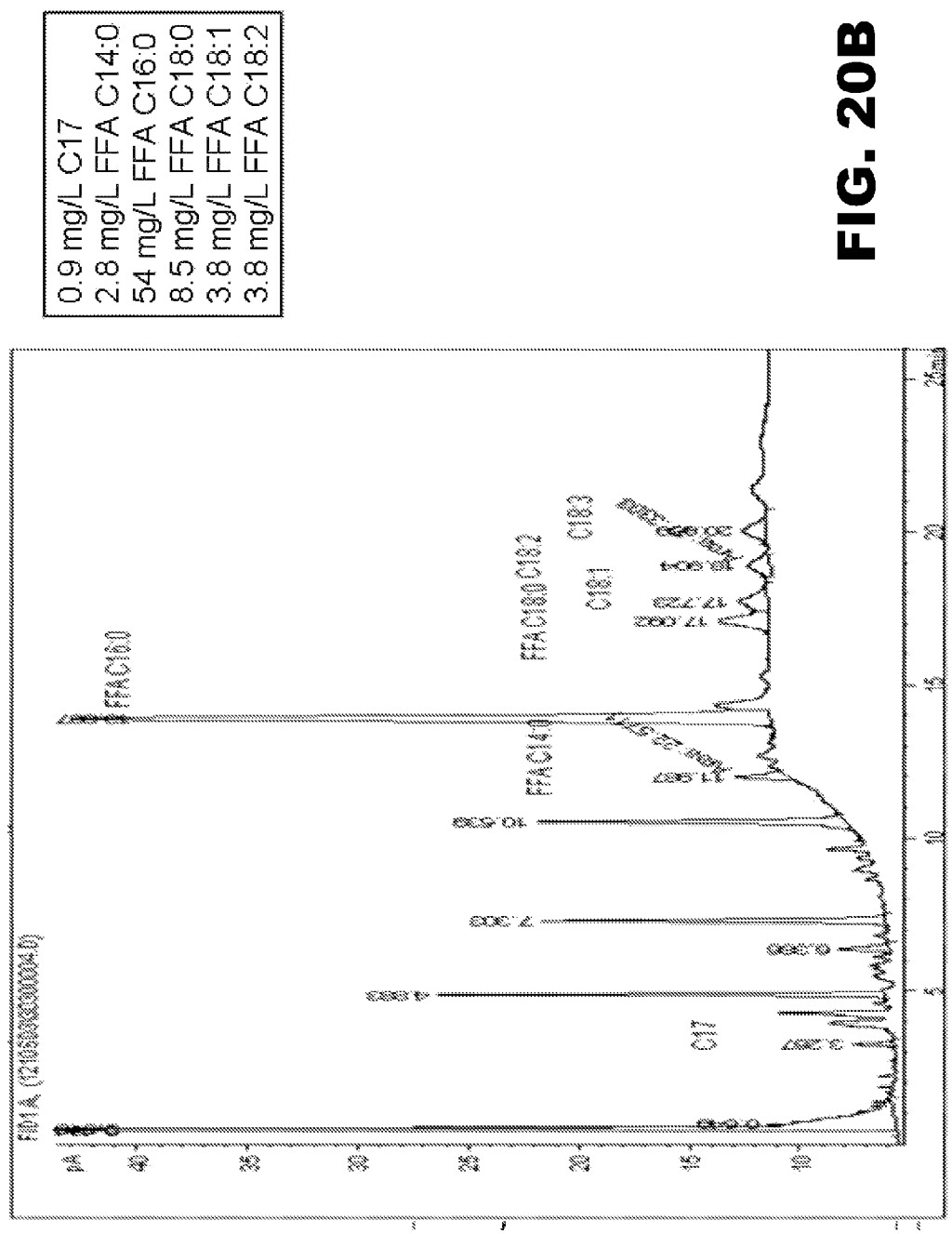

One alkane overproduction strain SD303 ($P_{cmp43}$::fol RBS shl Δ(slr1993-slr1994)-14::$P_{psbA210}$ aac $P_X$adc Δsll1951-15::$P_{psbA210}$ orf1593 orf1594) was constructed on the base of a Green Recovery strain SD237, by overexpressing the alkane biosynthesis genes from *Nostoc punctiorme* PCC 73102 and *Synechococcus* sp. PCC 7942. The experiment showed that this strain is able to produce alkanes and undergo Green Recovery when induced by $CO_2$ limitation. As shown in FIG. 20, a culture of SD303 was grown to a cell density of $3 \times 10^8$ cells/ml, GC analysis showed that 0.17 mg/L of heptadecane was detected in the culture medium. After Green Recovery induced by $CO_2$ limitation for 3 days, 0.9 mg/L of heptadecane were released into the culture medium, also a significant amount of free fatty acids were generated by Green Recovery (FIG. 20). This experiment showed that Green Recovery is able to release the alkanes which are retained inside the cell, and also to produce free fatty acids for biofuel production.

Example 15

Constructing a Stationary-Growth-Phase Autolysis System in 6803

The following example describes how to construct a stationary-growth-phase autolysis system in 6803, so that the neutral lipid cyanobacterial cells are able to autolyze for neutral lipid release when the culture enters stationary-growth-phase. This stationary-growth-phase autolysis system can also be induced to undergo cell lysis by iron starvation in the culture.

According to the microarray data by Jamie et al [Jamie S. F. et al, 2007 Arch Microbiol 187:265-279], the transcription of approximately 10% of the genes in the 6803 wild type were different in the stationary growth phase, compared to the exponential growth phase. Among the highly up-regulated genes for stationary phase, the isiA gene has its own promoter, and its iron deficiency-dependent regulation mechanism is well documented. At least three mechanisms are involved in the up regulation of the isiAB operon [Ulf, D., et al, 2006 PNAS 103:7054-7058]. (1) depression of ferric uptake regulator Fur (encoded by sll0567) on the Fur box in the promoter (+163-+186); (2) a 90 bp region upstream of the −35 box carrying a positive acting element is essential for full induction activity under iron-deplete conditions; (3) an internal antisense RNA repressor (isiR, a cis-encoded antisense RNA transcribed from the noncoding strand) is abundant under iron-replete conditions but not under iron limitation.

Figure 21:
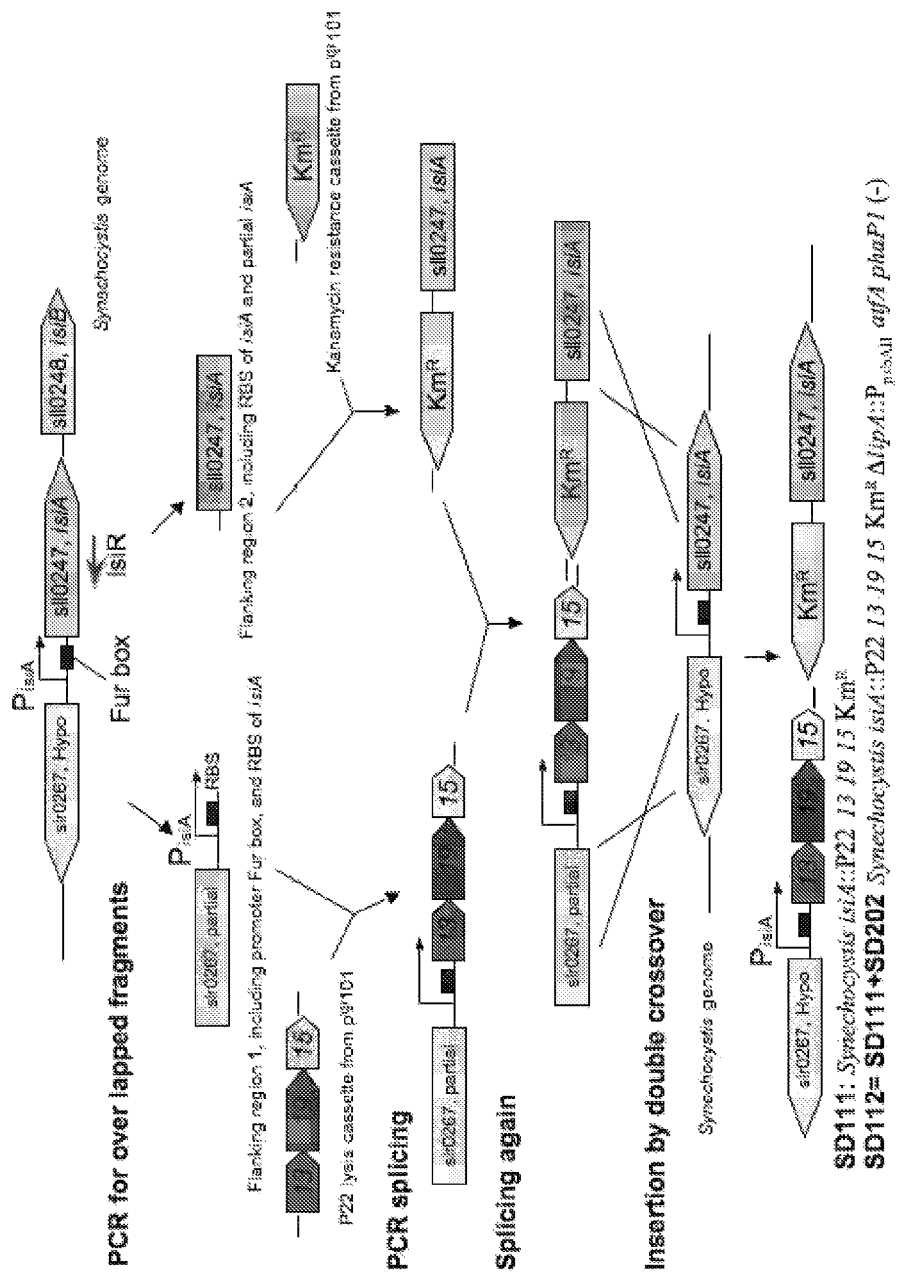
FIG. 21 depicts the construction of stationary-phase-autolysis strains SD111 and SD112. The isiA and isiB locus are shown at the top of the figure, indicated by two leftward pink arrows, which are controlled by the isiA promoter ($P_{isiA}$), Fur box (brown box), and antisense RNA (IsiR, red arrow). A DNA fragment for transformation including flanking region 1, P22 lysis cassette (13, 15, and 19), kanamycin resistance cassette ($Km^R$), and flanking region 2 are spliced together by overlapping PCR, and transferred into SD100 (6803 wild type) and SD202 (a neutral lipid production strain) by homologous double crossover exchange to result in SD111 and SD112.

The invention is to fuse the isiA promoter with the P22 lysis cassette. However, the isiA promoter is strong in *E. coli* without the repressors present in 6803, so the entire correct plasmid containing the $P_{isiA}$-P22 13 19 15 cassette is lethal after transfer to host *E. coli* cells. To avoid lethal amplification of the $P_{isiA}$-P22 13 19 15 DNA cassette in *E. coli*, DNA molecules specifying the $P_{isiA}$-P22 13 19 15 cassette to be transformed into *Synechocystis* were directly created by overlapping PCR. As shown in FIG. 21, the whole transformation unit, including flanking regions F1 and F2, the P22 lysis cassette and $Km^R$, was created by overlap PCR splicing, and transferred into SD100 (6803 wild type) and SD202 (a neutral lipid production strain) by homologous double crossover exchange to generate SD111 and SD112, respectively.

Figure 22:
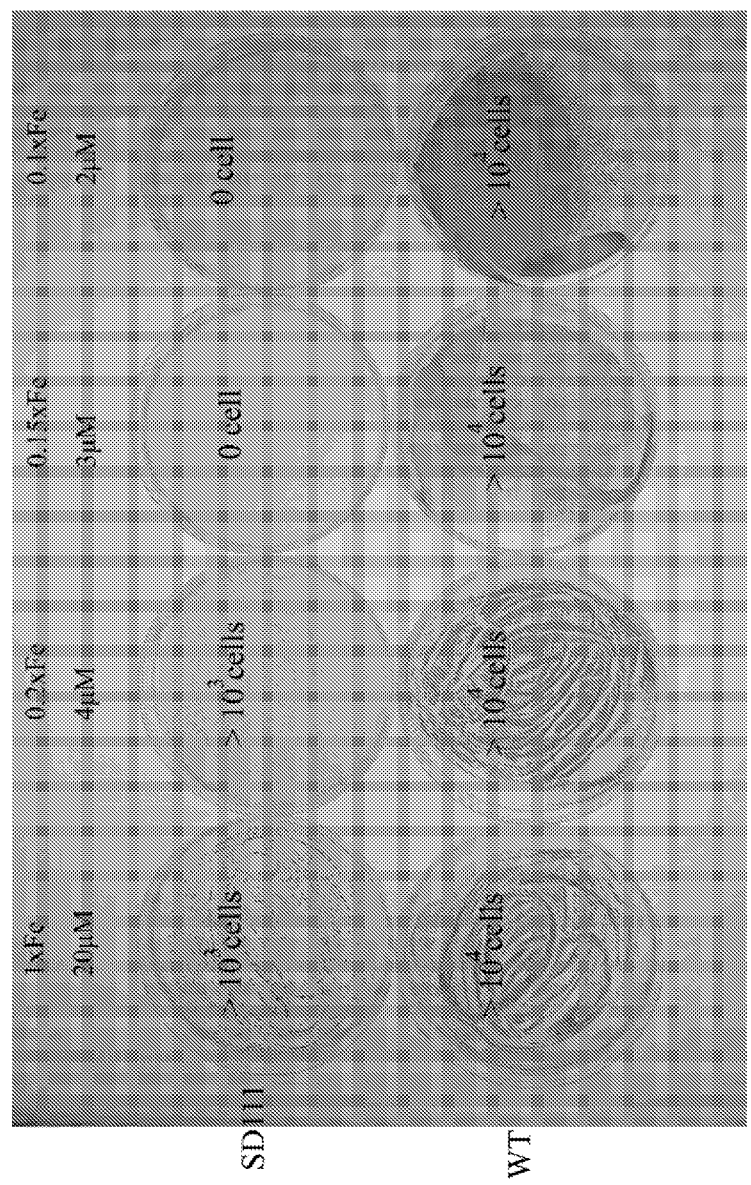
FIG. 22 depicts the autolysis response of SD111 on Fe-deficient BG-11 plates. Upper four plates, >$10^3$ SD111 6803 cells were grown on the BG11 plates containing different concentrations of Fe, i.e., 20 µM (1×Fe in BG-11), 4 µM (0.2×Fe in BG-11), 3 µM (0.15×Fe in BG-11), 2 µM (0.1×Fe in BG-11); lower four plates, >$10^4$ wild type 6803 cells were grown on the same BG-11 plates containing different concentrations of Fe.
Figure 23:
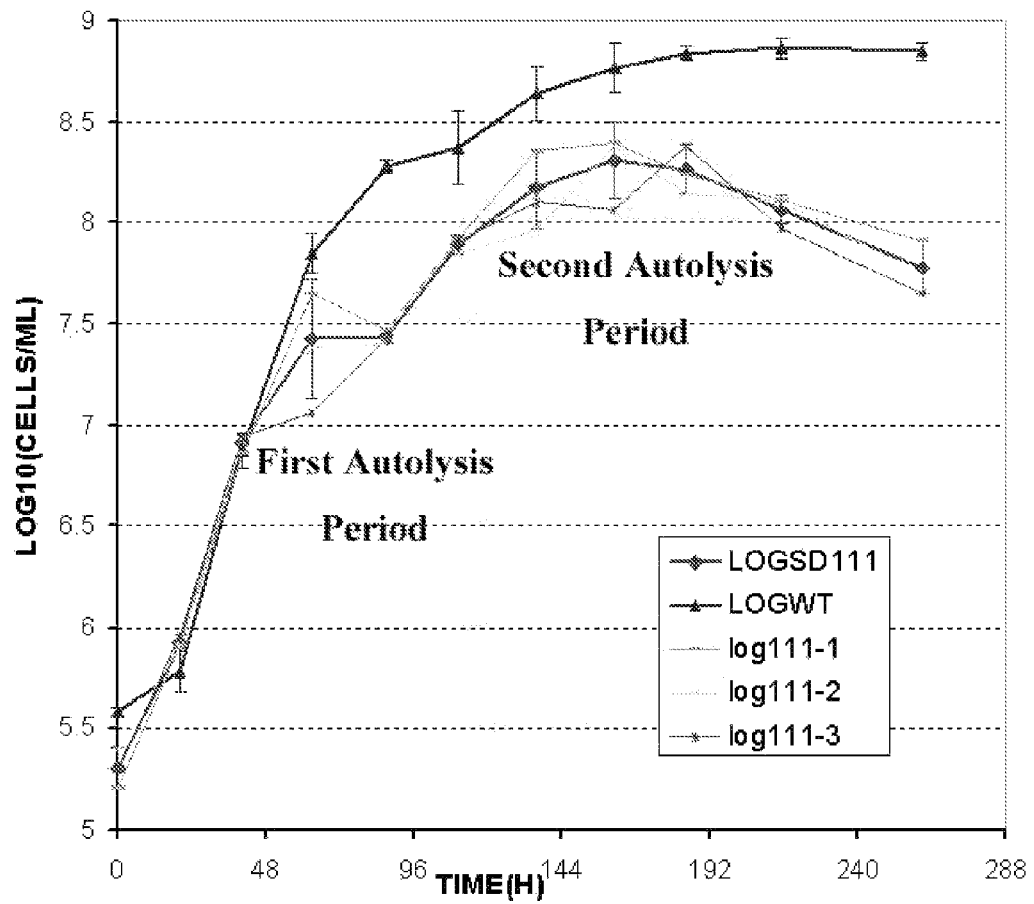
FIG. 23 depicts the Stationary-phase-autolysis of SD111 when grown in BG-11 medium. The first autolysis period is in exponential growth phase when the cell density is between $10^7$-$10^{7.5}$ cells/ml, the second autolysis period is in stationary growth phase when the cell density is above $10^8$ cells/ml. The drop and fluctuation of CFU in these two periods suggested that the old cells were undergoing self-lysis.

As shown in FIG. 22, SD111 grew normally on a BG-11 plate, grew slower on a 0.2×Fe BG-11 plate (4 µM Fe), grew into colonies and then autolysed on a 0.15×Fe BG-11 plate (3 µM Fe), but did not grow on 0.1× (and lower Fe concentration) BG-11 plates (2 µM Fe and lower). When grown in 1.0 concentration BG-11 medium, SD111 showed two autolysis periods (FIG. 23), the first autolysis period is in exponential growth phase when the cell density is between $10^7$-$10^{7.5}$ cells/ml, the second autolysis period is in stationary growth phase when the cell density is above $10^8$ cells/ml. The drop and fluctuation of CFU in these two periods suggested that the old cells were performing self-lysis. In strain SD112, the stationary-phase-autolysis is incorporated into the TAG-producing strain SD202, so that the overproduced TAGs will be released from the old lysing cells into the culture medium.

Example 16

Acyl-CoA Overproduction in Cyanobacteria

The following example describes how to increase the essential substrate for neutral lipid synthesis-acyl-CoA. The primary neutral lipid synthetase identified so far (like the WS/DGAT described above) are acyl-transferases which utilize acyl-CoA as acyl donor instead of acyl-ACP (FIG. 4). However, in cyanobacteria, the majority acyl carried molecules are acyl-ACPs instead of acyl-CoA. By increasing the acyl-CoA level, it is expected to resolve the bottleneck of neutral lipid synthesis, and thus drastically increase the yield of neutral lipid production in cyanobacteria.

Figure 24:
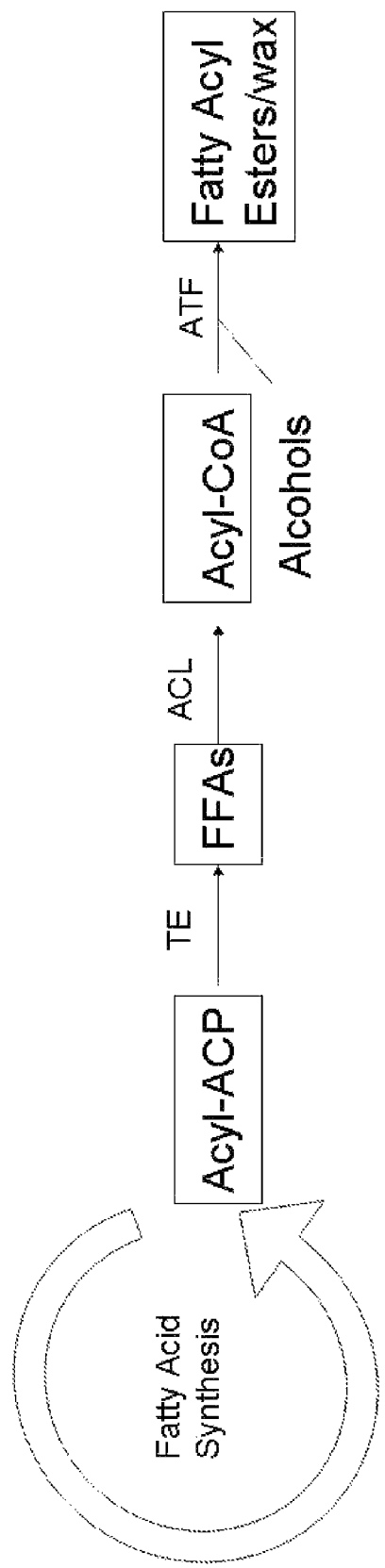
FIG. 24 depicts the biodiesel biosynthesis pathway. TE, thioesterase; ACL, acyl-CoA ligase; ATF, acyl transferase.

Acyl-CoA overproduction in cyanobacteria is based on free fatty acid overproduction. As shown in FIG. 24, the major acyl carrier molecules in cyanobacteria are acyl-ACPs, to convert acyl-ACPs into acyl-CoA, the acyl chains first need to be decoupled from acyl-ACPs as FFAs by a thioesterase (TE hereafter), and then to be activated as fatty acyl CoA by an acyl CoA ligase (ACL hereafter).

In our previous research, we have already inserted thioesterase genes from *E. coli* and plants into 6803, which resulted in the overproduction and secretion of FFAs. ACL is the first-step enzyme for the β-oxidation pathway, which ligates FFA with Coenzyme A for fatty-acyl-CoA. In *E. coli*, ACL is encoded by fadD. There are many other functional ACL genes in yeast and other heterotrophic microorganisms.

The TE genes were introduced into 6803 successively in the strains SD216, SD225, SD232, SD243, SD249 and SD277 (Table 1). Starting with SD243 and its SD247 derivative, an ACL overexpression cassette $P_{cpc45}$ fadD(Ec) is inserted to yield SD251 to overproduce acyl-CoA, where $P_{cpc45}$ is the promoter of the 6803 cpc operon, and fadD(Ec) is the fadD gene from *E. coli*. To further increase the acyl-CoA synthesis, an artificial operon $P_{psbA212}$ faa138 $P_{cpc45}$ fadD(Ec) was inserted into SD243 to result in SD273 with two ACLs. In SD273, faa138 is a synthesized gene for Faa2p from *Saccharomyces cerevisiae*, a long chain fatty acyl-CoA synthetase that accepts a wider range of acyl chain lengths than Faa1p, preferring C9:0-C13:0; involved in the activation of endogenous pools of fatty acids. fadD(Ec) is the acyl-CoA ligase from *E. coli*. The detailed strain constructions are described in Table 1.

Example 17

Biodiesel-Producing Cyanobacteria

The following example describes how to produce neutral lipids FAME and FAEE—the components of biodiesel on the basis of the acyl-CoA overproducing strains.

In our previous research, we genetically modified cyanobacterium 6803 to overproduce and secrete free fatty acids (FFA hereafter). Fatty acids are energy molecules that can be chemically converted into liquid fuels such as alkanes or fatty acyl esters. However, fatty acids cannot be used as biofuel, and an extra chemical reaction is required to convert them into lipid transportation fuels. Thus we are planning to introduce fatty acyl ester synthesis pathways into the FFA-secreting 6803 to have 6803 produce fatty acyl esters such as fatty acyl methyl ester (FAME hereafter) or fatty acyl ethyl ester (FAEE hereafter).

Biodiesel, the primary renewable alternative to diesel, is consumed at greater than 2 billion gallons per year, and is composed of FAME or FAEE derived from the chemical transesterification of plant and animal oils. FAME or FAEE can be directly used in diesel combustion engines They are chemically more stable than FFAs as they do not form fatty acid cation precipitations like FFA. FAME and FAEE are liquids at room temperature with very low solubility in water, so they are easily recovered from an aqueous photobioreactor (PBR hereafter). They are also biologically more stable than FFAs as most bacteria are able to consume FFAs through the β-oxidation pathway, but this fatty acid consuming pathway cannot degrade FAME or FAEE.

On the basis of acyl-CoA overproducing strains, SD251 and SD237 for example, another substrate for synthesis of FAME or FAEE is a short alcohol, e.g., methanol or ethanol, respectively. The biosynthesis pathway for methanol is present in some methane bacteria, but the pathway is uncommon, complicated and needs methane for the substrate. Therefore we will focus on biosynthesis of ethanol, which is simple and well studied. It is reported that exogenous expression of pyruvate decarboxylase and alcohol dehydrogenase genes will enable bacteria like cyanobacteria and *E. coli* to produce ethanol from pyruvate. At the first trial stage, we will provide the cyanobacterial cells short alcohols by adding methanol and ethanol into the culture, and we plan to introduce the ethanol pathway into 6803 later so that ethanol addition is not necessary any more.

To have 6803 produce FAME or FAEE, the whole metabolic pathway (FIG. 24) needs to be introduced into 6803. We need to introduce TE genes to uncouple FFA from acyl-ACP, to introduce and overexpress ACL genes to transfer FFA to fatty acyl-CoA, and to introduce the atfA gene to synthesize FAME or FAEE with short alcohols.

However, when we attempted to overexpress fadD and tesA ($P_{cpc}$ fadD(Ec) $P_{psbA236}$ tesA136) on the background SD202 (ΔlipA22:: Inv($P_{psbA231}$ atfA phaP)-32), no transformant colonies could be obtained. In another trial, when we attempted to add atfA and fadD ($P_{psbA244}$ atfA $P_{cpc45}$ fadD (Ec)) onto SD243 (an FFA overproduction strain), the transformation failed again as no transformant colonies grew out. These two failures seemed to suggest that these three pathway genes cannot be overexpressed in 6803 at the same time. The detailed strain constructions are described in Table 1.

To avoid the transformation difficulty, we made SD251 on the basis of SD243 (Table 1). The genotype of SD251 is Δaas-23::$P_{psbA236}$ tesA 136, Δ(slr1993-slr1994)-14::$P_{cpc39}$ accB accC70 $P_{rbc40}$ accD accA, Δsll1951-15::$P_{psbA210}$ fatB161 (Uc) $P_{rbc41}$ fatB262(Ch), Δ(slr2001-slr2002)-17:: $P_{psbA210}$ fatB262(Ch), ΔnrsBAC11::$P_{nrsB46}$ atfA $P_{cpc45}$ fadD (Ec).

In SD251, fadD(Ec) is overexpressed by promoter $P_{cpc45}$, while the atfA gene is controlled by the Ni inducible promoter $P_{nrsB46}$. This strain is successfully constructed. It is thought that with the addition of $Ni^{2+}$, the atfA gene will be turned on, and with the further addition of alcohols the induced WS/DGAT will esterify acyl-CoA with alcohol to yield FAME or FAEE.

Figure 25A:
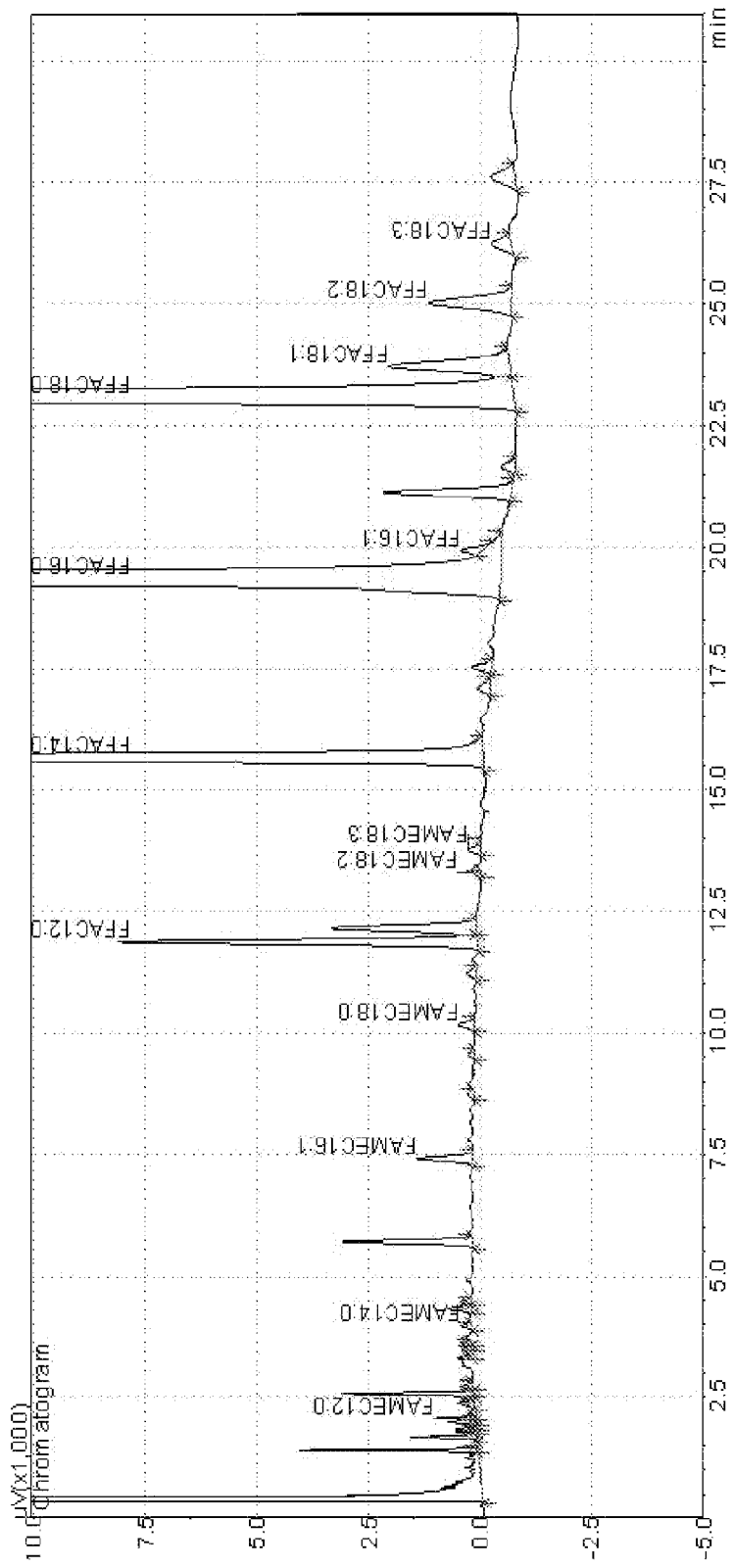
FIG. 25 depicts the GC analysis (A) of secreted FFA (B) and FAEE (C) of induced SD251 culture supplemented with ethanol.
Figure 25:
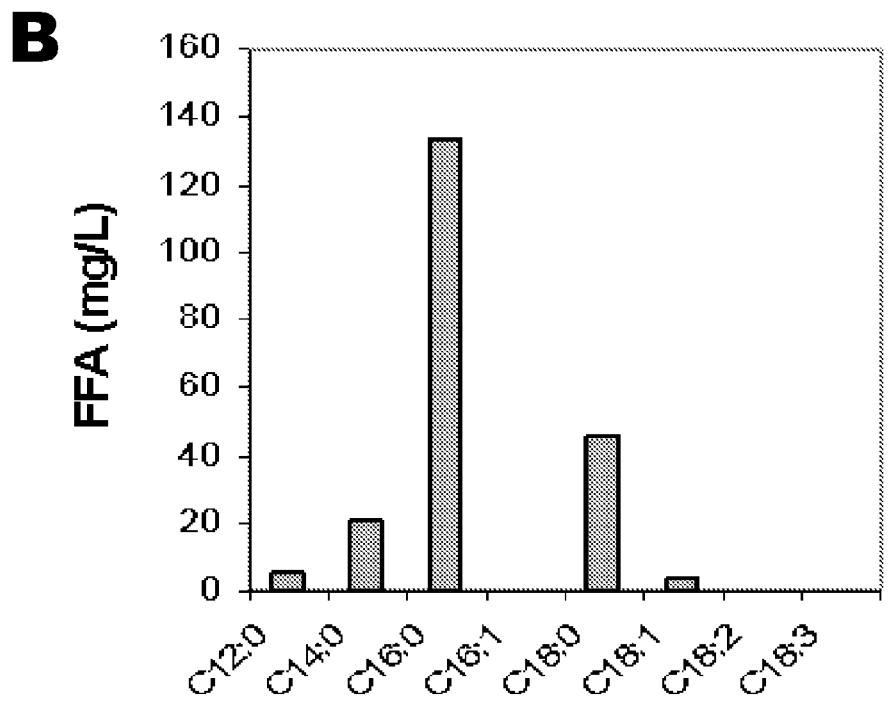
Figure 25:
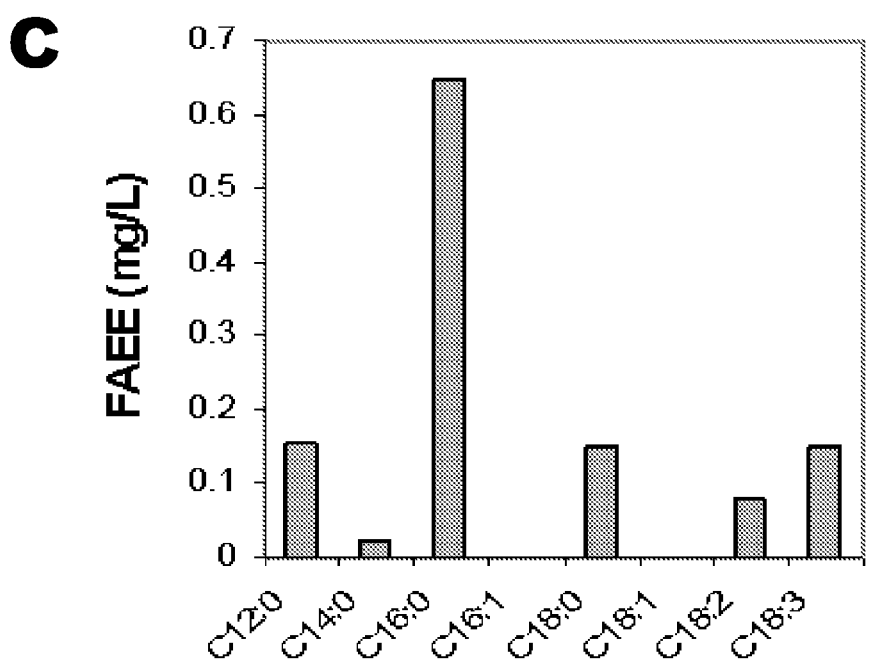

To test this idea, a 200 ml SD251 culture (~$10^{11}$ cells) was divided into five cultures of 200 ml. For aftA gene induction, 10 mM $NiSO_4$ was added. For alcohol addition, 1 ml absolute alcohol was added on the first day and 2 ml alcohol was added everyday after the first day. After 72 h about 170 ml cultures were left in the five flasks. To each whole culture, 3 g NaCl and 3 ml $H_3PO_4$ was added and the culture extracted with 20 ml acetyl acetate. After 30 min shaking (200 rpm) at 37° C., the cultures were centrifuged, and the 3 ml acetyl acetate phase was dried for GC analysis. The treatment and GC results are shown in Table 8. As an example, the GC curve for sample D is shown in FIG. 25.

The results in Table 8 show that SD251 is able to produce and secrete FAME and FAEE with nickel induction and addition of alcohols. However, the FAE secretion is only about 0.5% of that of FFA. The similar chain length pattern suggests that the FAEs are converted from the FAAs. This experiment has been performed twice with similar results each time. We tried to analyze the intracellular FAEs, but some lipids in the Folch extraction interfered with C18:3 peaks, so we have to optimize the GC methods for the intracellular FAEs.

To increase the conversion ratio of FAEs from FFAs, it is planned to increase the synthesis of ACL and WS/DGAT. Besides *E. coli* fadD, another ACL (FAA2 from yeast) gene was synthesized after codon optimization, and is being inserted into SD243. CoA is a big group, so acyl-CoA is not supposed to be easily secreted out of cells, and will accumulate inside the cells. After ACL overproduction, the atfA gene will be tested for inducible expression (e.g., by the control of $P_{isiA}$, $P_{nrsB}$, $P_{sbt}$, or $P_{cmp}$) and for constitutive expression. With the increase in acyl-CoA amount, the aftA gene can be constitutively expressed in 6803 in the presence of TEs and ACLs. In the future, the ethanol synthesis pathway will be introduced into 6803, so it will produce FAEE without addition of ethanol.

TABLE 8

FFA and FAE production of SD251 Culture with Different Treatments

| | Treatments | | | | |
|---|---|---|---|---|---|
| | A | B | C | D | E |
| Induction | None | None | 10 mM $NiSO_4$ | 10 mM $NiSO_4$ | 10 mM $NiSO_4$ |
| Alcohol | None | Methanol | None | Methanol | Ethanol |
| GC: Total secreted FFA (mg) | 6.21 | 4.72 | 5.60 | 5.39 | 5.29 |
| GC: Total secreted FAME/FAEE (mg) | 0 | 0.017 | 0.004 | 0.026 | 0.031 |
| FFA yield (mg/L/72 h) | 243.7 | 185.0 | 219.7 | 221.3 | 207.5 |
| .FAE yield (mg/L/72 h) | 0 | 0.66 | 0.15 | 1.01 | 1.20 |

Example 18

Combining Green Recovery with FAEE Production

On the basis of SD251, inserting the Green Recovery cassett $P_{cmp43}$:fol RBS shl RBS (as in SD237) will enable the resulting strain to undergo Green Recovery at $CO_2$ limitation.

The resulting strain will produce FAME/FAEE with induction by Ni and addition of methanol or ethanol (as in SD251), and will undergo Green Recovery to release intracellular FAME/FAEE when the culture is limited for $CO_2$, also Green Recovery will convert about 50% membrane lipids into free fatty acids for biofuel production (as in SD237).

Example 19

Bacterial Strains, Culture Media and Growth Conditions

All SD strains are derived from *Synechocystis* sp. PCC 6803 and listed in Table 1. SD strains were grown at 30° C. in modified BG-11 medium (34) under continuous illumination (50 µmol photons $m^{-2}$ $s^{-1}$) and bubbled with 1% $CO_2$-enriched air. The details for growing an SD culture from a colony descended from a single cell are described in Example 12. For plating and transformant selection, 50 µg/mL kanamycin or 4.5% (w/v) sucrose is added to 1.5% agar plates (w/v). All of our strains are maintained as concentrated cultures in BG-11 medium with 20% glycerol and stored at –80° C.

Example 20

Genetic Manipulation for Cyanobacterium 6803

Methods for DNA manipulation are standard. The primers for constructions and genotype verifications are listed in Table 9. DNA sequences were analyzed in the DNA Sequence Laboratory at Arizona State University. Gene segments are synthesized at Genscript (Piscataway, N.J., USA). The nucleic acid sequences of non-6803 genes were redesigned by codon optimization based on the codon frequencies of highly expressed 6803 genes (Table 10). Also stem-loop hairpins in the predicted mRNA secondary structure were removed to smooth the transcription and to stabilize mRNA by prolonging its half-life. Multiple gene modifications are applied into SD strains by using a sacB-$Km^R$ cassette.

We optimized the current genetic modification techniques for 6803 gene deletion, insertion and substitution. Suicide vectors harboring a positive selection marker (e.g., $Km^R$) and a counter selection marker (e.g., sacB) are widely applied in a two-step gene deletion and insertion for 6803 without leaving any drug marker residuals.

i. Transformation of Suicide Vectors Containing sacB-$Km^R$ Cassette.

About $10^6$ SD cells in 10 µl BG-11 medium are mixed with 400 ng suicide vector DNA containing the sacB-$Km^R$ cassette and incubated for 5 h. Then the mixtures were plated onto a filter membrane (Whatman PC MB 90MM 0.4 µm) layered on a BG-11 agar plate. After segregation on the BG-11 plate for about 24 h, the membrane carrying the cyanobacteria was transferred onto a BG-11 plate containing 50 µg/mL of kanamycin. Generally, the colonies appear 4-5 days later. Individual colonies are restreaked with a sterile loop onto a kanamycin BG-11 agar plate and a 4.5% sucrose BG-11 agar plate. Those patches growing on a kanamycin BG-11 agar plate and not growing on a 4.5% sucrose BG-11 agar plate have the correct insertions with the sacB-$Km^R$ cassette.

ii. Transformation with Markerless Constructs.

To replace the sacB-$Km^R$ selective marker with target gene segments, about $10^6$ sacB-$Km^R$ cells in 10 µl BG-11 medium are mixed with 400 ng suicide vector DNA containing the target genes and incubated for 5 h. The mixtures are inoculated into 2 mL buffered BG-11 medium and grown for 3-4 days. 1 mL inoculation is plated onto a 4.5% sucrose-containing BG-11 agar plate. Generally, the colonies appear 5-8 days later. Individual colonies are restreaked onto a kanamycin BG-11 agar plates and a 4.5% sucrose BG-11 agar plates. The patches growing on sucrose plates and not growing on kanamycin plates are positive candidates for further evaluation by PCR.

iii. Confirmation of Replacement.

Cells from a colony are resuspended in 2 µl water in a 200 µl PCR tube. The cell suspension is frozen at –80° C. for 2 min, and then thawed in a 60° C. water bath. This freeze-thaw cycle needs to be performed three times. 1 µl frozen-thawed cell suspension is used as the PCR template for a 30 µl PCR reaction including the primers specific for the inserted gene segments or the deleted region.

When a foreign gene is introduced into 6803, it may cause adverse effect on the growth and be subjected to gene loss or modification, since any cell losing the genetic alteration will likely have a higher growth rate to eventually take over the population. The genetic stability of foreign genes in 6803 is therefore tested by growing a culture of the strain with periodic dilution and subculturing for at least two months. After this time, the cells from the culture are plated onto BG-11 agar plates to obtain single isolated colonies. One hundred single colonies are picked and tested for all genetic attributes and confirmed for the presence of the foreign gene by PCR as described above. The percentage of positive colonies in the culture reflects the genetic stability of the foreign gene. Genes found to be unstable can be modified to eliminate non-functional hydrophobic domains that often are responsible for poor growth due to association with and impairment of lipid membranes function.

TABLE 9

| Primers used in this study | |
|---|---|
| Primer Name | Sequences (5' to 3') |
| consturction of pψ101 | |
| SynL-S-SacI | GCgAgcTcCAGACGACTACGGGCAAAG |
| SynL-A-to-P22 | ATGTTTTTCTGGCATCACACCACCTCAAATTGGG |
| P22-S-to-SynL | TTGAGGTGGTGTGATGCCAGAAAAACATGATCT |
| P22-A-SacII | gaccGcGGTTATTTTAAGCACTGACTCC |
| KR-S-SacII(-) | GGccGcGGAAAGCCACGTTGTGTCTCA |
| KR(-)-A-to-Syn | ACCCCCTGGGGCAGAAAGCCACGTTGTGTCTCA |
| SynR-S-to-KR(-) | ACAACGTGGCTTTCTGCCCCAGGGGGTTTCTTGA |
| SynR-A-BamHI | GGgAtcCGTTGGTTAGCCAAGAGAATC |

TABLE 9-continued

Primers used in this study

| Primer Name | Sequences (5' to 3') |
|---|---| consturction of pψ102

| P2213-A-NdeI | GACATATGTTACTGCTGATTTGCATCATCGA |
| SynR-S-XbaI | gaTCTAGACACATTGCTCCTTTTGTGCGTAA |
| SynR-A-SacII | gaCCGCGGAACTAATGGCTTGGGCTAGGTATA |

Consturction of pψ121

| SynL-S-KpnI | GAGGTACCGCCAATTGCAGACGACTACG |
| SynR-S-XbaI | GATCTAGACACATTGCTCCTTTTGTGCGTAA |
| SynR-A-SacII | GACCGCGGAACTAATGGCTTGGGCTAGGTATA |
| Syn-right-A-SphI | aGGCAtgCGTTGGTTAGCCAAGAGA |
| P22-A-to-F1 | GCACAAAAGGAGCAATGTGttattttaagcactgactcc |
| F1-S-to-P22 | tcagtgcttaaaataaCACATTGCTCCTTTTGTGCG |
| SynR-A-F2 | CAAACTAATGGCTTGGGCTAGGTATAGCT |

Consturction of pψ122

| F1-A-to-LMD | catgttttctggCATCACACCACCTCAAATTGGG |
| LMD-S-to-F1 | AGGTGGTGTGATGccagaaaaacatgacct |
| LMD-A-to-F2 | ACAAAAGGAGCAATGTGctatctgcactgctcattaata |
| F2-S-to-LMD | agtgcagatagCACATTGCTCCTTTTGTGCGT |
| SynR-A-SacII | gaCCGCGGAACTAATGGCTTGGGCTAGGTATA |

Consturction of pψ123 and pψ124

| tP4-S | atCATATGaagacaaacgaaagcccccacctagcgtcatgccgggtgggggcttttttcatCTGCAGta |
| tP4-A | TACTGCAGATGAAAAAGCCCCCACCCGGCATGACGCTAGGTGGGGGCTTTCGTTTGTCTTCATATGAT |
| tP4-A-PstI | CTGCAGATGAAAAAGCCCCCACC |
| pA2-S-BamHI | gaGGATCCTAATTGTATGCCCGACTATT |
| pA2-A-to-P2219 | actgctgatttgcatCATTTGGTTATAATTCCTTATG |
| P2219-S-to-pA2 | GAATTATAACCAAATGatgcaaatcagcagtaacgg |
| P2215-A-BamHI | gaGGATCCttattttaagcactgactcct |
| lambdaS-NdeI | gaCATATGccagaaaaacatgacctgt |

Construction of pψ126

| S2F1-S-HindIII | AGaagcTTTGTGGCCCAACAATTGGT |
| S2F2-A-EcoRI | GTGAAtTCTGTAAGCAGTTAGAGTGGCCC |
| S2-segS-400 | CGGTCTACTCCGGTTAAATCCCCTAACG |
| S2-segA-400 | CCACAGCCCCAACAATAAGCAAGAT |

Construction of pψ127

| lambdaS-S-NdeI | gaCATATGccagaaaaacatgacctgt |
| lambdaS-S-NdeI-RBS | gaCATATGaggaGGTGTGatgccagaaaaacatgacc |
| pA2-A-to-R | actgctgatttgcatCATTTGGTTATAATTCCTTATG |
| R-S-to-pA2 | GAATTATAACCAAATGatgcaaatcagcagtaacgg |

Construction of pΨ214

| FadD-F1-A | TAA ACT CTG TAG GCC AGC GGC AA |
| FadD-F1-S | CGT CAA TGC CTA GAC CTA GCA GTA CC |
| FadD-F2-S | AAG GAT TTC CGT TTT ATC CCA GCA CCA |
| FadD-F2-A | GTA ATT GCC ACA GAC AAG CGT ATT CGG |
| KS-NdeI | ACC ATA TGC ATC CTA GGC CTA TTA ATA TTC CGG |
| KS-BamHI | GAA TTA GGA TCC GTC GAC CTG CAG G |

Construction of pΨ215

| NiF1-S-EcoRI | GA<u>gAA TTc</u> CAG ACG ACT ACG GGC AAA G |
| NiF1-A-toTesA | AAC GTG TCC GCC ATC ACA CCA CCT CAA ATT G |
| TesA-S-toNiF1 | GAG GTG GTG TGA TGG CGG ACA CGT TAT GAT |
| TesA-A-toNiF2 | CAA AAG GAG CAA TGT GTT ATT TGT CAT CAT CGT CTT |
| NiF2-S-toTesA | GAT GAT GAC AAA TAA CAC ATT GCT CCT TTT GTG CG |
| NiF2-A-BamHI | AC<u>G GAT CCG</u> CAA GCA GTG AAA GAT AG |

TABLE 9-continued

Primers used in this study

| Primer Name | Sequences (5' to 3') |
|---|---|

Construction of pΨ216

| | |
|---|---|
| TesA-S | CAA<u>ATG</u>GCGGACACGTTATTGATTCTG |
| TesA-A | CTT TGT AGT CTG AGT CAT GAT TTA CTA AAG GCT G |
| Test-S-to-pA2 | ATTATAACCAA<u>ATG</u>GCGGACACGTTA |
| pA2-S | TCCCCATTGCCCCAAAATACATCC |
| pA2-A-to-TesA | CAA TAA CGT GTC CGC CAT TTG GTT ATA ATT CCT TA |

Construction of pΨ207

| | |
|---|---|
| S4F1-S-PstI | GA<u>ctgc</u>AGGTCATTGCCGATAAAGTTG |
| S4F1-A-XbaI | AG<u>tctag</u>ATAATGTACAGGTCAAGCTGGTCT |
| S4F2-S-SacI | GA<u>gagc</u>TCATTGCACCGAAATGACTTTGG |
| S4F2-A-EcoRI | GA<u>GAATTC</u>TTTGCATTTCCGAAACCACCC |
| S4F2-S-XbaI | GA<u>TCTAGA</u>ATTGACACCGAAATGACTTTGG |
| S4F2-A-KpnI | GA<u>GGTACC</u>TTTGCATTTCCGAAACCACCC |

Construction of pΨ223

| | |
|---|---|
| Pcpc-S | TAG GCT GTG GTT CCC TAG GCA ACA GT |
| Pcpc-A-to-SynB | TCC GTA AAG TTA ATA GCC ATT GAA TTA ATC TCC TAC TTG AC |
| SynB-S-to-Pcpc | AGG AGA TTA ATT CAA TGG CTA TTA ACT TTA CGG AAC TGC G |
| SynB-A-to-SynC | CAT TGA ATT AAT CTC CTC TAG GGT TTA ATC CAC ATT AGG GTT |
| SynC-S | CCT AGA GGA GAT TAA TTC AAT GCA ATT CGC CAA AAT TTT AAT TGC |
| SynC-A | CTC TCC ATT GAC CTA GGG TGT AAA TGC TTC G |
| SynC-S-to-SynB | GTG GAT AAA CCC CTA GAG GAG ATT AAT TCA ATG CAA TTC GC |
| SynC-A-to-Prbc | CTT TAC TTA TGG CAA TGC TCT CCA TTG ACC TAG GGT GTT |
| Prbc-S | AAC ACC CTA GGT CAA TGG AGA GCA TTG CCA T |
| Prbc-A-to-SynD | CAA TCA AAT AGA GAC ATC TAG GTC AGT CCT CCA TAA AC |
| SynD-S-to-Prbc | AGG ACT GAC CTA GAT GTC TCT ATT GAT TGG TT TGC C |
| SynD-A-to-SynA | AGT CCT CCT TAA CCA TCT GAT TGA CGA AAT |
| SynA-S | GAC CTA GAT GAG TAA AAG TGA GCG TCG TGT TTT TCT |
| SynA-S-to-SynD | TCA AGA TGG TTA AGG AGG ACT GAC CTA GAT GAG TAA AAG TGA |
| SynA-A | TCA TTA CAC CGC CGT TTC TAA AAA TTG ACC CAA ATG |
| SynB-S-Seq | CCT TCG GCC ATC AAG AGA ATG CAG AG |
| SynA-A-Seq | TGA CGC AAC TGT TCA GCC CGA CT |

Construction of pΨ228

| | |
|---|---|
| S5F1S | CAC CAC TTT ACC ATG ACG GAA GGT GG |
| S5F1A | TGT CTC GGA GTT GCT AGG GTA ATC ATC AGC A |
| S5F2S | TCG CGA ATT CCT GTT CAT CAA CAA CGG TG |
| S5F2A | AAA GCT AAA GCG ACT GAG GAA GTG CCA G |

Construction of pΨ231

| | |
|---|---|
| Fats-S | AGA TAT CGC GTG CAA GGC CCA GTG |
| Fats-A | TGA TAT CAT TAA GAG ACC GAG TTT CCA TTG G |

Construction of pΨ240

| | |
|---|---|
| S7F1-S | GAC TTC CAA AAC GGC GAT CAA GCC AAC C |
| S7F1-A | GTC CAT TAG GGG AGT GTC CGC CAA CA |
| S7F2-S | GGT ACC ATG CAC TGG TGG ATT ACG CC |
| S7F2-A | GGG AAA TTG TTC CGT AAA CTG TTG ATA TTC CCG GT |

Construction of pΨ243

| | |
|---|---|
| ChFatB-s-to-Psba | CTG AAC GAA GGA ATT ATA ACC AAA TGG TGG CTG CTG CTG CTA GTT C |
| PsbA-a-to-ChFatB | GAA CTA GCA GCA GCA GCC ACC ATT TGG TTA TAA TTC CTT CGT TCA G |

TABLE 9-continued

Primers used in this study

| Primer Name | Sequences (5' to 3') |
|---|---|

Construction of pΨ248

| | |
|---|---|
| S9F1S | CAA TAG GAT TCG TAG AGA TTG AGA TAC TCC ATG GCG T |
| S9F1A | AGC CTT TTT TGA GGG CTA CCT TTT GGC TGT T |
| S9F2S | GGC TCC CTA CTT TTA CGG TTA CAT TTT TGG CGA AT |
| S9F2A | CTA CAA GGA AGC AAT TTG TCG CAT ATA TTG ACC CCA A |

Construction of Alkane strains

| | |
|---|---|
| EHC1S | GAT ATC GTT CGT TAA TTT TTC CCA TCG CTT TTA G |
| EHC1A | GAT ATC TAA ACT TAG TCT AAG GAT TAA TGA GAG T |
| EHC2S | ATG ATA TCT GTA ATT TCG TCG AGT CCC AGC CA |
| EHC2A | TTG TTT CTC CTC TTT AAA ATT ATA CGA GCC GGA T |
| BP-1-S | AAA TGT TCG GTT TAA TCG GCC ATC TGA CTA GC |
| BP-1-A | TCT TAG GCA CCA GTC AGC CCA TAA ACA GAC A |
| Pro1986-S | ATG TTT GGT TTG ATT GGG CAC TCT ACT AGT TTC G |
| Pro1986-A | TCT TAG GCA CCA GTC AGC CCA TAA ACA |
| Glo7124-S | AAA TGT TCG GTC TGA TCG GGC ACC TC |
| Glo7124-A | ATA TCT TAT TGG CGG GGA GCA CTG GC |
| aar-A | CCA AAT GAA ATT TGG TTT AAT TGG TCA TCT CAC TAG |
| 1593-s-to-pA2 | AAG GAA TTA TAA CCA AAT GCC GCA GCT TGA AGC CAG CCT T |
| pA2-a-to-1593 | TTC AAG CTG CGG CAT TTG GTT ATA ATT CCT TCG TTC AGA TT |
| 1594-A | TCA AAT TGC AAA TGC AAA GGG TTG GAA GC |
| ADC-A | CTG ATA TCT AAA GCA CCG ATC AAC CCG TAG GCA CT |

Segregation Checking/Sequencing

| | |
|---|---|
| FadD-F2-Seq | ATA AGT TTG GGT TAC CAC TGG TCG TTT GAG CTT C |
| FadD-F1-Sequ | CTTCCCTTCTTCCTTCCATCTGATTATGGT |
| S4-seg100-S | TGGCTCCCTGACCAATTTTTCGG |
| S4-seg100-A | CCA GGC AAT TTC CTC CGG TTT ACC |
| S5100S | TCA TCG TGT AAA CAG CGG TAT GCT TCT AGT CT |
| S5100A | CAA AGG TAC CGC TAA TAC CTG TAA GTT CTA CGA GG |
| S7 Seg 51S | GGG GAT CAA TTG CGT CTC TGT GGC |
| S7 Seg 90A | CAA AGC GTT GAC CGT GCC AGT TTT TGA C |
| S9-S68 | CCC TAA AAA AAG TCA AAC TAA CCT TTC CCA GGG TGG |
| S9-A71 | CTT CTT TGG CCA CAT CTT CGC CTA GTA AAT GGT T |

TABLE 10

Synthesized DNA segments

P<sub>rbc34</sub> aftA69 RBS pha-68

TTGGCGGGTGTCGGGCTGGCTTAACTATGCGGCATCAGGCAGATTGTACTGAGAGTGCACCATATG

AGAATTCCGGATATCTAGAAGCTT

CAACGGCTCACAAGCCCAACTAATCACCATTTGGACAAAACATCAGtAATTCTAATTAGAAAGTCC

AAAAATTGTAATTTAAAAAACAGTCAATGGAGAGCATTGCCATAAGTAAAGGCATCCCCTGCGTGA

TAAGATTACCTTCAGAAAACAGATAGTTGCTGGGTTATCGCAGATTTTTCTCGCAACCAAATAACT

GTAAATAATAACTGTCTCTGGGGCGACGGTAGGCTTTATATTGCCAAATTTCGCCCGTGGGAGAAA

GCTAGGCTATTCAATGTTTATGGAGGACTGACCTAG atg cgT CCt tta CAC ccg att gat TTC ATc ttT ctg TCC ttG gaG aaa CGt caa caA ccC atg cat gta GGC GGC tta TTC ttg TTC cag att cct gat aac gcc CCC gac acC TTC att caa gat ctg gtg aat gaC atc cgC ATc TCC aaa TCC atT cct GTG CCC CCc ttT aac aat aaa ctg aaC ggT CTG TTC tgg gaT TABLE 10-continued Synthesized DNA segments gaG gaT gaG gag ttt gaC tta gat CAC caC ttt cgC CAC att GCC ctg ccC
caC cct GGC cgT atT cgG gaa tta tTa att tat atC agC caa gaA cac agt
acg ctg CTg gaC cgC GCt aag ccc ttg tgg acc tgT aaC att atC gaa ggC
att gaa ggc aat cgt TTC gcc atg tac ttc aaa att caC CAt gcg atg gtc
gat ggC GTc GCC GGt atg cgC CTg att gaa aaG TCC ctc tcc cat gat gta
ACC gaa aaa agt atc gtg CCC ccC tgg TGC GTG gaA ggC aaa cgG GCt aag
cgc tta CGG gaa cct aaa ACt ggt aaa att aag aaa atc atg tct ggt att
aaA agT cag CTG caA gcg ACC ccc ACC gtc att caa gaA CTc tcC caA ACC
gta TTC aaa gat att ggC cgt aat cct gat CAC GTG TCC agc ttt cag gcg
cct TGC tct att ttg aat cag cgt gtg agT TCC TCC CGG cgt ttt GCC GCg
caA Agt ttt gac CTG gat cgt ttt cgt aat att gcc aaa TCC ttg aaC gtC
acc att aaC gat GTG gta CTG gcg gta TGC tct ggt GCC tta cgt gcg tat
ttg atg Tcc caC aat tCC Ctg cct TCC aaa CCC tta att gcT atg GTG CCC
gcc tct atC cgG aaC gaT gaC TCC gaC gtc agc aac cgt att acg atg att
ctC GCg aat ttg GCC acc cac aaa gat gat cct tta caa cgt CTc gaa att
atc cgc cgt TCt GTG caa aac TCC aag caa cgc ttc aaa cgt atg acT agc
gaC caA att CTc aat tat agt GCt gtG gta tat ggT cct GCC ggC ctc aac
ATT att tct ggc atg atg CCC aaa cgc caa gcc ttc aat ctC GTG atC AGc
aat gtT ccC ggT CCC CGc gag CCC CTG tac tgg aat GGC gcc aaa CTG gat
GCC ctc tac CCC GCC TCC att gta tta gac ggt caG GCC ttg aat att ACC
atg acT tCt taC tta gat aaa TTg gaG cTc GGt ttg att GCT tgT cgt aat
GCC ttg CCC CGG atg cag aat tta ctg ACC CAC tta gaa gaa gaa att caa
CTc TTC gaa ggT gta att GCg aag cag gaa gat att aaa ACt gcG aat taa
GGAGGAATTAAA aTG ATc ctG acc ccC gaG caa gtG GCT GCT gcg caa AAA GCT AAT ctc gaa
acC ctg TTc GGT ctg acc acT AAA gcC ttC gaG GGT gtG gaa AAA ctc gtG
GAA ctC AAT ctC cag gtc gtG AAA act TCC TTT GCT gaa GGT gtt GAT AAT
GCc AAA AAA gcC ctC TCC GCT AAA GAT GCT caA gaa ctg ctC GCT ATc caA
GCc GCT GCT GTT cag ccC gtG GCT gaA AAA acc ctC GCT TAT acc cgG cac
ctg tat gaa ATT gcC TCC gaa acc cag agc GAA TTT acc AAA gta GCT GAA
gct caa ctg GCT gaG GGT TCC AAA AAT GTg caa gcg ctg gtc GAA AAT ctc
GCT AAA AAT GCT ccC GCc ggt TCC gaa TCt acc GTT GCT ATT GTT AAA TCC
gcC ATc tcc gcC GCc AAT AAT GCc TAc GAA TCC GTg cag AAA gcg acc AAA
caa gcg gtc gaa ATT gcC gaa acc AAT TTc cag gct gcC gct acg gct GCT
acc AAA gct GCT cag caa GCT agc GCT acg GCT cgt acg <u>GCT</u> <u>acg</u> GCT <u>AAA</u>
<u>AAA</u> <u>acg</u> <u>acg</u> <u>gct</u> GCT tga

GAATTCCGGATATCTAGAAGCTTG

GTCGACTGCAGAGGCCTGCATGAAGCTTGGCGTAATCATGGTCATAGCTGTTTCCTGTGTAAATT

TABLE 10-continued

Synthesized DNA segments

P<sub>psbA2</sub> faa2

AGatATcGCGTGCAAGGCCCAGTGATCAATTTCATTATTTTTCATTATTTCATCTCCATTGTCCCTGAAAATCAGTTGTG

TCGCCCCTCTACACAGCCCAGAACTATGGTAAAGGCGCACGAAAAACCGCCAGGTAAACTCTTCTCAACCCCCAAAACGC

CCTCTGTTTACCCATGGAAAAAACGACAATTACAAGAAAGTAAAACTTATGTCATCTATAAGCTTCGTGTATATTAACTT

CCTGTTACAAAGCTTTACAAAACTCTCATTAATCCTTTAGACTAAGTTTAGTCAGTTCCAATCTGAACTAGGAATTATA

CAA

ATG GCT GCC CCT GAC TAT GCC TTA ACC GAT TTG ATT GAA AGT GAT CCC CGT TTC GAA TCT

TTG AAG ACC CGT TTG GCC GGT TAT ACT AAA GGG TCC GAC GAA TAC ATT GAA GAA CTG TAC

TCT CAA TTG CCC CTG ACT TCC TAC CCC CGT TAT AAA ACT TTC TTG AAA AAG CAG GCC GTC

GCC ATT AGT AAT CCT GAT AAT GAA GCC GGT TTT TCC TCT ATT TAC CGC TCC TCT CTC TCC

AGC GAA AAC CTG GTA TCC TGT GTC GAT AAA AAC TTG CGC ACT GCC TAT GAC CAC TTT ATG

TTT AGT GCC CGG CGT TGG CCC CAA CGG GAT TGT CTc GGt AGC CGG CCC ATC GAT AAA GCC

ACT GGC ACC TGG GAA GAA ACC TTT CGT TTT GAA TCT TAT AGT ACC GTT TCC AAG CGG TGC

CAC AAT ATC GGC TCC GGG ATC TTG TCC CTG GTG AAT ACT AAA CGC AAG CGC CCC TTA GAA

GCC AAC GAC TTT GTt GTc GCT ATC CTG TCC CAC AAT AAC CCC GAA TGG ATC TTG ACC GAT

TTG GCT TGT CAA GCC TAC AGT TTA ACC AAT ACC GCC CTG TAT GAA ACC CTG GGT CCC AAC

ACC TCT GAA TAT ATC CTG AAC TTG ACC GAG GCT CCG ATC CTG ATT TTT GCC AAA TCC AAC

ATG TAT CAC GTT CTC AAG ATG GTA CCC GAT ATG AAA TTT GTC AAC ACC TTG GTC TGC ATG

GAC GAA CTG ACC CAC GAC GAG TTA CGG ATG TTA AAC GAA AGC TTG CTG CCC GTA AAG TGT

AAC TCC CTG AAT GAG AAA ATT ACC TTT TTC AGC CTC GAA CAA GTG GAA CAA GTA GGT TGC

TTC AAC AAA ATT CCC GCC ATT CCT CCC ACC CCC GAT TCC CTG TAT ACC ATT AGC TTC ACC

AGC GGC ACT ACt GGt CTG CCC AAg GGc GTa GAg ATG TCT CAC CGg AAc ATT GCT TCC GGT

ATT GCC TTT GCT TTT AGC ACC TTT CGT ATC CCG CCG GAC AAG CGC AAC CAA CAA CTG TAT

GAC ATG TGC TTC CTG CCC TTG GCC CAC ATT TTC GAA CGG ATG GTG ATT GCT TAT GAC TTG

GCT ATT GGc TTT GGG ATC GGc TTc CTG CAC AAA CCg GAC CCt ACC GTG CTG GTA GAA GAC

TTG AAG ATC CTG AAA CCG TAC GCT GTC GCC CTG GTT CCC GGA TCC CTG ACC CGT TTC GAG

GCT GGC ATT AAA AAC GCC CTG GAT AAA AGC ACC GTT CAG CGG AAC GTG GCT AAT ACC ATC

CTG GAT AGC AAA TCT GCT CGC TTT ACt GCg CGT GGc GGt CCC GAC AAG TCT ATT ATG AAC

TTT TTG GTC TAC CAT CGG GTG CTG ATT GAT AAA ATC CGc GAC AGC CTC GGT TTA TCT AAC

AAC AGT TTC ATT ATC ACC GGT AGC GCT CCT ATC AGC AAa GAT ACt CTc CTC TTC TTG CGG

TCC GCC CTG GAC ATT GGT ATC CGG CAG GGT TAC GGC CTC ACt GAA ACt TTC GCC GGT GTT

TGT CTG TCC GAA CCT TTC GAA AAA GAC GTG GGT TCC TGT GGT GCC ATT GGT ATC TCC GCC

GAA TGC CGC CTC AAA TCC GTA CCC GAG ATG GGC TAC CAC GCT GAC AAA GAC CTG AAA GGG

GAA TTA CAA ATC CGT GGC CCG CAA GTG TTT GAA CGT TAC TTT AAG AAC CCC AAC GAA ACC

AGC AAA GCC GTG GAT CAA GAT GGT TGG TTT AGT ACC GGC GAC GTG GCg TTc ATT GAT GGT

AAA GGT CGT ATC TCC GTG ATT GAC CGC GTG AAA AAC TTC TTC AAA CTG GCC CAC GGT GAA

TAC ATT GCC CCC GAA AAA ATC GAA AAC ATT TAC TTG AGT TCT TGT CCC TAC ATT ACC AAA

ATT TTT GTC TTT GGT GAC CCC CTC AAA ACC TTT TTG GTA GGC ATT GTT GGG TCG ACG TGG

GAC GCC GCT CAA CCC ATT TTG GCT GCC AAA CAT CCG GAA GTG AAA ACT TGG ACC AAA GAA

TABLE 10-continued

Synthesized DNA segments

GTC CTC GTG GAA AAC CTG AAT CGG AAT AAA AAG CTG CGC AAA GAG TTT CTG AAT AAG ATT
AAC AAA TGT ACC GAC GGG TTG CAG GGT TTC GAA AAA TTG CAC AAC ATC AAA GTG GGC CTC
GAG CCT CTG ACC TTA GAA GAT GAT GTA GTT ACC CCT ACC TTC AAA ATT AAG CGT GCC AAA
GCC TCC AAA TTT TTC AAG GAT ACC TTG GAC CAA CTG TAC GCT GAA GGT AGC TTA GTG AAA
ACC GAA AAA CTG TAA gatatcat gp1

ATG Aaa TTG TTT GCC TGG ACT ATT GGT TTA CTG CTg ctg GCC ACt GTG CGC GGc GCT GAG
GTc TGT TAT TCT CAt TTG GGC TGc TTT TCC GAC GAG AAA CCG TGG GCg GGT ACC TCT CAA
CGG CCC ATC AAg AGT TTG CCg TCC GAC CCT AAA AAG ATT AAt ACC GGT TTC TTG CTG TAC
ACC AAt GAa AAt CAA AAT TCC TAC CAA CTG ATC ACC GCT ACT GAT ATT GCC ACC ATC AAA
GCC AGT AAC TTC AAT CTc AAC CGc AAA ACC CGC TTC ATT ATT CAC GGT TTC ACC GAC AGC
GGT GAG AAC TCT TGG CTG AGT GAT ATG TGT AAA AAC ATG TTC CAA GTT GAA AAA GTG AAT
TGC ATT TGC GTG GAT TGG AAA GGC GGT TCC AAG GCT CAA TAC AGT CAG GCT TCC CAG AAT
ATT CGG GTG GTC GGT GCC GAA GTT GCC TAT TTA GTG CAA GTA CTG AGC ACC TCC CTG AAC
TAT GCC CCG GAA AAC GTA CAT ATT ATT GGT CAC TCC CTC GGC GCC CAC ACC GCT GGG GAA
GCC GGG AAG CGG CTG AAC GGG CTG GTA GGG CGG ATT ACC GGc cTc GAC CCC GCC GAA CCC
TAC TTT CAA GAT ACC CCC GAA GAA GTC CGG CTG GAT CCC TCT GAC GCT AAA TTT GTG GAC
GTG ATT CAC ACT GAT ATT AGC CCC ATT CTG CCT AGT CTG GGT TTC GGT ATG TCC CAG AAG
GTC GGT CAC ATG GAC TTC TTC CCC AAC GGC GGC AAA GAT ATG CCC GGG TGC AAA ACC GGC
ATC TCC TGC AAC CAC CAC CGG AGT ATT GAA TAT TAT CAC AGC AGT ATT TTG AAC CCC GAA
GGT TTt TTa GGC TAC CCG GTG CT GCC TAC GAT GAA TTc CAA GAA TCt GGG TGC TTC CCC
TGT CCC GCT AAA GGT TGT CCT AAA ATG GGT CAC TTT GCC GAC CAG TAC CCC GGg AAG ACC
AAT GCT GTC GAA CAA ACC TTc TTC CTC AAC ACC GGg GCg TCC GAT AAT TTC ACC CGG TGG
CGC TAT AAA GTA ACC GTT ACC CTG AGT GGC GAA AAA GAC CCG TCC GGT AAC ATC AAT GTG
GCT TTG TTA GGT AAA AAC GGG AAC TCT GCT CAA TAC CAG GTT TTC AAG GGC ACC CTG AAG
CCC GAC GCC TCC TAT ACT AAT TCC ATT GAT GTC GAA CTC AAC GTT GGG ACC ATT CAA AAA
GTG ACC TTC CTG TGG AAA CGG AGC GGG ATC TCC GTC TCT AAA CCC AAG ATG GGT GCT TCt
CGc ATT ACt GTT CAA AGT GGT AAA GAC GGG ACC AAA TAT AAC TTC TGC TCC AGC GAT ATT
GTG CAA GAA AAC GTC GAG CAG ACT CTG AGC CCC TGC taa A RBS fol RBS sh1

TTCCCAATTTGAGGaGGTGTG

ATG GAA GTa TCC CAa GAT CTG TTT AAT CAA TTC AAT CTG TTC GCT CAA TAC TCC GCg GCT
GCT TAC TGT GGg AAA AAT AAC GAT GCT CCT GCg GGc ACC AAT ATT ACt TGT ACC GGT AAC
GCT TGC CCT GAA GTG GAg AAg GCT GAC GCC ACC TTT TTG TAC AGC TTC GAA GAT AGC GGC
GTA GGC GAT GTG ACT GGt TTC cTc GCC TTG GAT AAT ACC AAT AAA TTG ATT GTT CTC TCT
TTC CGT GGC agt GAc TCC ATT GAG AAT TGG ATT GCC AAC TTG AAc TTt TGG TTG AAG AAA
ATC AAt GAt ATT TGT TCC GGc TGT CGG GGt CAC GAT GGT TTC ACC AGC AGC TGG CGT TCC
GTG GCC GAC ACC CTC CGG CAA AAG GTg GAa GAT GCT GTg CGc GAA CAt CCt GAT TAC CGC

TABLE 10-continued

Synthesized DNA segments

GTT GTT TTT ACC GGG CAC TCC CTG GGC GGG GCC TTG GCC ACC GTA GCC GGT GCT GAC CTG

CGC GGT AAC GGC TAC GAT ATT GAT GTG TTC TCC TAT GGG GCT CCC CGG GTT GGG AAC CGG

GCT TTT GCt GAg TTT TTG ACC GTt CAa ACC GGc GGT ACC TTG TAT CGG ATC ACC CAT ACC

AAT GAT ATT GTT CCC CGC CTG CCC CCT CGT GAA TTC GGT TAT AGC CAC TCC TCC CCC GAA

TAC TGG ATT AAA AGC GGC ACC TTG GTT CCC GTG ACC CGT AAC GAC ATT GTA AAA ATT GAG

GGC ATT GAC GCC ACC GGT GGT AAT AAT CAA CCT AAT ATC CCC GAT ATC TTG GCT CAT CTG

TGG TAT TTT CAA GCC ACC GAC GCT TGT AAC GCC GGC GGT TTC AGT TAA

TGAGGAGATTAATTCA

ATGAAGCCTACCGTTAAAGCTGCTCCCGAGGCTGTTCAGAACCCGGAAAACCCGAAAAACAAGG

ACCCCTTTGTGTTTGTGCACGGCTTTACCGGTTTTGTGGGGAGGTTGCTGCGAAAGGTGAGAA

TCACTGGGGCGGCACCAAAGCCAATCTGCGCAACCATTTGCGGAAAGCTGGTTACGAAACCTAC

GAAGCCTCCGTATCCGCCTTGGCCTCCAATCACGAACGTGCTGTGGAACTGTACTATTATCTGA

AAGGTGGTCGGGTAGACTATGGTGCTGCCCATTCCGAAAAATATGGCCATGAGCGTTACGGGAA

AACTTATGAAGGTGTGCTGAAAGATTGGAAACCCGGGCACCCCGTACACTTTATCGGTCATTCC

ATGGGTGGTCAGACCATTCGGCTGCTGGAACATTATCTGCGCTTTGGTGATAAAGCCGAAATTG

CCTATCAACAACAGCACGGGGGTATTATTAGCGAATTATTTAAGGGCGGTCAAGACAACATGGT

GACCTCTATCACTACTATTGCCACCCCTCACAATGGTACCCATGCTTCTGACGATATTGGCAAT

ACCCCGACTATCCGGAACATTCTGTATAGCTTCGCCCAAATGTCCAGTCATCTGGGCACCATCG

ACTTTGGGATGGACCATTGGGGTTTCAAGCGGAAAGATGGCGAGAGTCTGACCGATTATAATAA

GCGGATTGCCGAGAGCAAAATCTGGGATTCTGAAGATACTGGGCTGTATGACCTGACCCGTGAA

GGCGCCGAGAAAATCAACCAGAAAACCGAATTGAATCCCAATATCTATTACAAAACCTACACTG

GGGTGGCTACCCATGAAACTCAGTTAGGCAAACACATCGCGGACCTCGGCATGGAATTTACCAA

AATCCTCACCGGCAACTATATCGGGAGCGTAGACGATATTCTGTGGCGGCCCAATGATGGTTTG

GTGAGCGAAATCTCCAGCCAACACCCCAGCGATGAGAAGAACATTTCCGTAGACGAAAACTCCG

AACTGCATAAGGGTACCTGGCAGGTCATGCCTACCATGAAAGGGTGGGACCACTCCGATTTTAT

TGGTAATGACGCCCTGGATACCAAACACTCCGCCATCGAACTCACCAACTTTTATCATAGCATT

TCTGACTACTTGATGCGGATCGAAAAAGCCGAATCTACCAAAAACGCCTAATGATATCGA

Ptrc tesA137

GAGCTGTTGACAATTAATCATCCGGCTCGTATAATTTTAAAGAGGAGAAA

ATG AAA GCT GAT ACT CTG TTG ATT TTG GGG GAC TCC TTG TCT GCT GGT TAT CGT ATG TCC

GCT AGC GCC GCT TGG CCC GCC TTG CTC AAC GAC AAA TGG CAA GTA AAG ACT TCC GTT GTG

AAT GCT TCC ATT AGt GGT GAC ACC AGC CAG CAG GGC CTG GCT CGT CTC CCC GCT CTG CTC

AAA CAG CAT CAG CCC CGT TGG GTC CTG GTA GAA CTG GGC GGT AAC GAC GGT CTc CGc GGC

TTC CAA CCT CAA CAG ACC GAA CAA ACC CTC CGG CAG ATC TTA CAG GAT GTG AAA GCC GCC

AAC GCC GAA CCC CTC CTG ATG CAA ATC GCC CTG CCC GCC AAC TAT GGT CGG CGC TAT AAC

GAA GCC TTC AGT GCT ATC TAT CCC AAA CTC GCT AAG GAA TTC GAC GTG CCC CTG CTG CCC

TTT TTC ATG GAA GAA GTT TAT CTG AAA CCC AGT GGA TGC AAA GAC GAT GGT ATT CAT CCC

AAT CGT GAC GCT CAA CCC TTT ATT GCC GAT TGG ATG GCT AAA CAA TTA CAA CCC CTC GTA

AAC CAC GAT TCC GAC TAT AAA GAT GAc GAT GAc AAG TAA gatatcga

TABLE 10-continued

Synthesized DNA segments

*P<sub>sbA2</sub> UC fatB1 P<sub>rbc</sub> Ch fatB2

AGatATcGCGTGCAAGGCCCAGTGATCAATTTCATTATTTTTCATTATTTCATCTCCATTGTCCCTGAAAATCAGTTGTGTCGCCC

CTCTACACAGCCCAGAACTATGGTAAAGGCGCACGAAAAACCGCCAGGTAAACTCTTCTCAACCCCCAAAACGCCCTCTGTTTACC

CATGGAAAAAACGACAATTACAAGAAAGTAAAACTTATGTCATCTATAAGCTTCGTGTATATTAACTTCCTGTTACAAAGCTTTAC

AAAACTCTCATTAATCCTTTAGACTAAGTTTAGTCAGTTCCAATCTGAACTAAGGAATTATAACCAA

ATG GCt ACC ACC TCT TTA GCT TCC GCc TTt TGC TCG ATG AAA GCT GTA ATG TTa GCT CGT

GAT GGt CGG GGt ATG AAA CCt CGT AGt AGT GAT TTG CAA CTc CGT GCG GGA AAT GCG CCT

ACC TCT TTG AAA ATG ATC AAT GGG ACC AAA TTC AGT TAT ACG GAG AGC TTG AAA CGG TTG

CCT GAT TGG AGC ATG CTC TTT GCT GTT ATC ACC ACC ATC TTT TCG GCT GCT GAG AAA CAA

TGG ACt AAT CTA GAG TGG AAG CCG AAA CCG AAG CTA CCC CAG TTG CTT GAT GAT CAT TTT

GGA CTG CAT GGG TTA GTT TTC CGG CGC ACC TTT GCC ATC CGG TCT TAT GAa GTT GGA CCT

GAT CGC TCC ACC TCT ATT CTG GCT GTT ATG AAT CAT ATG CAG GAG GCT ACC CTT AAT CAT

GCG AAA AGT GTG GGA ATT CTA GGA GAT GGA TTC GGG ACG ACG CTA GAG ATG AGT AAG CGG

GAT CTG ATG TGG GTT GTT CGG CGC ACG CAT GTT GCT GTT GAA CGG TAC CCT ACT TGG GGT

GAT ACT GTA GAA GTA GAG TGC TGG ATT GGT GCT TCT GGA AAT AAT GGC ATG CGT CGT GAT

TTC CTT GTC CGG GAC TGC AAA ACC GGC GAA ATT CTT ACT CGC TGT ACC AGC TTT TCG GTG

CTG ATG AAT ACT CGC ACt CGt CGT TTG TCC ACC ATt CCT GAT GAA GTT CGT GGt GAa ATA

GGG CCT GCT TTC ATc GAT AAT GTT GCT GTg AAA GAC GAT GAA ATT AAG AAA CTA CAA AAA

CTC AAT GAT AGC ACT GCC GAT TAT ATt CAA GGA GGT TTG ACc CCT CGT TGG AAT GAT TTG

GAT GTC AAT CAA CAT GTT AAC AAC CTC AAA TAC GTT GCC TGG GTT TTT GAG ACC GTC CCc

GAt TCC ATC TTT GAG AGT CAT CAT ATT TCC AGC TTC ACT CTT GAA TAT CGT CGT GAG TGt

ACc CGT GAT AGC GTG CTG CGG TCC CTG ACC ACT GTC TCT GGT GGC TCG TCG GAG GCT GGG

TTA GTT TGC GAT CAT TTG CTC CAA CTT GAA GGT GGG TCT GAG GTA TTG CGT GCC AGA ACT

GAG TGG CGG CCT AAA CTT ACC GAT AGT TTC CGC GGc ATT AGT GTT ATT CCC GCC GAA CCG

CGC GTG TAA

GGAGAGCATTGCCATAAGTAAAGGCATCCCCTGCGTGATAAGATTACCTTCAGAAAACAGATAGTTGCTGGGTTATCGCAGATTTT

TCTCGCAACCAAATAACTGTAAATAATAACTGTCTCTGGGGCGACGGTAGGCTTTATATTGCCAAATTTCGCCCGTGGGAGAAAGC

TAGGCTATTCAATGTTTATGGAGGACTGACCTAG

ATG GTG GCT GCT GCT GCT AGT TCC GCT TTC TTC CCT GTT CCA GCC CCc GGA GCC TCC CCT

AAA CCC GGG AAG TTC GGA AAT TGG CCC AGT AGC TTG AGC CCT TCC TTC AAG CCC AAG TCA

ATC CCC AAT GGC GGA TTT CAG GTT AAG GCT AAT GAC AGC GCC CAT CCA AAa GCc AAt GGT

TCT GCc GTT AGT CTA AAG TCT GGC AGC CTC AAC ACT CAa GAa GAC ACT AGT TCC TCC CCT

CCT CCT CGG ACT TTC CTT CAt CAG TTG CCT GAT GGA AGT CGt CTT CTG ACT GCT ATt ACc

ACC GTG TTC GTG AAA TCT AAG CGT CCT GAC ATG CAT GAT CGG AAA TCC AAG CGT CCT GAC

ATG CTG GTG GAC TCC TTT GGG TTG GAG AGT ACT GTT CAG GAT GGc tTa GTG TTC CGA CAG

AGT TTT TCC ATT CGT TCT TAT GAA ATA GGC ACT GAT CGA ACG GCC TCT ATA GAG ACC TTT

ATG AAC CAC TTG CAG GAA ACC TCT CTC AAT CAT TGT AAG AGT ACC GGT ATT CTC CTT GAC

GGC TTC GGT CGT ACT CTT GAG ATG TGT AAA CGC GAC CTC ATT TGG GTG GTA ATT AAA ATG

TABLE 10-continued

Synthesized DNA segments

CAG ATC AAG GTG AAT CGC TAT CCA GCT TGG GGC GAT ACT GTC GAG ATC AAT ACC CGt TTC
agC CGG TTG GGG AAA ATt GGT ATG GGT CGC GAT TGG CTA ATT AGT GAT TGC AAC ACC GGA
GAA ATT CTT GTA CGG GCT ACG AGC GCG TAT GCC ATG ATG AAT CAA AAG ACG CGG AGA CTC
TCC AAA CTT CCA TAC GAG GTT CAC CAG GAG ATT GTG CCT CTT TTT GTC GAC TCT CCT GTC
ATT GAA GAC AGT GAT CTG AAA GTG CAT AAG TTT AAA GTG AAG ACT GGT GAc agC ATT CAA
AAG GGT CTA ACT CCG GGG TGG AAT GAC TTG GAT GTC AAT CAG CAC GTA AGC AAC GTG AAG
TAC ATT GGG TGG ATT CTC GAG AGT ATG CCA ACA GAA GTT TTG GAG ACC CAG GAG CTA TGC
TCT CTC GCC CTT GAA TAT CGC CGG GAA TGC GGA CGC GAC AGT GTG CTG GAG TCC GTG ACC
GCT ATG GAT CCC TCC AAA GTT GGA GTC CGT TCT CAG TAC CAG CAC CTT CTG CGG CTT GAG
GAT GGG ACT GCT ATC GTG AAC GGT GCT ACT GAG TGG CGG CCG AAG AAT GCA GGA GCT AAC
GGG GCG ATc agC ACG GGA AAG ACT TCC AAT GGA AAC TCG GTC TCT TAA tgatatca \*p*psbA2* Ch fatB2

AGatATcGCGTGCAAGGCCCAGTGATCAATTTCATTATTTTTCATTATTTCATCTCCATTGTCCCTGAAAATCAGTTGT
GTCGCCCCTCTACACAGCCCAGAACTATGGTAAAGGCGCACGAAAAACCGCCAGGTAAACTCTTCTCAACCCCCAAAAC
GCCCTCTGTTTACCCATGGAAAAAACGACAATTACAAGAAAGTAAAACTTATGTCATCTATAAGCTTCGTGTATATTAA
CTTCCTGTTACAAAGC TTTACA AAACTCTCATTAATCCTT TAGACT AAGTTT A GTCAGTTCCAATCTGAACTAAGGAA
TTATAACCAA
ATG GTG GCT GCT GCT GCT AGT TCC GCT TTC TTC CCT GTT CCA GCC CCc GGA GCC TCC CCT
AAA CCC GGG AAG TTC GGA AAT TGG CCC AGT AGC TTG AGC CCT TCC TTC AAG CCC AAG TCA
ATC CCC AAT GGC GGA TTT CAG GTT AAG GCT AAT GAC AGC GCC CAT CCA AAa GCc AAt GGT
TCT GCc GTT AGT CTA AAG TCT GGC AGC CTC AAC ACT CAa GAa GAC ACT AGT TCC TCC CCT
CCT CCT CGG ACT TTC CTT CAt CAG TTG CCT GAT TGG AGT CGt CTT CTG ACT GCT ATt ACc
ACC GTG TTC GTG AAA TCT AAG CGT CCT GAC ATG CAT GAT CGG AAA TCC AAG CGT CCT GAC
ATG CTG GTG GAC TCC TTT GGG TTG GAG AGT ACT GTT CAG GAT GGc tTa GTG TTC CGA CAG
AGT TTT TCC ATT CGT TCT TAT GAA ATA GGC ACT GAT CGA ACG GCC TCT ATA GAG ACC CTT
ATG AAC CAC TTG CAG GAA ACC TCT CTC AAT CAT TGT AAG AGT ACC GGT ATT CTC CTT GAC
GGC TTC GGT CGT ACT CTT GAG ATG TGT AAA CGC GAC CTC ATT TGG GTG GTA ATT AAA ATG
CAG ATC AAG GTG AAT CGC TAT CCA GCT TGG GGC GAT ACT GTC GAG ATC AAT ACC CGt TTC
agC CGG TTG GGG AAA ATt GGT ATG GGT CGC GAT TGG CTA ATT AGT GAT TGC AAC ACC GGA
GAA ATT CTT GTA CGG GCT ACG AGC GCG TAT GCC ATG ATG AAT CAA AAG ACG CGG AGA CTC
TCC AAA CTT CCA TAC GAG GTT CAC CAG GAG ATT GTG CCT CTT TTT GTC GAC TCT CCT GTC
ATT GAA GAC AGT GAT CTG AAA GTG CAT AAG TTT AAA GTG AAG ACT GGT GAc agC ATT CAA
AAG GGT CTA ACT CCG GGG TGG AAT GAC TTG GAT GTC AAT CAG CAC GTA AGC AAC GTG AAG
TAC ATT GGG TGG ATT CTC GAG AGT ATG CCA ACA GAA GTT TTG GAG ACC CAG GAG CTA TGC
TCT CTC GCC CTT GAA TAT CGC CGG GAA TGC GGA CGC GAC AGT GTG CTG GAG TCC GTG ACC
GCT ATG GAT CCC TCC AAA GTT GGA GTC CGT TCT CAG TAC CAG CAC CTT CTG CGG CTT GAG
GAT GGG ACT GCT ATC GTG AAC GGT GCT ACT GAG TGG CGG CCG AAG AAT GCA GGA GCT AAC
GGG GCG ATc agC ACG GGA AAG ACT TCC AAT GGA AAC TCG GTC TCT TAA tgatatca TABLE 10-continued Synthesized DNA segments P<sub>psbA2*</sub> Cc fatB1

AGatATcGCGTGCAAGGCCCAGTGATCAATTTCATTATTTTTCATTATTTCATCTCCATTGTCCCTGAAAATCAGTTGT
GTCGCCCCTCTACACAGCCCAGAACTATGGTAAAGGCGCACGAAAAACCGCCAGGTAAACTCTTCTCAACCCCCAAAAC
GCCCTCTGTTTACCCATGGAAAAAACGACAATTACAAGAAAGTAAAACTTATGTCATCTATAAGCTTCGTGTATATTAA
CTTCCTGTTACAAAGCTTTACAAAACTCTCATTAATCCTTTAGACTAAGTTTAGTCAGTTCCAATCTGAACTAAGGAA
TTATAACCAA

ATG AAA ACT ACT TCT CTC GCC TCT GCC TTC TGT TCT ATG AAA GCT GTT ATG CTG GCg CGG
GAT GGT CGC GGT ATG AAA CCC CGT TCC AGT GAT CTG CAA TTA CGG GCT GGC AAC GCT CAG
ACC TCC TTG AAG ATG ATT AAC GGC ACT AAA TTC AGT TAT ACC GAA TCT TTG AAG AAA CTC
CCC GAT TGG AGC ATG TTG TTC GCC GTG ATT ACC ACC ATt TTt AGT GCT GCC GAA AAA CAA
TGG ACC AAT CTC GAA TGG AAA CCC AAA CCC AAC CCC CCG CAG CTG CTC GAT GAC CAT TTT
GGc CCC CAC GGC TTG GTG TTT CGG CGT ACC TTC GCT ATC CGG TCT TAT GAA GTC GGT CCC
GAT CGG AGC ACT TCC ATC GTC GCT GTT ATG AAT CAC TTG CAA GAA GCC GCT TTG AAC CAt
GCT AAA tct GTT GGG ATT CTG GGT GAT GGC TTC GGT ACC ACT CTG GAG ATG AGT AAG CGC
GAT CTG ATC TGG GTA GTA AAG CGT ACt CAT GTG GCC GTG GAA CGT TAt CCg GCC TGG GGT
GAT ACC GTA GAA GTG GAG TGT TGG GTA GGC GCC TCC GGT AAC AAC GGT CGG CGT CAC GAC
TTC TTG GTG CGT GAC TGT AAA ACt GGc GAG ATC CTG ACC CGC TGT ACT TCC CTG AGC GTT
ATG ATG AAC ACC GGG ACC CGT CGC TTA TCC AAG ATT CCC GAA GAA GTT CGC GGG GAA ATT
GGt CCt GCT TTC ATT GAT AAC GTT GCT GTT AAG GAT GAG GAG ATT AAA AAG CCG CAA AAG
CTC AAT GAT TCT ACC GCC GAT TAC ATT CAA GGG GGT CTG ACT CCC CGT TGG AAT GAT CTG
GAT ATT AAT CAG CAT GTG AAT AAC ATC AAA TAT GTG GAT TGG ATT CTG GAG ACT GTG CCC
GAC TCT ATT TTC GAG TCC CAC CAC ATT agc AGT TTT ACC ATT GAA TAT CGT CGC GAA TGT
ACT ATG GAC AGT GTT TTG CAA TCC CTG ACC ACC GTC TCC GGC GGT TCC TCT GAA GCT GGC
CTG GTG TGC GAA CAC CTC TTG CAA CTC GAA GGC GGT AGT GAA GTg CTc CGt GCC AAG ACC
GAA TGG CGG CCC AAA TTG ACC GAC TCC TTT CGC GGG ATT TCT GTG ATT CCC GCC GAA TCC
TCC GTC TAA GATATCAT P<sub>psbA2*</sub> Cc fatB1

AGatATcGCGTGCAAGGCCCAGTGATCAATTTCATTATTTTTCATTATTTCATCTCCATTGTCCCTGAAAATCAGTTGT
GTCGCCCCTCTACACAGCCCAGAACTATGGTAAAGGCGCACGAAAAACCGCCAGGTAAACTCTTCTCAACCCCCAAAAC
GCCCTCTGTTTACCCATGGAAAAAACGACAATTACAAGAAAGTAAAACTTATGTCATCTATAAGCTTCGTGTATATTAA
CTTCCTGTTACAAAGCTTTACAAAACTCTCATTAATCCTTTAGACTAAGTTTAGTCAGTTCCAATCTGAACTAAGGAA
TTATAACCAA

ATG AAA ACT ACT TCT CTC GCC TCT GCC TTC TGT TCT ATG AAA GCT GTT ATG CTG GCg CGG
GAT GGT CGC GGT ATG AAA CCC CGT TCC AGT GAT CTG CAA TTA CGG GCT GGC AAC GCT CAG
ACC TCC TTG AAG ATG ATT AAC GGC ACT AAA TTC AGT TAT ACC GAA TCT TTG AAG AAA CTC
CCC GAT TGG AGC ATG TTG TTC GCC GTG ATT ACC ACC ATt TTt AGT GCT GCC GAA AAA CAA
TGG ACC AAT CTC GAA TGG AAA CCC AAA CCC AAC CCC CCG CAG CTG CTC GAT GAC CAT TTT
GGc CCC CAC GGC TTG GTG TTT CGG CGT ACC TTC GCT ATC CGG TCT TAT GAA GTC GGT CCC
GAT CGG AGC ACT TCC ATC GTC GCT GTT ATG AAT CAC TTG CAA GAA GCC GCT TTG AAC CAt

TABLE 10-continued

Synthesized DNA segments

GCT AAA tct GTT GGG ATT CTG GGT GAT GGC TTC GGT ACC ACT CTG GAG ATG AGT AAG CGC
GAT CTG ATC TGG GTA GTA AAG CGT ACt CAT GTG GCC GTG GAA CGT TAt CCg GCC TGG GGT
GAT ACC GTA GAA GTG GAG TGT TGG GTA GGC GCC TCC GGT AAC AAC GGT CGG CGT CAC GAC
TTC TTG GTG CGT GAC TGT AAA ACt GGc GAG ATC CTG ACC CGC TGT ACT TCC CTG AGC GTT
ATG ATG AAC ACC GGA ACC CGT CGC TTA TCC AAG ATT CCC GAA GAA GTT CGC GGG GAA ATT
GGt CCt GCT TTC ATT GAT AAC GTT GCT GTT AAG GAT GAG GAG ATT AAA AAG CCG CAA AAG
CTC AAT GAT TCT ACC GCC GAT TAC ATT CAA GGG GGT CTG ACT CCC CGT TGG AAT GAT CTG
GAT ATT AAT CAG CAT GTG AAT AAC ATC AAA TAT GTG GAT TGG ATT CTG GAG ACT GTG CCC
GAC TCT ATT TTC GAG TCC CAC CAC ATT agc AGT TTT ACC ATT GAA TAT CGT CGC GAA TGT
ACT ATG GAC AGT GTT TTG CAA TCC CTG ACC ACC GTC TCC GGC GGT TCC TCT GAA GCT GGC
CTG GTG TGC GAA CAC CTC TTG CAA CTC GAA GGC GGT AGT GAA GTg CTc CGt GCC AAG ACC
GAA TGG CGG CCC AAA TTG ACC GAC TCC TTT CGC GGG ATT TCT GTG ATT CCC GCC GAA TCC
TCC GTC TAA <u>GATATCAT</u>

EHC1

<u>GAtaTC</u> <u>GTTCGTTAAT</u> <u>TTTTCCCA</u> <u>TCGCTTTTAG</u>
TAGATGTAGGCAGATCCAACCATCGGTAAAGTTGATTAG
TGTGGCCCAG GCCCATCGCCGGCAGG GATTGGGAAA
GTATCACGAATTACACTGCCGTGAAAATTTAACGATATTTTGGACAG
GGGAAAGATT GGCGATCGCCGTTGTG GTTAAGCCAG
CTAAAAGGCCCACTCGTTAGGACACACGGTGTAAAAAAAA
ACAAAATATT TTTGCCCA TTTTTGCGGT
CAACTTTGACTGACCAGCTAATTTTGTACACGACTTAGGAGTT
TGTAATTTCG TCGAGTCCCA GCCACCCCCGACCC AAGTTTGCTT
GCTTTACAAA<u>ACTCTCATTAATCCTTAGACTAAGTTTA</u> <u>GAtaTC</u>

EHC2

AT<b>GATATC</b> TGTAATTTCG TCGAGTCCCA GCCACCCCCGACCC AAGTTTGCTT
GCTTTACAAAACTCTCATTAATCCTTAGACTAAGTTTA
ACAAAATATT TTTGCCCA TTTTTGCGGT
CAACTTTGACTGACCAGCTAATTTTGTACACGACTTAGGAGTT
GGGAAAGATT GGCGATCGCCGTTGTG GTTAAGCCAG
CTAAAAGGCCCACTCGTTAGGACACACGGTGTAAAAAAAA
GTTCGTTAAT TTTTCCCA TCGCTTTTAG
TAGATGTAGGCAGATCCAACCATCGGTAAAGTTGATTAG
TGTGGCCCAG GCCCATCGCCGGCAGG GATTGGGAAA
GTATCACGAATTACACTGCCGTGAAAATTTAACGATATTTTGGACAG
AGCTG<u>TTGACA</u>ATTAATCATCCGGCTCG<u>TATAATTTTAA</u><b>AGAGGAGAAA</b><u>CAA</u>

P<sub>trc</sub> adc7421 P<sub>trc</sub> aar7421 ga<u>GATATC</u>GAGCTG<u>TTGACA</u>ATTAATCATCCGGCTCG<u>TATAATTTTAA</u><b>AGAGGAGAAA</b>C<u>AA</u>
<u>ATGTTCGGTCTGATCGGGCACCTC</u>ACCAATTTGTCCCACGCCCAACGGGTTGCCCGCGACTT

TABLE 10-continued

Synthesized DNA segments

GGGCTACGACGAATACGCCTCCCACGATTTAGAATTTTGGTGCATGGCCCCCCCCAAGCCG

TTGACGAAATCACTATTACTTCCGTGACCGGTCAGGTGATCCACGGCCAGTATGTAGAGTCCT

GTTTTTTACCCGAAATGCTCGCGCAAGGGCGGTTCAAGACTGCTATGCGCAAAATCCTGAACG

CCATGGCCCTGGTACAAAAACGGGGTATTGACATTACCGCTTTAGGGGGGTTCAGTAGCATCA

TTTTCGAGAATTTTTCCCTCGATAAATTGCTCAATGTGCGTGATATTACCCTCGACATCCAGC

GCTTCACCACCGGCAACACTCACACCGCGTATATTTTGTGTCAACAAGTGGAACAAGGTGCGG

TACGGTACGGTATTGATCCCGCCAAAGCCACCGTTGCCGTGGTCGGGGCCACCGGTGATATTG

GTTCCGCCGTATGCCGCTGGTTGACTGATCGGGCTGGGATCCACGAATTGTTGTTGGTGGCCC

GTGACGCTGAACGTCTCGACCGGCTCCAACAAGAACTCGGTACCGGTCGGATTCTCCCCGTGG

AGGAGGCCCTGCCCAAAGCGGATATTGTGGTATGGGTGGCTTCCATGAACCAGGGGATGGCTA

TCGACCCCGCGGGGCTGCGTACCCCCTGTTTGCTCATCGATGGTGGCTACCCCAAAAACATGG

CGGGCACCTTGCAACGGCCCGGCATTCACATTCTGGACGGGGGCATGGTTGAACACTCCTTGG

ACATCGACTGGCAGATTATGAGCTTCCTGAATGTGCCGAACCCCGCCCGGCAATTCTTCGCTT

GTTTTGCTGAAAGCATGCTGCTGGAATTCGAAGGTTTGCACTTCAACTTTTCCTGGGGTCGTA

ACCATATTACTGTAGAAAAGATGGCGCAAATTGGCTCCCTGAGCAAGAAACACGGCTTTCGCC

CTTTGTTGGAACCCTCCCAACGCTCCGGTGAACTGGTGCACGGTtaa

AGCTGTTGACAAcTgATCATaCGtCTCGTATAATTTTAAAGAGGAGAAACAA

ATGAATCGGACCGCTCCCTCCTCTGCCGCTTTGGACTACCGGTCTGATACCTA

TCGGGATGCCTATAGCCGCATTAACGCTATTGTCCTCGAAGGTGAACGGGAAG

CGCACGCGAATTATTTGACCTTGGCCGAAATGCTGCCCGACCATGCCGAAGCT

CTGAAAAAGTTGGCCGCTATGGAAAATCGCCACTTCAAAGGCTTCCAGTCCTG

CGCCCGTAATCTCGAAGTGACCCCCGATGATCCCTTCGCGCGTGCGTACTTCG

AGCAATTGGATGGCAACTTCCAACAGGCCGCTGCCGAAGGTGACTTGACCACTT

GTATGGTCATTCAAGCGCTCATTATTGAATGTTTTGCCATTGCCGCCTATAACG

TGTACATTCCTGTCGCCGACGCCTTCGCCCGCAAAGTGACCGAGGGTGTTGTCA

AAGACGAGTACACTCATTTAAACTTTGGCCAACAATGGCTGAAGGAACGTTTCG

TAACTGTGCGTGAAGGTATCGAGCGTGCCAATGCTCAAAACTTGCCCATTGTTT

GGCGCATGCTCAATGCTGTTGAAGCCGATACCGAAGTTTTGCAGATGGATAAGG

AAGCCATTGTCGAAGACTTCATGATTGCTTACGGTGAAGCCCTCGGTGATATTG

GGTTTAGCATGCGTGATGTGATGAAAATGTCCGCTCGTGGTTTGGCCAGTGCTCCCCGCCAAtaagatatc

P<sub>psbA2</sub> aar7942 P<sub>trc</sub> adc73012

AGatATCGCGTGCAAGGCCCAGTGATCAATTTCATTATTTTTCATTATTTCATCT

CCATTGTCCCTGAAAATCAGTTGTGTCGCCCCTCTACACAGCCCAGAACTATGGT

AAAGGCGCACGAAAAACCGCCAGGTAAACTCTTCTCAACCCCCAAAACGCCCTCT

GTTTACCCATGGAAAAAACGACAATTACAAGAAAGTAAAACTTATGTCATCTATA

AGCTTCGTGTATATTAACTTCCTGTTACAAAGCTTTACAAAACTCTCATTAATCC

TTTAGACTAAGTTTAGTCAGTTCCAATCTGAACgAAGGAATTATAACCAA

ATGaaaTTTGGTTTAATTGGTCATCTCACTAGTTTAGAGCAGGCCCGGGATGTTTC

TABLE 10-continued

Synthesized DNA segments

CCGTCGGATGGGTTATGATGAGTACGCCGATCAGGGTTTGGAATTTTGGTCTTCCG

CTCCTCCCCAAATCGTTGATGAAATCACCGTTACTTCCGCCACCGGTAAGGTGATC

CACGGTCGTTACATTGAAAGTTGTTTCCTGCCCGAAATGTTGGCCGCTCGCCGGTT

TAAAACCGCCACCCGTAAAGTGTTGAACGCTATGAGCCACGCTCAGAAACACGGCA

TTGATATCTCCGCCCTCGGTGGTTTTACCAGTATCATTTTTGAAAACTTTGATCTC

GCTAGTCTCCGTCAAGTGCGGGACACTACCCTGGAGTTTGAACGGTTCACTACTGG

CAACACCCATACCGCCTACGTTATCTGTCGTCAAGTTGAGGCCGCTGCGAAAACCC

TGGGGATCGATATTACCCAGGCTACCGTTGCCGTGGTAGGCGCCACCGGGGATATC

GGTAGTGCTGTTTGCCGGTGGTTAGATCTGAAATTGGGTGTGGGGGATCTCATTT

TGACTGCTCGGAACCAGGAACGCCTGGATAATCTGCAAGCTGAATTGGGTCGCGG

CAAGATCCTCCCCTTAGAAGCCGCCCTCCCCGAAGCCGATTTCATTGTGTGGGTC

GCCTCTATGCCCCAAGGTGTTGTTATTGACCCCGCCACTCTGAAACAGCCTTGTG

TTTTGATCGATGGGGGTTACCCTAAAAACCTGGGCTCCAAAGTACAGGGTGAAGG

CATCTACGTGCTCAATGGGGCGTCGTGGAACACTGTTTTGATATCGACTGGCAA

ATTATGAGCGCTGCCGAAATGGCTCGCCCCGAGCGTCAAATGTTTGCCTGTTTTG

CCGAGGCCATGTTGTTGGAATTCGAAGGGTGGCACACCAACTTCTCCTGGGGTCG

CAACCAAATTACCATTGAAAAGATGGAAGCGATCGGCGAAGCCTCTGTGCGTCAT

GGTTTTCAGCCCTTGGCTTTAGCCATCtaa

GAGCTG<u>TTGACA</u>ATTAATCATCCGGCTCG<u>TATAAT</u>TTTAAAGAGGAGAAACAA

ATGAAACAGCAATTGACCGACCAAAGTAAAGAGCTCGATTTTAAGTCCGAAACCTA

TAAAGACGCCTACAGTCGGATCAATGCCATTGTGATTGAAGGTGAACAGGAAGCGC

ATGAAAATTACATCACTTTGGCCCAACTGCTCCCGGAGTCCCACGACGAACTGATC

CGCTTGTCCAAGATGGAATCCCGGCATAAGAAAGGCTTTGAAGCGTGCGGCCGTAA

CCTGGCGGTAACCCCCGACTTACAGTTTGCCAAAGAATTTTTCAGCGGTTTGCATC

AAAATTTTCAGACCGCCGCTGCCGAAGGTAAAGTGGTGACTTGCCTGCTCATTCAG

TCTCTCATTATCGAGTGCTTCGCGATCGCTGCCTATAACATTTACATCCCCGTTGC

TGATGATTTTGCCCGCAAAATCACTGAAGGCGTAGTAAAAGAAGAATACTCCCATT

TGAATTTCGGCGAAGTGTGGCTGAAAGAGCATTTCGCTGAATCCAAAGCTGAACTC

GAACTGGCCAACCGCCAAAATTTGCCCATTGTTTGGAAAATGCTCAACCAGGTGGA

GGGGGATGCCCACACTATGGCCATGGAAAAAGACGCCTTGGTTGAAGATTTATGA

TTCAATACGGTGAAGCCCTCTCCAACATTGGCTTCTCTACCCGGGACATTATGCGC

TTG<u>AGTGCCTACGGGTTGATCGGTGCTTAA</u>gatatcag

P<sub>trc</sub> adc1986 P<sub>trc</sub> aar1986 gaGATATCGAGCTG<u>TTGACA</u>ATTAATCATCCGGCTCG<u>TATAAT</u>TTTAAAGAGGAGAAACAA

<u>ATGTTTGGTTTGATTGGGCACTCTACTAGTTTCG</u>AAGACGCCAAACGCAAGGCTT

CCTTGTTGGGTTTCGATACACATCGCTGATGGCGACTTGGACGTCTGGTGTACCGC

CCCCCCCCAGCTGGTAGAAAATGTTGAAGTGAAGAGCGCTAT

TGGCATTAGCATCGAAGGTAGTTACATTGATAGCTGTTTTGTT

CCCGAAATGTTAAGCCGCTTCAAGACCGCTCGCCGGAAAGTGC

TABLE 10-continued

Synthesized DNA segments

TGAATGCTATGGAGTTGGCCCAGAAAAAAGGTATCAATATCAC

CGCCTTGGGTGGTTTCACCTCCATTATCTTCGAAAATTTTAAC

CTGTTGCAGCACAAACAAATCCGGAACACCTCCCTGGAATGGG

AACGTTTTACCACCGGTAACACCCACACCGCGTGGGTGATTTG

TCGGCAACTGGAAATGAATGCCCCCAAAATTGGGATTGACTTG

AAATCCGCCACCGTGGCGGTGGTGGGCGCCACCGGTGACATTG

GCAGCGCCGTTTGTCGCTGGCTGATTAACAAAACCGGCATCGG

TGAGTTGTTGTTGGTAGCCCGGCAGAAGGAACCCTTAGATTCC

TTACAAAAAGAACTGGACGGGGGCACCATCAAAAATCTGGACG

AAGCCCTCCCCGAAGCGGACATTGTGGTGTGGGTCGCCAGTAT

GCCCAAGACCATGGAAATCGATGCGAATAACCTGAAACAGCCG

TGTTTGATGATTGATGGCGGTTACCCCAAAAACCTGGACGAGA

AATTTCAAGGCAACAACATCCATGTTGTAAAAGGTGGTATCGT

GCGCTTCTTCAATGACATTGGTTGGAACATGATGGAACTGGCC

GAAATGCAGAACCCCCAACGGGAAATGTTTGCGTGCTTCGCCG

AAGCTATGATCTTAGAGTTCGAAAAATGTCATACCAACTTCTC

TTGGGGTCGGAATAATATTAGTCTGGAAAAGATGGAGTTCATC

GGTGCCGCCAGCGTTAAACACGGCTTTTCCGCCATCGGCTTGGA

CAAGCACCCCAAAGTGTTAGCCGTCTAA

GAaCTGTTGACAATTgATCATCtGaCgCGTATAATTTTAAAGAGGAGAAACAA

ATGCAAACCCTGGAAAGCAATAAAAAAACCAACCTCGAAAACAGCATTGATCT

GCCCGATTTCACCACCGATAGTTATAAAGATGCCTATAGCCGGATCAACGCCA

TCGTGATTGAAGGGGAACAGGAAGCGCACGATAATTATATTTCCTTGGCTACC

CTGATCCCCAATGAACTGGAAGAATTAACCAAACTCGCCAAAATGGAACTGAA

ACACAAGCGGGGGTTCACCGCCTGCGGGCGCAATCTCGGCGTTCAAGCCGATA

TGATCTTCGCCAAAGAATTTTTTAGCAAATTGCACGGTAACTTTCAGGTGGCT

TTGAGCAATGGTAAAACCACCACCTGTCTCCTGATTCAGGCGATTCTGATTGA

AGCGTTCGCCATTTCCGCTTACCACGTTTATATTCGGGTGGCTGATCCCTTCG

CCAAGAAAATCACCCAAGGTGTCGTGAAAGACGAATACTTACACTTGAATTAT

GGGCAAGAATGGCTAAAGAAAATCTCGCCACCTGCAAAGATGAACTCATGGA

AGCTAACAAAGTGAATTTGCCCTTAATTAAGAAAATGTTGGATCAAGTTTCCG

AGGACGCGAGCGTACTGGCCATGGACCGTGAAGAACTGATGGAAGAATTCATG

ATCGCGTACCAGGACACCCTCTTGGAAATCGGCTTGGATAACCGCGAAATCG

CTCGGATGGCGATGGCGGCTATCGTGTAAGATATCag

P<sub>psbA2</sub> 7942orf_1593 P<sub>trc</sub> 7942orf_1594

AGatATcGCGTGCAAGGCCCAGTGATCAATTTCATTATTTTTCATTATTTCATCTCCATTGT

CCCTGAAAATCAGTTGTGTCGCCCCTCTACACAGCCCAGAACTATGGTAAAGGCGCACGAAA

AACCGCCAGGTAAACTCTTCTCAACCCCCAAAACGCCCTCTGTTTACCCATGGAAAAAACGA

CAATTACAAGAAAGTAAAACTTATGTCATCTATAAGCTTCGTGTATATTAACTTCCTGTTAC

TABLE 10-continued

Synthesized DNA segments

AAAGCTTTACAAAACTCTCATTAATCCTTTAGACTAAGTTTAGTCAGTTCCAATCTGAACgAAGGAATTATAACCAA

ATGCCGCAGCTTGAAGCCAGCCTTGAACTGGACTTTCAAAGCGAGTCCTACAAAGACGCTTAC

AGCCGCATCAACGCGATCGTGATTGAAGGCGAACAAGAGGCGTTCGACAACTACAATCGCCTT

GCTGAGATGCTGCCCGACCAGCGGGATGAGCTTCACAAGCTAGCCAAGATGGAACAGCGCCAC

ATGAAAGGCTTTATGGCCTGTGGCAAAAATCTCTCCGTCACTCCTGACATGGGTTTTGCCCAG

AAATTTTTCGAGCGCTTGCACGAGAACTTCAAAGCGGCGGCTGCGGAAGGCAAGGTCGTCACC

TGCCTACTGATTCAATCGCTAATCATCGAGTGCTTTGCGATCGCGGCTTACAACATCTACATC

CCAGTGGCGGATGCTTTTGCCCGCAAAATCACGGAGGGGTCGTGCGCGACGAATACCTGCAC

CGCAACTTCGGTGAAGAGTGGCTGAAGGCGAATTTTGATGCTTCCAAAGCCGAACTGGAAGAA

GCCAATCGTCAGAACCTGCCCTTGGTTTGGCTAATGCTCAACGAAGTGGCCGATGATGCTCGC

GAACTCGGGATGGAGCGTGAGTCGCTCGTCGAGGACTTTATGATTGCCTACGGTGAAGCTCTG

GAAAACATCGGCTTCACAACGCGCGAAATCATGCGTATGTCCGCCTATGGCCTTGCGGCCGTT

TGATCCAGGAAATCTGAATGTTCGGTCTTATCGGTCATCTCACCAGTTTGGAGCAGGCCCGCG

ACGTTTCTCGCAGGATGGGCTACGACGAATACGCCGATCAAGGATTGGAGTTTTGGAGTAGCG

CTCCTCCTCAAATCGTTGATGAAATC

ACAGTCACCAGTGCCACAGGCAAGGTGATTCACGGTCGCTACATCGAATCGTGTTTCTTGCCG

GAAATGCTGGCGGCGCGCCGCTTCAAAACAGCCACGCGCAAAGTTCTCAATGCCATGTCCCAT

GCCCAAAAACACGGCATCGACATCTCGGCCTTGGGGGCTTTACCTCGATTATTTTCGAGAAT

TTCGATTTGGCCAGTTTGCGGCAAGTGCGCGACACTACCTTGGAGTTTGAACGGTTCACCACC

GGCAATACTCACACGGCCTACGTAATCTGTAGACAGGTGGAAGCCGCTGCTAAAACGCTGGGC

ATCGACATTACCCAAGCGACAGTAGCGGTTGTCGGCGCGACTGGCGATATCGGTAGCGCTGTC

TGCCGCTGGCTCGACCTCAAACTGGGTGTCGGTGATTTGATCCTGACGGCGCGCAATCAGGAG

CGTTTGGATAACCTGCAGGCTGAACTCGGCCGGGGCAAGATTCTGCCCTTGGAAGCCGCTCTG

CCGGAAGCTGACTTTATCGTGTGGGTCGCCAGTATGCCTCAGGGCGTAGTGATCGACCCAGCA

ACCCTGAAGCAACCCTGCGTCCTAATCGACGGGGGCTACCCCAAAAACTTGGGCAGCAAAGTC

CAAGGTGAGGGCATCTATGTCCTCAATGGCGGGGTAGTTGAACATTGCTTCGACATCGACTGG

CAGATCATGTCCGCTGCAGAGATGGCGCGGCCCGAGCGCCAGATGTTTGCCTGCTTTGCCGAG

GCGATGCTCTTGGAATTTGAAGGCTGGCATACTAACTTCTCCTGGGGCCGCAACCAAATCACG

ATCGAGAAGATGGAAGCGATCGGTGAGGCATCGGTGCGCCACGGCTTCCAACCCTTGGCATTGGCAATTTGA

P<sub>psbA2</sub> aarBP-1  P<sub>trc</sub> adcBP-1

AGatATcGCGTGCAAGGCCCAGTGATCAATTTCATTATTTTTCATTATTTCATCTCCATTGTCC

CTGAAAATCAGTTGTGTCGCCCCTCTACACAGCCCAGAACTATGGTAAAGGCGCACGAAAAACC

GCCAGGTAAACTCTTCTCAACCCCCAAAACGCCCTCTGTTTACCCATGGAAAAAACGACAATTA

CAAGAAAGTAAAACTTATGTCATCTATAAGCTTCGTGTATATTAACTTCCTGTTACAAAGCTTGACAA

TTAATCATCCGGCTCGTATAATTTTAAAGAGGAGAAACAA

ATGTTCGGTTTAATCGGCCATCTGACTAGCCTGGAGCATGCGCAGGCCGTAGCCCACCA

ATTAGGTTATCCCGAATACGCCGACCAAGGTCTGGAGTTCTGGTGTATGGCGCCCCCCC

AAATTGTCGATGAAATTACTGTAACCAGCGTCACCGGCAAAACCATTTACGGCAAATAC

GTGGAATCTTGTTTTCTCCCCGAAATGTTGGCCAACCAACGCGTTAAGGCTGCTACCCG

TABLE 10-continued

Synthesized DNA segments

```
GAAAGTTATCAATGCGATGGCGCATGCTCAGAAACATAACATTGATATTACCGCTTTGG
GCGGCTTTAGTTCCATCATCTTCGAAAATTTTGATTTGGAGAAGATGAGCCATATTCGT
AATATTGAATTGGATTTTCGGCGGTTTACCACCGGTAACACCCACACCGCTTATATTAT
TTGCCAACAGATCGAACAAGCGGCTCCCCAAGTGGGCATCGATCTGCGGCAAGCTACCG
TTGCCGTGTGCGGTGCTACCGGTGACATTGGGTCTGCGGTATGTCGTTGGCTGAACACC
TGCCTCGATGTGCAAGATCTGTTGTTGGTGGCCCGTAATCGTGATCGGCTCTTAGAGTT
GCAAGCCGAACTGGGCCGTGGTAAAATTTTAGATTTGATGGAGGCCTTGCCCTTGGCTG
ATATTGTGGTATGGGTTGCCAGTATGCCTAAGGGCGTGGAATTGTCCATCGAACAATTG
AAACGCCCGAGTCTGATGATTGATGGTGGTTACCCCAAAAACATGGCCACCAAGATTCA
ACATCCGCAAATCCATGTTTTGAACGGCGGCATTGTTGAACACGCCTTAGATATTGATT
GGAAAATTATGGAAATTGTGAATATGGACGTCCCCTCCCGCCAGATGTTTGCTTGTTTT
GCTGAAGCGATGTTGCTGGAATTTGAAGGCTGGCACACCAACTTTTCCTGGGGTCGGAA
CCAAATCACCGTGGAAAAGATGCAACAAATTGGGGAAGTATCCCGTAAACACGGTTTCC
AACCCTTGTTATTAAACCCCCAATAA
GAGCTGTTGACAATTgATCATCaGGaTCGTATAATTTTAAAGAGGAGAAACA
ATGACCACCGCCACTGCCACCCCCGTTTTAGACTATCATTCCGATCGGTACAAAGACGCCTACAGTC
GCATCAACGCTATTGTCATTGAAGGCGAACAAGAGGCTCACGACAACTATATTGACTTGGCCAAATT
GTTGCCCCAACACCAAGAAGAATTAACCCGTTTGGCCAAAATGGAAGCCCGGCATAAGAAGGGTTTC
GAAGCTTGCGGGCGCAATTTGTCTGTTACCCCCGATATGGAATTCGCCAAAGCTTTCTTCGAAAAGC
TCCGTGCGAACTTCCAACGTGCTCTGGCCGAAGGTAAAACCGCCACCTGCCTCCTGATCCAAGCCCT
GATCATCGAATCCTTCGCCATCGCCGCGTACAATATCTACATTCCCATGGCCGACCCCTTTGCCCGT
AAAATTACCGAGTCCGTGGTCAAGGATGAATACTCCCATTTAAACTTCGGCGAAATCTGGTTGAAAG
AACACTTCGAATCCGTGAAAGGGGAACTGGAAGAAGCCAATCGGGCTAATCTCCCGCTGGTCTGGAA
GATGTTGAACCAGGTTGAGGCCGACGCGAAAGTATTAGGGATGGAAAAGGACGCCTTAGTCGAAGAC
TTTATGATTCAATACTCTGGTGCCTTGGAAAACATTGGCTTTACCACCCGCGAAATCATGAAGATGT
CTGTTTATGGGCTGACTGGTGCCtaaGATATCAG
```

Example 21

Growth of an SD Culture Started from a Single-Cell Descended Colony

The following example describes how to grow a mutant 6803 culture started from a single cell descended colony.

Part A—Starting from Plates.

1. From a single colony on a BG-11 plate use a sterile, 0.7 mm needle to scrape a 7 mm² patch onto a fresh BG-11 plate. Repeat this until multiple patches have been scraped onto the same plate. These patches can be considered as cells derived from an individual cell, which will be used to inoculate cultures for individual experiments.
2. Seal plates with parafilm and allow to grow at 31° C. with light at 50 mol photons $m^{-2}$ $sec^{-1}$ (Curtiss lab incubator conditions with 3 light bulbs on, the real light intensity will be measured by Michael) with plates face up for at least 2 days, but no more than two weeks.
3. Using a 2 mm loop, resuspend cells from a single cell derived patch and inoculate the cells using a pipette in 1 ml of fresh BG-11 to an O.D.$_{730}$ of at least 0.05-0.1 (an O.D. less than 0.05 will result in cell lysis and long lag phase). Vortex the tube until a homogenous solution is achieved (5-15 seconds). Vortexing time will vary depending on the adhesive qualities of each strain.
4. Grow cells at 31° C. with light at 50 mol photons $m^{-2}$ $sec^{-1}$ for 2 days. This culture can be expanded for large-scale experiments as follows in the downstairs Conviron chamber (140 mol photons $m^{-2}$ $sec^{-1}$, 30° C.): Dilute the culture into a larger volume down to an O.D.$_{730}$ of 0.05 or greater. For cultures less than 25 ml place on a shaker under normal growth conditions and agitate at a rate of 200-300 rpm. For cultures greater than 25 ml, bubbling of air is required until the culture reaches a density of at least $1 \times 10^7$ CFU/ml. At this density, air can be exchanged for 1% $CO_2$.

5. Grow cells at 30° C. with light at 140 mmol photons $m^{-2}$ $sec^{-1}$ (basement Conviron conditions) to the desired $O.D._{730}$ (for example, OD 0.2-0.4 for transformation of exogenous DNA).

Part B—Starting from Frozen Stock.
1. Spread frozen stock on a BG-11 agar plate (50 µg/ml Km BG-11 if with $Km^R$/sacB), and grow for 3-7 days.
2. Using sterile technique, scrape at least $5*10^6$ cells into 1 ml BG-11 media ($OD_{730nm}$ above 0.03). For slow growth strains, scrape at least $2*10^7$ cells ($OD_{730nm}$ above 0.12).
3. Proceed with step A-4 above. If cell density is high enough, the cells can be grown in 1 ml BG-11 for one day.

Example 22

Growth and Cell Damage Measurements

Bacterial growth in liquid culture was monitored spectrophotometrically or by flow cytometry and/or by plating. The relationship between 6803 culture optical density and cell density is used for conversion of optical density into cell density during growth. Staining with 5 µM SYTOX Green nucleic acid stain (Invitrogen Molecular Probes, Inc. OR, USA) for 5 min was used to detect damaged cells. Cells were observed under an Axioskop40 fluorescence microscope (Zeiss, Germany). Green cells are sorted in a FACSAria flow cytometer (BD Biosciences, CA, USA) and counted as damaged.

Example 23

Lipids Separation and Measurement

The FFAs in the medium are quantitatively separated from the culture medium by hexane, which is unable to release FFAs and other lipids from intact 6803 cells. One hundred mL of culture is acidified by 2 mL $H_3PO_4$ (1M) containing 1 g NaCl, and extracted with 100 mL hexane. For the unsecreted intracellular FFAs, the cells are extracted by the Folch method for total lipids. The FFA samples were analyzed by gas chromatography (GC) analysis.

GC was performed to determine the FFA amount in the hexane extracts. After 6000 g×10 min centrifuge, 5 ml hexane was taken out from the upper organic layer, filled in a glass tube (13×100 mm, Fisherbrand), dried on a nitrogen evaporator (N-EVAP111, Organomation Associates Inc.). The dried samples were then re-dissolved by a known volume of hexane and analyzed by gas chromatography (Shimadzu GC 2010) equipped with a Supelco Nukol capillary column (30 m×0.53 mm×0.50 µm) and flame ionization detector (FID).

For the unsecreted intracellular FFAs, the cells are collected by centrifugation, and extracted by the Folch method for total lipids. The intracellular unsecreted FFA were extracted from the cell pellet after hexane extraction, and calculated with the final cell density.

GC operating conditions were as follows: split ratio 1:5; inject volume 1 µL; helium carrier gas with constant flow rate 30 ml/min; $H_2$ 40 ml/min, Air 400 ml/min, make up gas (helium) 5 ml/min; injector and detector temperature 250° C.; and oven temperature started at 150° C. and increased at a rate of 10° C./min to 220° C. and held for 10 min. Each FFA compound was identified by comparing its retention time with that of standard (Sigma, St. Louis, Mo.). Compound concentrations in samples were quantified based on the area under the chromatogram peak in comparison with the standards.

Example 24

Transmission Electron Microscopy Analysis

Figure 26:
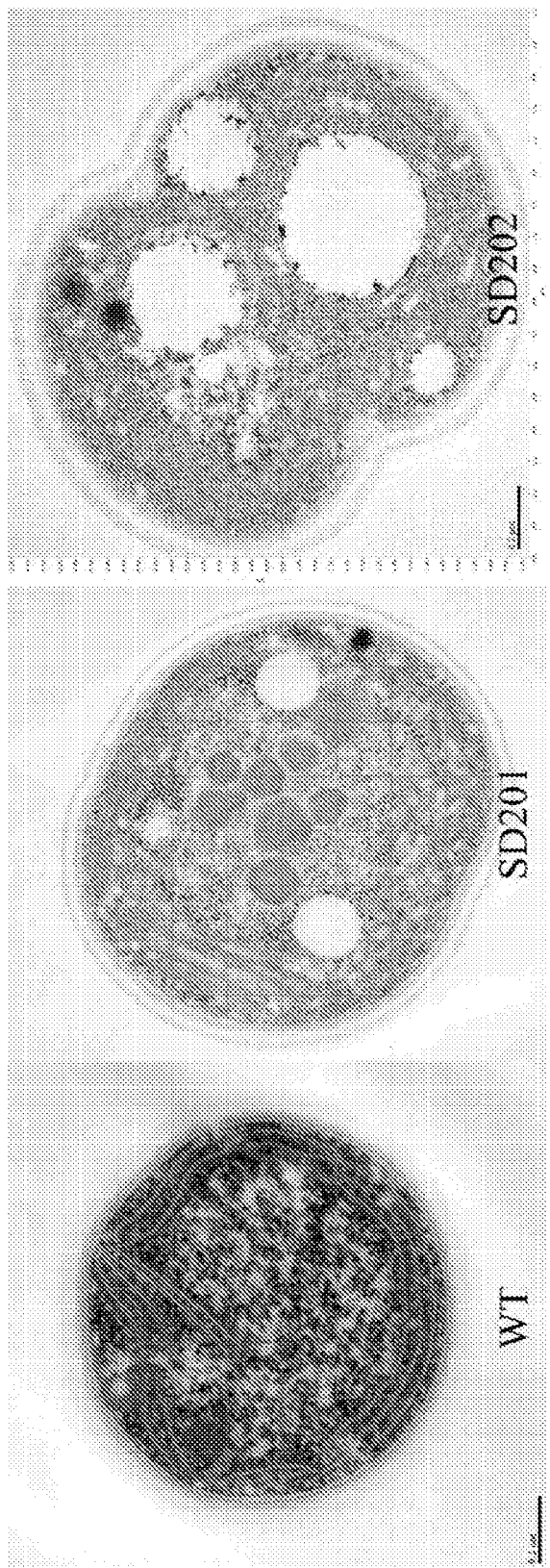
FIG. 26 depicts TEM images of wild-type (A), SD201 (B) and SD202 (C). The white vacuoles inside the cell indicate the presence of neutral lipid droplets.

The triglyceride inclusion droplets in cyanobacterial cells were visualized by transmission electron microscopy (TEM). A specific cell fixation procedure for *Synechocystis* sp. PCC 6803 and mutant strains is shown below. All steps are at room temperature unless noted. Initial steps may be done in Eppendorf tubes. Typically, the protocol proceeds through the following steps:
1. Primary fix, for the fixation of proteins, cells in suspension with 2% glutaraldehyde in 50 mM $KH_2PO_4$—$K_2HPO_4$ buffer, pH 6.8 for 2 hours or overnight at 4° C. Wash fixed cells, pellet cells, decant fixative, resuspend cells in approx 1 ml of the same buffer, invert tube for a few minutes, and wash 3 times.
2. Solidify cells in agarose, pellet and decant wash buffer. Resuspend in approx 50-100 µl of buffer. Pipet cells from tube and put on a small piece of parafilm. Add equal vol of 2% agarose (melt, and then cool to near-solidification point). Pipet cells-agarose mixtures. Cut into 4-5 small chunks with lancet or shaver and transfer to a glass vial, wash with buffer, allow sitting for 15 min. Repeat wash two times.
3. Secondary fix, for the lipid fixation, in 1% osmium tetroxide in $KH_2PO_4$—$K_2HPO_4$ buffer for 2 h. Remove secondary fix solution. Wash 3 times with buffer, then 3 times with de-ionized $H_2O$, 15 min per step.
4. Uranyl block stain with 2% aqueous uranyl acetate for 2 hours at room temperature or overnight at 4° C. Wash 3 times with $H_2O$, 15 min each. Remove uranyl acetate. Dehydrate samples through the following ethanol series, 5-10 min each step: 20%, 50%, 75%, 95%, and 100% EtOH 3 times, then in 1:1 EtOH:acetone 2 times. Lead block stain. Incubate 1 h at room temperature in a saturated solution of lead acetate in 1:1 EtOH:acetone. Wash samples 2 times for 15 min in 1:1 EtOH:acetone, then 2 times 15 min in acetone.
5. Infiltrate with increasing epoxy resin (Spurr's resin, firm mixture) series, 25% increments, using 100% resin 3 times. Place vials on rotary wheel during all these steps. Specifically, 25%, 50% steps minimum of 4 hours; 75% and 100% steps for a minimum of 6 hours.
6. Polymerization. After 3rd 100% resin step, embed cell-chunks in flat molds using fresh resin. Put in oven at 60° C. for 24-36 hours. The polymerized modes need to be trimmed first and cut into sections in a microtome. Sections on grids would be post stained if necessary, and then can be checked under TE The transmission electronic microscopy (TEM) images of SD201 and SD202 (FIG. 26) showing that the TAG-producing *Synechocystis* strains accumulate significant triglyceride droplets.

Example 25

Optimizing the Codons in Non-6803 Genes for Optimal Expression in 6803

The expression levels of a foreign gene can be optimized for a host cell by changing the gene's low frequency use codons into high frequency use codons. Table 11 shows the codons usage bias for the highly expressed genes in 6803.

Based on the codon usage frequencies, the low frequency use codons were replaced. Codons for the non-6803 genes were also changed to adjust their GC content to around 48%, which is the general GC content for 6803 genes.

Finally, according to the mRNA structures predicted by RNAfold WebServer (rna.tbi.univie.ac.at/cgi-bin/RNAfold.cgi), the mRNA secondary structures of the non-6803 genes were optimized to interrupt the stable stem-loop structures by changing the codons, which may impede the translation process of ribosome. After the transcription of a foreign gene in a bacterium, the mRNA might form stem-loop structures, which are readily cleaved by RNase, resulting in degradation of the mRNA.

As stated above, the codon-optimized non-6803 genes were synthesized and cloned into pUC57 by GenScript Corp (NJ, USA). The redesigned and synthesized DNA segments are listed in Table 10.

TABLE 11

Codon usage frequencies in the Top-40 highly expressed 6803 genes.

| Codon | Amino Acid | Relative % within AA | Codon Count | % within Total |
|---|---|---|---|---|
| GCA | A | 5.60% | 107 | 0.52% |
| GCC | A | 53.30% | 1024 | 5.01% |
| GCG | A | 13.10% | 252 | 1.23% |
| GCT | A | 28.00% | 538 | 2.63% |
| TGC | C | 41.20% | 61 | 0.30% |
| TGT | C | 58.80% | 87 | 0.43% |
| GAC | D | 49.50% | 555 | 2.72% |
| GAT | D | 50.50% | 566 | 2.77% |
| GAA | E | 79.60% | 1080 | 5.29% |
| GAG | E | 20.40% | 276 | 1.35% |
| TTC | F | 52.80% | 443 | 2.17% |
| TTT | F | 47.20% | 396 | 1.94% |
| GGA | G | 8.60% | 151 | 0.74% |
| GGC | G | 31.80% | 561 | 2.75% |
| GGG | G | 15.90% | 280 | 1.37% |
| GGT | G | 43.80% | 773 | 3.78% |
| CAC | H | 68.70% | 276 | 1.35% |
| CAT | H | 31.30% | 126 | 0.62% |
| ATA | I | 0.60% | 8 | 0.04% |
| ATC | I | 42.40% | 566 | 2.77% |
| ATT | I | 57.00% | 760 | 3.72% |
| AAA | K | 68.90% | 713 | 3.49% |
| AAG | K | 31.10% | 322 | 1.58% |
| CTA | L | 9.30% | 175 | 0.86% |
| CTC | L | 20.50% | 386 | 1.89% |

TABLE 11-continued

Codon usage frequencies in the Top-40 highly expressed 6803 genes.

| Codon | Amino Acid | Relative % within AA | Codon Count | % within Total |
|---|---|---|---|---|
| CTG | L | 23.30% | 439 | 2.15% |
| CTT | L | 7.80% | 147 | 0.72% |
| TTA | L | 10.50% | 197 | 0.96% |
| TTG | L | 28.60% | 539 | 2.64% |
| ATG | M | 100.00% | 478 | 2.34% |
| AAC | N | 60.10% | 475 | 2.33% |
| AAT | N | 39.90% | 315 | 1.54% |
| CCA | P | 6.00% | 57 | 0.28% |
| CCC | P | 64.10% | 607 | 2.97% |
| CCG | P | 11.60% | 110 | 0.54% |
| CCT | P | 18.30% | 173 | 0.85% |
| CAA | Q | 62.40% | 469 | 2.30% |
| CAG | Q | 37.60% | 283 | 1.39% |
| AGA | R | 1.90% | 20 | 0.10% |
| AGG | R | 2.80% | 29 | 0.14% |
| CGA | R | 4.20% | 44 | 0.22% |
| CGC | R | 28.00% | 294 | 1.44% |
| CGG | R | 36.70% | 385 | 1.89% |
| CGT | R | 26.50% | 278 | 1.36% |
| AGC | S | 20.70% | 224 | 1.10% |
| AGT | S | 13.20% | 143 | 0.70% |
| TCA | S | 1.90% | 21 | 0.10% |
| TCC | S | 45.30% | 491 | 2.40% |
| TCG | S | 4.80% | 52 | 0.25% |
| TCT | S | 14.10% | 153 | 0.75% |
| ACA | T | 4.30% | 48 | 0.24% |
| ACC | T | 69.80% | 776 | 3.80% |
| ACG | T | 8.90% | 99 | 0.48% |
| ACT | T | 17.00% | 189 | 0.93% |
| GTA | V | 17.60% | 271 | 1.33% |
| GTC | V | 17.20% | 264 | 1.29% |
| GTG | V | 39.50% | 608 | 2.98% |
| GTT | V | 25.70% | 395 | 1.93% |
| TGG | W | 100.00% | 252 | 1.23% |
| TAC | Y | 61.40% | 355 | 1.74% |

TABLE 11-continued

Codon usage frequencies in the Top-40 highly expressed 6803 genes.

| Codon | Amino Acid | Relative % within AA | Codon Count | % within Total |
|---|---|---|---|---|
| TAT | Y | 38.60% | 223 | 1.09% |
| TAA | * | 52.60% | 20 | 0.10% |
| TAG | * | 47.40% | 18 | 0.09% |
| TGA | * | 0.00% | 0 | 0.00% |

---

What is claimed is:

1. A cyanobacterium, wherein the cyanobacterium:
   (a) expresses at least one nucleic acid encoding an acyl carrier protein (ACP) thioesterase (TE);
   (b) overexpresses one or more nucleic acids encoding an acyl-CoA ligase (ACL); and
   (c) inducibly expresses at least one nucleic acid encoding a neutral lipid synthase,
   such that the cyanobacterium is capable of synthesizing fatty acyl methyl esters (FAME) or fatty acyl ethyl esters (FAEE) in a culture upon addition of short alcohols to the culture.

2. The cyanobacterium of claim 1, wherein the cyanobacterium further comprises a mutation that disrupts a native functional lipase that catalyzes the hydrolysis of a neutral lipid.

3. The cyanobacterium of claim 2, wherein the lipase is fipA.

4. The cyanobacterium of claim 1, further comprising an inducible promoter operably-linked to a nucleic acid encoding at least one protein capable of hydrolyzing the lipid membranes of the bacterium and at least one endolysin protein.

5. The cyanobacterium of claim 4, wherein the inducible promoter is induced by the lack of $CO_2$.

6. The cyanobacterium of claim 4, wherein the at least one protein capable of hydrolyzing the lipid membranes is selected from the group consisting of galactolipase, phospholipase B, and a lipase.

7. The cyanobacterium of claim 1, further comprising
   (a) a first nucleic acid, wherein the first nucleic acid comprises a first inducible promoter operably-linked to a nucleic acid encoding at least one protein capable of hydrolyzing the lipid membranes of the bacterium; and
   (b) a second nucleic acid, wherein the second nucleic acid comprises a second promoter operably-linked to a nucleic acid encoding at least one endolysin protein.

8. The cyanobacterium of claim 1, wherein:
   (a) the at least on nucleic acid encoding an ACP TE is selected from the group consisting of tesA and fatB;
   (b) the one or more nucleic acids encoding an ACL nucleic acid is selected from the group consisting of fadD and faa2; and
   (c) the at least one nucleic acid encoding a neutral lipid synthase is selected from the group consisting of atfA and a homolog thereof.

9. The cyanobacterium of claim 8, wherein:
   (a) the at least on nucleic acid encoding an ACP TE is tesA operably-linked to a constitutive promoter;
   (b) the one or more nucleic acids encoding an ACL nucleic acid is fadD fadA operably-linked to a constitutive promoter; and
   (c) the at least one nucleic acid encoding a neutral lipid synthase is atfA operably-linked to an inducible promoter.

10. The cyanobacterium of claim 9, wherein the tesA, fadD and/or atfA nucleic acid is codon-optimized.

11. The cyanobacterium of claim 1, wherein the short alcohol is selected from the group consisting of methanol and ethanol.

12. The cyanobacterium of claim 1, further comprising exogenous expression of pyruvate decarboxylase and alcohol dehydrogenase such that the cyanobacterium is capable of synthesizing fatty acyl ethyl esters (FAEE) in a culture without the addition of ethanol to the culture.

13. A method for releasing neutral lipids from a cyanobacterium, the method comprising
   (a) altering the cyanobacterium, wherein the cyanobacterium (i) expresses at least one nucleic acid encoding an acyl carrier protein (ACP) thioesterase (TE); (ii) overexpresses one or more nucleic acids encoding an acyl-CoA ligase (ACL); and (iii) inducibly expresses at least one nucleic acid encoding a neutral lipid synthase, such that the cyanobacterium is capable of synthesizing fatty acyl methyl esters (FAME) or fatty acyl ethyl esters (FAEE) in a culture upon addition of short alcohols to the culture;
   (b) introducing into the bacterium a nucleic acid comprising an inducible promoter operably-linked to a nucleic acid, the nucleic acid encoding at least one protein capable of hydrolyzing the lipid membranes of the bacterium and at least one endolysin protein; and
   (c) inducing the promoter to express both the protein capable of hydrolyzing the lipid membranes and the endolysin, wherein the protein capable of hydrolyzing the lipid membranes frees fatty acids from the lipid membranes of the cyanobacterium and allows the endolysin to degrade the peptidoglcan layer of the cell wall.

14. The method of claim 13, wherein the neutral lipid synthase is a triglyceride synthase.

15. The method of claim 13, wherein the cyanobacterium comprises a nucleic acid encoding a lipid body protein.

16. The method of claim 13, wherein the lipid body protein is a phasing protein.

17. The method of claim 13, wherein the cyanobacterium further comprises a mutation that disrupts a native functional lipase that catalyzes the hydrolysis of a neutral lipid.

18. The method of claim 13, wherein the inducible promoter is induced by the lack of $CO_2$.

* * * * *

UNITED STATES PATENT AND TRADEMARK OFFICE
CERTIFICATE OF CORRECTION

| | | |
|---|---|---|
| PATENT NO. | : 9,255,283 B2 | Page 1 of 1 |
| APPLICATION NO. | : 13/805733 | |
| DATED | : February 9, 2016 | |
| INVENTOR(S) | : Roy Curtiss, III et al. | |

It is certified that error appears in the above-identified patent and that said Letters Patent is hereby corrected as shown below:

IN THE SPECIFICATION

Column 1 Line 4 the following paragraph should be inserted after the title and prior to the REFERENCE TO SEQUENCE LISTING:

--GOVERNMENTAL RIGHTS
This invention was made with government support under DE-AR0000011 awarded by the Department of Energy. The government has certain rights in the invention.--

Signed and Sealed this
Third Day of May, 2016

Michelle K. Lee
*Director of the United States Patent and Trademark Office*

SEQUENCE LISTING

```
<160> NUMBER OF SEQ ID NOS: 136

<210> SEQ ID NO 1
<211> LENGTH: 27
<212> TYPE: DNA
<213> ORGANISM: Artificial Sequence
<220> FEATURE:
<223> OTHER INFORMATION: SYNECHOCYSTIS

<400> SEQUENCE: 1
gcgagctcca gacgactacg ggcaaag                                         27

<210> SEQ ID NO 2
<211> LENGTH: 34
<212> TYPE: DNA
<213> ORGANISM: Artificial Sequence
<220> FEATURE:
<223> OTHER INFORMATION: SYNECHOCYSTIS

<400> SEQUENCE: 2
atgtttttct ggcatcacac cacctcaaat tggg                                 34

<210> SEQ ID NO 3
<211> LENGTH: 33
<212> TYPE: DNA
<213> ORGANISM: Artificial Sequence
<220> FEATURE:
<223> OTHER INFORMATION: SYNECHOCYSTIS

<400> SEQUENCE: 3
ttgaggtggt gtgatgccag aaaaacatga tct                                  33

<210> SEQ ID NO 4
<211> LENGTH: 28
<212> TYPE: DNA
<213> ORGANISM: Artificial Sequence
<220> FEATURE:
<223> OTHER INFORMATION: SYNECHOCYSTIS

<400> SEQUENCE: 4
gaccgcggtt attttaagca ctgactcc                                        28

<210> SEQ ID NO 5
<211> LENGTH: 27
<212> TYPE: DNA
<213> ORGANISM: Artificial Sequence
<220> FEATURE:
<223> OTHER INFORMATION: SYNECHOCYSTIS

<400> SEQUENCE: 5
ggccgcggaa agccacgttg tgtctca                                         27

<210> SEQ ID NO 6
```

```
<211> LENGTH: 33
<212> TYPE: DNA
<213> ORGANISM: Artificial Sequence
<220> FEATURE:
<223> OTHER INFORMATION: SYNECHOCYSTIS

<400> SEQUENCE: 6
accccctggg gcagaaagcc acgttgtgtc tca                              33

<210> SEQ ID NO 7
<211> LENGTH: 34
<212> TYPE: DNA
<213> ORGANISM: Artificial Sequence
<220> FEATURE:
<223> OTHER INFORMATION: SYNECHOCYSTIS

<400> SEQUENCE: 7
acaacgtggc tttctgcccc aggggggtttc ttga                            34

<210> SEQ ID NO 8
<211> LENGTH: 27
<212> TYPE: DNA
<213> ORGANISM: Artificial Sequence
<220> FEATURE:
<223> OTHER INFORMATION: SYNECHOCYSTIS

<400> SEQUENCE: 8
gggatccgtt ggttagccaa gagaatc                                    27

<210> SEQ ID NO 9
<211> LENGTH: 31
<212> TYPE: DNA
<213> ORGANISM: Artificial Sequence
<220> FEATURE:
<223> OTHER INFORMATION: SYNECHOCYSTIS

<400> SEQUENCE: 9
gacatatgtt actgctgatt tgcatcatcg a                               31

<210> SEQ ID NO 10
<211> LENGTH: 31
<212> TYPE: DNA
<213> ORGANISM: Artificial Sequence
<220> FEATURE:
<223> OTHER INFORMATION: SYNECHOCYSTIS

<400> SEQUENCE: 10
gatctagaca cattgctcct tttgtgcgta a                               31

<210> SEQ ID NO 11
<211> LENGTH: 32
<212> TYPE: DNA
<213> ORGANISM: Artificial Sequence
<220> FEATURE:
<223> OTHER INFORMATION: SYNECHOCYSTIS

<400> SEQUENCE: 11
gaccgcggaa ctaatggctt gggctaggta ta                              32

<210> SEQ ID NO 12
<211> LENGTH: 28
<212> TYPE: DNA
<213> ORGANISM: Artificial Sequence
<220> FEATURE:
<223> OTHER INFORMATION: SYNECHOCYSTIS

<400> SEQUENCE: 12
```

```
gaggtaccgc caattgcaga cgactacg                                28

<210> SEQ ID NO 13
<211> LENGTH: 31
<212> TYPE: DNA
<213> ORGANISM: Artificial Sequence
<220> FEATURE:
<223> OTHER INFORMATION: SYNECHOCYSTIS

<400> SEQUENCE: 13
gatctagaca cattgctcct tttgtgcgta a                            31

<210> SEQ ID NO 14
<211> LENGTH: 32
<212> TYPE: DNA
<213> ORGANISM: Artificial Sequence
<220> FEATURE:
<223> OTHER INFORMATION: SYNECHOCYSTIS

<400> SEQUENCE: 14
gaccgcggaa ctaatggctt gggctaggta ta                           32

<210> SEQ ID NO 15
<211> LENGTH: 25
<212> TYPE: DNA
<213> ORGANISM: Artificial Sequence
<220> FEATURE:
<223> OTHER INFORMATION: SYNECHOCYSTIS

<400> SEQUENCE: 15
aggcatgcgt tggttagcca agaga                                   25

<210> SEQ ID NO 16
<211> LENGTH: 39
<212> TYPE: DNA
<213> ORGANISM: Artificial Sequence
<220> FEATURE:
<223> OTHER INFORMATION: SYNECHOCYSTIS

<400> SEQUENCE: 16
gcacaaaagg agcaatgtgt tattttaagc actgactcc                    39

<210> SEQ ID NO 17
<211> LENGTH: 36
<212> TYPE: DNA
<213> ORGANISM: Artificial Sequence
<220> FEATURE:
<223> OTHER INFORMATION: SYNECHOCYSTIS

<400> SEQUENCE: 17
tcagtgctta aaataacaca ttgctccttt tgtgcg                       36

<210> SEQ ID NO 18
<211> LENGTH: 29
<212> TYPE: DNA
<213> ORGANISM: Artificial Sequence
<220> FEATURE:
<223> OTHER INFORMATION: SYNECHOCYSTIS

<400> SEQUENCE: 18
caaactaatg gcttgggcta ggtatagct                               29

<210> SEQ ID NO 19
<211> LENGTH: 35
<212> TYPE: DNA
```

<213> ORGANISM: Artificial Sequence
<220> FEATURE:
<223> OTHER INFORMATION: SYNECHOCYSTIS

<400> SEQUENCE: 19 catgttttc tggcatcaca ccacctcaaa ttggg                          35

<210> SEQ ID NO 20
<211> LENGTH: 30
<212> TYPE: DNA
<213> ORGANISM: Artificial Sequence
<220> FEATURE:
<223> OTHER INFORMATION: SYNECHOCYSTIS

<400> SEQUENCE: 20
aggtggtgtg atgccagaaa aacatgacct                               30

<210> SEQ ID NO 21
<211> LENGTH: 39
<212> TYPE: DNA
<213> ORGANISM: Artificial Sequence
<220> FEATURE:
<223> OTHER INFORMATION: SYNECHOCYSTIS

<400> SEQUENCE: 21
acaaaaggag caatgtgcta tctgcactgc tcattaata                     39

<210> SEQ ID NO 22
<211> LENGTH: 32
<212> TYPE: DNA
<213> ORGANISM: Artificial Sequence
<220> FEATURE:
<223> OTHER INFORMATION: SYNECHOCYSTIS

<400> SEQUENCE: 22
agtgcagata gcacattgct cctttgtgc gt                             32

<210> SEQ ID NO 23
<211> LENGTH: 32
<212> TYPE: DNA
<213> ORGANISM: Artificial Sequence
<220> FEATURE:
<223> OTHER INFORMATION: SYNECHOCYSTIS

<400> SEQUENCE: 23
gaccgcggaa ctaatggctt gggctaggta ta                            32

<210> SEQ ID NO 24
<211> LENGTH: 68
<212> TYPE: DNA
<213> ORGANISM: Artificial Sequence
<220> FEATURE:
<223> OTHER INFORMATION: SYNECHOCYSTIS

<400> SEQUENCE: 24
atcatatgaa gacaaacgaa agccccacc tagcgtcatg ccgggtgggg gcttttcat  60 ctgcagta                                                       68

<210> SEQ ID NO 25
<211> LENGTH: 68
<212> TYPE: DNA
<213> ORGANISM: Artificial Sequence
<220> FEATURE:
<223> OTHER INFORMATION: SYNECHOCYSTIS

<400> SEQUENCE: 25

-continued

```
tactgcagat gaaaaagccc ccacccggca tgacgctagg tgggggcttt cgtttgtctt    60
catatgat                                                              68

<210> SEQ ID NO 26
<211> LENGTH: 23
<212> TYPE: DNA
<213> ORGANISM: Artificial Sequence
<220> FEATURE:
<223> OTHER INFORMATION: SYNECHOCYSTIS

<400> SEQUENCE: 26
ctgcagatga aaagccccc acc                                              23

<210> SEQ ID NO 27
<211> LENGTH: 28
<212> TYPE: DNA
<213> ORGANISM: Artificial Sequence
<220> FEATURE:
<223> OTHER INFORMATION: SYNECHOCYSTIS

<400> SEQUENCE: 27
gaggatccta attgtatgcc cgactatt                                        28

<210> SEQ ID NO 28
<211> LENGTH: 37
<212> TYPE: DNA
<213> ORGANISM: Artificial Sequence
<220> FEATURE:
<223> OTHER INFORMATION: SYNECHOCYSTIS

<400> SEQUENCE: 28
actgctgatt tgcatcattt ggttataatt ccttatg                              37

<210> SEQ ID NO 29
<211> LENGTH: 36
<212> TYPE: DNA
<213> ORGANISM: Artificial Sequence
<220> FEATURE:
<223> OTHER INFORMATION: SYNECHOCYSTIS

<400> SEQUENCE: 29
gaattataac caaatgatgc aaatcagcag taacgg                               36

<210> SEQ ID NO 30
<211> LENGTH: 29
<212> TYPE: DNA
<213> ORGANISM: Artificial Sequence
<220> FEATURE:
<223> OTHER INFORMATION: SYNECHOCYSTIS

<400> SEQUENCE: 30
gaggatcctt attttaagca ctgactcct                                       29

<210> SEQ ID NO 31
<211> LENGTH: 27
<212> TYPE: DNA
<213> ORGANISM: Artificial Sequence
<220> FEATURE:
<223> OTHER INFORMATION: SYNECHOCYSTIS

<400> SEQUENCE: 31
gacatatgcc agaaaaacat gacctgt                                         27

<210> SEQ ID NO 32
```

<210> SEQ ID NO 32
<211> LENGTH: 26
<212> TYPE: DNA
<213> ORGANISM: Artificial Sequence
<220> FEATURE:
<223> OTHER INFORMATION: SYNECHOCYSTIS

<400> SEQUENCE: 32
agaagctttg tggcccaaca attggt                                    26

<210> SEQ ID NO 33
<211> LENGTH: 29
<212> TYPE: DNA
<213> ORGANISM: Artificial Sequence
<220> FEATURE:
<223> OTHER INFORMATION: SYNECHOCYSTIS

<400> SEQUENCE: 33
gtgaattctg taagcagtta gagtggccc                                 29

<210> SEQ ID NO 34
<211> LENGTH: 28
<212> TYPE: DNA
<213> ORGANISM: Artificial Sequence
<220> FEATURE:
<223> OTHER INFORMATION: SYNECHOCYSTIS

<400> SEQUENCE: 34
cggtctactc cggttaaatc ccctaacg                                  28

<210> SEQ ID NO 35
<211> LENGTH: 25
<212> TYPE: DNA
<213> ORGANISM: Artificial Sequence
<220> FEATURE:
<223> OTHER INFORMATION: SYNECHOCYSTIS

<400> SEQUENCE: 35
ccacagcccc aacaataagc aagat                                     25

<210> SEQ ID NO 36
<211> LENGTH: 27
<212> TYPE: DNA
<213> ORGANISM: Artificial Sequence
<220> FEATURE:
<223> OTHER INFORMATION: SYNECHOCYSTIS

<400> SEQUENCE: 36
gacatatgcc agaaaacat gacctgt                                    27

<210> SEQ ID NO 37
<211> LENGTH: 37
<212> TYPE: DNA
<213> ORGANISM: Artificial Sequence
<220> FEATURE:
<223> OTHER INFORMATION: SYNECHOCYSTIS

<400> SEQUENCE: 37
gacatatgag gaggtgtgat gccagaaaaa catgacc                        37

<210> SEQ ID NO 38
<211> LENGTH: 37
<212> TYPE: DNA
<213> ORGANISM: Artificial Sequence
<220> FEATURE:
<223> OTHER INFORMATION: SYNECHOCYSTIS

<400> SEQUENCE: 38
actgctgatt tgcatcattt ggttataatt ccttatg					37

<210> SEQ ID NO 39
<211> LENGTH: 36
<212> TYPE: DNA
<213> ORGANISM: Artificial Sequence
<220> FEATURE:
<223> OTHER INFORMATION: SYNECHOCYSTIS

<400> SEQUENCE: 39
gaattataac caaatgatgc aaatcagcag taacgg					36

<210> SEQ ID NO 40
<211> LENGTH: 23
<212> TYPE: DNA
<213> ORGANISM: Artificial Sequence
<220> FEATURE:
<223> OTHER INFORMATION: SYNECHOCYSTIS

<400> SEQUENCE: 40
taaactctgt aggccagcgg caa					23

<210> SEQ ID NO 41
<211> LENGTH: 26
<212> TYPE: DNA
<213> ORGANISM: Artificial Sequence
<220> FEATURE:
<223> OTHER INFORMATION: SYNECHOCYSTIS

<400> SEQUENCE: 41
cgtcaatgcc tagacctagc agtacc					26

<210> SEQ ID NO 42
<211> LENGTH: 27
<212> TYPE: DNA
<213> ORGANISM: Artificial Sequence
<220> FEATURE:
<223> OTHER INFORMATION: SYNECHOCYSTIS

<400> SEQUENCE: 42
aaggatttcc gttttatccc agcacca					27

<210> SEQ ID NO 43
<211> LENGTH: 27
<212> TYPE: DNA
<213> ORGANISM: Artificial Sequence
<220> FEATURE:
<223> OTHER INFORMATION: SYNECHOCYSTIS

<400> SEQUENCE: 43
gtaattgcca cagacaagcg tattcgg					27

<210> SEQ ID NO 44
<211> LENGTH: 33
<212> TYPE: DNA
<213> ORGANISM: Artificial Sequence
<220> FEATURE:
<223> OTHER INFORMATION: SYNECHOCYSTIS

<400> SEQUENCE: 44
accatatgca tcctaggcct attaatattc cgg					33

<210> SEQ ID NO 45
<211> LENGTH: 25
<212> TYPE: DNA

```
<213> ORGANISM: Artificial Sequence
<220> FEATURE:
<223> OTHER INFORMATION: SYNECHOCYSTIS

<400> SEQUENCE: 45
gaattaggat ccgtcgacct gcagg                                    25

<210> SEQ ID NO 46
<211> LENGTH: 27
<212> TYPE: DNA
<213> ORGANISM: Artificial Sequence
<220> FEATURE:
<223> OTHER INFORMATION: SYNECHOCYSTIS

<400> SEQUENCE: 46
gagaattcca gacgactacg ggcaaag                                  27

<210> SEQ ID NO 47
<211> LENGTH: 31
<212> TYPE: DNA
<213> ORGANISM: Artificial Sequence
<220> FEATURE:
<223> OTHER INFORMATION: SYNECHOCYSTIS

<400> SEQUENCE: 47
aacgtgtccg ccatcacacc acctcaaatt g                             31

<210> SEQ ID NO 48
<211> LENGTH: 31
<212> TYPE: DNA
<213> ORGANISM: Artificial Sequence
<220> FEATURE:
<223> OTHER INFORMATION: SYNECHOCYSTIS

<400> SEQUENCE: 48
gaggtggtgt gatggcggac acgttattga t                             31

<210> SEQ ID NO 49
<211> LENGTH: 36
<212> TYPE: DNA
<213> ORGANISM: Artificial Sequence
<220> FEATURE:
<223> OTHER INFORMATION: SYNECHOCYSTIS

<400> SEQUENCE: 49
caaaaggagc aatgtgttat ttgtcatcat cgtctt                        36

<210> SEQ ID NO 50
<211> LENGTH: 35
<212> TYPE: DNA
<213> ORGANISM: Artificial Sequence
<220> FEATURE:
<223> OTHER INFORMATION: SYNECHOCYSTIS

<400> SEQUENCE: 50
gatgatgaca ataacacat tgctcctttt gtgcg                          35

<210> SEQ ID NO 51
<211> LENGTH: 26
<212> TYPE: DNA
<213> ORGANISM: Artificial Sequence
<220> FEATURE:
<223> OTHER INFORMATION: SYNECHOCYSTIS

<400> SEQUENCE: 51
acggatccgc aagcagtgaa agatag                                   26
```

<210> SEQ ID NO 52
<211> LENGTH: 27
<212> TYPE: DNA
<213> ORGANISM: Artificial Sequence
<220> FEATURE:
<223> OTHER INFORMATION: SYNECHOCYSTIS

<400> SEQUENCE: 52
caaatggcgg acacgttatt gattctg                                    27

<210> SEQ ID NO 53
<211> LENGTH: 34
<212> TYPE: DNA
<213> ORGANISM: Artificial Sequence
<220> FEATURE:
<223> OTHER INFORMATION: SYNECHOCYSTIS

<400> SEQUENCE: 53
ctttgtagtc tgagtcatga tttactaaag gctg                            34

<210> SEQ ID NO 54
<211> LENGTH: 26
<212> TYPE: DNA
<213> ORGANISM: Artificial Sequence
<220> FEATURE:
<223> OTHER INFORMATION: SYNECHOCYSTIS

<400> SEQUENCE: 54
attataacca aatggcggac acgtta                                     26

<210> SEQ ID NO 55
<211> LENGTH: 24
<212> TYPE: DNA
<213> ORGANISM: Artificial Sequence
<220> FEATURE:
<223> OTHER INFORMATION: SYNECHOCYSTIS

<400> SEQUENCE: 55
tccccattgc cccaaaatac atcc                                       24

<210> SEQ ID NO 56
<211> LENGTH: 35
<212> TYPE: DNA
<213> ORGANISM: Artificial Sequence
<220> FEATURE:
<223> OTHER INFORMATION: SYNECHOCYSTIS

<400> SEQUENCE: 56
caataacgtg tccgccattt ggttataatt cctta                           35

<210> SEQ ID NO 57
<211> LENGTH: 27
<212> TYPE: DNA
<213> ORGANISM: Artificial Sequence
<220> FEATURE:
<223> OTHER INFORMATION: SYNECHOCYSTIS

<400> SEQUENCE: 57
gactgcaggt cattgccgat aaagttg                                    27

<210> SEQ ID NO 58
<211> LENGTH: 31
<212> TYPE: DNA
<213> ORGANISM: Artificial Sequence
<220> FEATURE:

```
<223> OTHER INFORMATION: SYNECHOCYSTIS

<400> SEQUENCE: 58
agtctagata atgtacaggt caagctggtc t                              31

<210> SEQ ID NO 59
<211> LENGTH: 30
<212> TYPE: DNA
<213> ORGANISM: Artificial Sequence
<220> FEATURE:
<223> OTHER INFORMATION: SYNECHOCYSTIS

<400> SEQUENCE: 59
gagagctcat tgacaccgaa atgactttgg                                30

<210> SEQ ID NO 60
<211> LENGTH: 29
<212> TYPE: DNA
<213> ORGANISM: Artificial Sequence
<220> FEATURE:
<223> OTHER INFORMATION: SYNECHOCYSTIS

<400> SEQUENCE: 60
gagaattctt tgcatttccg aaaccaccc                                 29

<210> SEQ ID NO 61
<211> LENGTH: 30
<212> TYPE: DNA
<213> ORGANISM: Artificial Sequence
<220> FEATURE:
<223> OTHER INFORMATION: SYNECHOCYSTIS

<400> SEQUENCE: 61
gatctagaat tgacaccgaa atgactttgg                                30

<210> SEQ ID NO 62
<211> LENGTH: 29
<212> TYPE: DNA
<213> ORGANISM: Artificial Sequence
<220> FEATURE:
<223> OTHER INFORMATION: SYNECHOCYSTIS

<400> SEQUENCE: 62
gaggtacctt tgcatttccg aaaccaccc                                 29

<210> SEQ ID NO 63
<211> LENGTH: 26
<212> TYPE: DNA
<213> ORGANISM: Artificial Sequence
<220> FEATURE:
<223> OTHER INFORMATION: SYNECHOCYSTIS

<400> SEQUENCE: 63
taggctgtgg ttccctaggc aacagt                                    26

<210> SEQ ID NO 64
<211> LENGTH: 41
<212> TYPE: DNA
<213> ORGANISM: Artificial Sequence
<220> FEATURE:
<223> OTHER INFORMATION: SYNECHOCYSTIS

<400> SEQUENCE: 64
tccgtaaagt aatagccat tgaattaatc tcctacttga c                    41
```

```
<210> SEQ ID NO 65
<211> LENGTH: 40
<212> TYPE: DNA
<213> ORGANISM: Artificial Sequence
<220> FEATURE:
<223> OTHER INFORMATION: SYNECHOCYSTIS

<400> SEQUENCE: 65
aggagattaa ttcaatggct attaacttta cggaactgcg                           40

<210> SEQ ID NO 66
<211> LENGTH: 42
<212> TYPE: DNA
<213> ORGANISM: Artificial Sequence
<220> FEATURE:
<223> OTHER INFORMATION: SYNECHOCYSTIS

<400> SEQUENCE: 66
cattgaatta atctcctcta gggtttaatc cacattaggg tt                        42

<210> SEQ ID NO 67
<211> LENGTH: 45
<212> TYPE: DNA
<213> ORGANISM: Artificial Sequence
<220> FEATURE:
<223> OTHER INFORMATION: SYNECHOCYSTIS

<400> SEQUENCE: 67
cctagaggag attaattcaa tgcaattcgc caaaatttta attgc                     45

<210> SEQ ID NO 68
<211> LENGTH: 34
<212> TYPE: DNA
<213> ORGANISM: Artificial Sequence
<220> FEATURE:
<223> OTHER INFORMATION: SYNECHOCYSTIS

<400> SEQUENCE: 68
ctctccattg acctagggtg ttaaatgctc ttcg                                 34

<210> SEQ ID NO 69
<211> LENGTH: 41
<212> TYPE: DNA
<213> ORGANISM: Artificial Sequence
<220> FEATURE:
<223> OTHER INFORMATION: SYNECHOCYSTIS

<400> SEQUENCE: 69
gtggattaaa ccctagagga gattaattca atgcaattcg c                         41

<210> SEQ ID NO 70
<211> LENGTH: 39
<212> TYPE: DNA
<213> ORGANISM: Artificial Sequence
<220> FEATURE:
<223> OTHER INFORMATION: SYNECHOCYSTIS

<400> SEQUENCE: 70
ctttacttat ggcaatgctc tccattgacc tagggtgtt                            39

<210> SEQ ID NO 71
<211> LENGTH: 31
<212> TYPE: DNA
<213> ORGANISM: Artificial Sequence
<220> FEATURE:
<223> OTHER INFORMATION: SYNECHOCYSTIS
```

```
<400> SEQUENCE: 71
aacaccctag gtcaatggag agcattgcca t                              31

<210> SEQ ID NO 72
<211> LENGTH: 38
<212> TYPE: DNA
<213> ORGANISM: Artificial Sequence
<220> FEATURE:
<223> OTHER INFORMATION: SYNECHOCYSTIS

<400> SEQUENCE: 72
caatcaaata gagacatcta ggtcagtcct ccataaac                       38

<210> SEQ ID NO 73
<211> LENGTH: 37
<212> TYPE: DNA
<213> ORGANISM: Artificial Sequence
<220> FEATURE:
<223> OTHER INFORMATION: SYNECHOCYSTIS

<400> SEQUENCE: 73
aggactgacc tagatgtctc tatttgattg gtttgcc                        37

<210> SEQ ID NO 74
<211> LENGTH: 32
<212> TYPE: DNA
<213> ORGANISM: Artificial Sequence
<220> FEATURE:
<223> OTHER INFORMATION: SYNECHOCYSTIS

<400> SEQUENCE: 74
agtcctcctt aaccatcttg attgacggaa at                             32

<210> SEQ ID NO 75
<211> LENGTH: 36
<212> TYPE: DNA
<213> ORGANISM: Artificial Sequence
<220> FEATURE:
<223> OTHER INFORMATION: SYNECHOCYSTIS

<400> SEQUENCE: 75
gacctagatg agtaaaagtg agcgtcgtgt ttttct                         36

<210> SEQ ID NO 76
<211> LENGTH: 42
<212> TYPE: DNA
<213> ORGANISM: Artificial Sequence
<220> FEATURE:
<223> OTHER INFORMATION: SYNECHOCYSTIS

<400> SEQUENCE: 76
tcaagatggt taaggaggac tgacctagat gagtaaaagt ga                  42

<210> SEQ ID NO 77
<211> LENGTH: 36
<212> TYPE: DNA
<213> ORGANISM: Artificial Sequence
<220> FEATURE:
<223> OTHER INFORMATION: SYNECHOCYSTIS

<400> SEQUENCE: 77
tcattacacc gccgtttcta aaaattgacc caaatg                         36

<210> SEQ ID NO 78
<211> LENGTH: 26
```

```
<212> TYPE: DNA
<213> ORGANISM: Artificial Sequence
<220> FEATURE:
<223> OTHER INFORMATION: SYNECHOCYSTIS

<400> SEQUENCE: 78
ccttcggcca tcaagagaat gcagag                                          26

<210> SEQ ID NO 79
<211> LENGTH: 23
<212> TYPE: DNA
<213> ORGANISM: Artificial Sequence
<220> FEATURE:
<223> OTHER INFORMATION: SYNECHOCYSTIS

<400> SEQUENCE: 79
tgacgcaact gttcagcccg act                                             23

<210> SEQ ID NO 80
<211> LENGTH: 27
<212> TYPE: DNA
<213> ORGANISM: Artificial Sequence
<220> FEATURE:
<223> OTHER INFORMATION: SYNECHOCYSTIS

<400> SEQUENCE: 80
caccacttta cccatgacgg aaggtgg                                         27

<210> SEQ ID NO 81
<211> LENGTH: 31
<212> TYPE: DNA
<213> ORGANISM: Artificial Sequence
<220> FEATURE:
<223> OTHER INFORMATION: SYNECHOCYSTIS

<400> SEQUENCE: 81
tgtctcggag ttgcttaggg taatcatagc a                                    31

<210> SEQ ID NO 82
<211> LENGTH: 29
<212> TYPE: DNA
<213> ORGANISM: Artificial Sequence
<220> FEATURE:
<223> OTHER INFORMATION: SYNECHOCYSTIS

<400> SEQUENCE: 82
tcgcgaattc ctgttcatca acaacggtg                                       29

<210> SEQ ID NO 83
<211> LENGTH: 28
<212> TYPE: DNA
<213> ORGANISM: Artificial Sequence
<220> FEATURE:
<223> OTHER INFORMATION: SYNECHOCYSTIS

<400> SEQUENCE: 83
aaagctaaag cgactgagga agtgccag                                        28

<210> SEQ ID NO 84
<211> LENGTH: 24
<212> TYPE: DNA
<213> ORGANISM: Artificial Sequence
<220> FEATURE:
<223> OTHER INFORMATION: SYNECHOCYSTIS

<400> SEQUENCE: 84
```
agatatcgcg tgcaaggccc agtg                                         24

<210> SEQ ID NO 85
<211> LENGTH: 31
<212> TYPE: DNA
<213> ORGANISM: Artificial Sequence
<220> FEATURE:
<223> OTHER INFORMATION: SYNECHOCYSTIS

<400> SEQUENCE: 85
tgatatcatt aagagaccga gtttccattg g                                 31

<210> SEQ ID NO 86
<211> LENGTH: 28
<212> TYPE: DNA
<213> ORGANISM: Artificial Sequence
<220> FEATURE:
<223> OTHER INFORMATION: SYNECHOCYSTIS

<400> SEQUENCE: 86
gacttccaaa acggcgatca agccaacc                                     28

<210> SEQ ID NO 87
<211> LENGTH: 26
<212> TYPE: DNA
<213> ORGANISM: Artificial Sequence
<220> FEATURE:
<223> OTHER INFORMATION: SYNECHOCYSTIS

<400> SEQUENCE: 87
gtccattagg ggagtgtccg ccaaca                                       26

<210> SEQ ID NO 88
<211> LENGTH: 26
<212> TYPE: DNA
<213> ORGANISM: Artificial Sequence
<220> FEATURE:
<223> OTHER INFORMATION: SYNECHOCYSTIS

<400> SEQUENCE: 88
ggtaccatgc actggtggat tacgcc                                       26

<210> SEQ ID NO 89
<211> LENGTH: 35
<212> TYPE: DNA
<213> ORGANISM: Artificial Sequence
<220> FEATURE:
<223> OTHER INFORMATION: SYNECHOCYSTIS

<400> SEQUENCE: 89
gggaaattgt tccgttaact gttgatattc ccggt                             35

<210> SEQ ID NO 90
<211> LENGTH: 46
<212> TYPE: DNA
<213> ORGANISM: Artificial Sequence
<220> FEATURE:
<223> OTHER INFORMATION: SYNECHOCYSTIS

<400> SEQUENCE: 90
ctgaacgaag gaattataac caaatggtgg ctgctgctgc tagttc                 46

<210> SEQ ID NO 91
<211> LENGTH: 46
<212> TYPE: DNA
<213> ORGANISM: Artificial Sequence

```
<220> FEATURE:
<223> OTHER INFORMATION: SYNECHOCYSTIS

<400> SEQUENCE: 91
gaactagcag cagcagccac catttggtta taattccttc gttcag         46

<210> SEQ ID NO 92
<211> LENGTH: 37
<212> TYPE: DNA
<213> ORGANISM: Artificial Sequence
<220> FEATURE:
<223> OTHER INFORMATION: SYNECHOCYSTIS

<400> SEQUENCE: 92
caataggatt cgtagagatt gagatactcc atggcgt                   37

<210> SEQ ID NO 93
<211> LENGTH: 31
<212> TYPE: DNA
<213> ORGANISM: Artificial Sequence
<220> FEATURE:
<223> OTHER INFORMATION: SYNECHOCYSTIS

<400> SEQUENCE: 93
agcctttttt gagggctacc ttttggctgt t                         31

<210> SEQ ID NO 94
<211> LENGTH: 35
<212> TYPE: DNA
<213> ORGANISM: Artificial Sequence
<220> FEATURE:
<223> OTHER INFORMATION: SYNECHOCYSTIS

<400> SEQUENCE: 94
ggctccctac ttttacggtt acatttttgg cgaat                     35

<210> SEQ ID NO 95
<211> LENGTH: 37
<212> TYPE: DNA
<213> ORGANISM: Artificial Sequence
<220> FEATURE:
<223> OTHER INFORMATION: SYNECHOCYSTIS

<400> SEQUENCE: 95
ctacaaggaa gcaatttgtc gcatatattg accccaa                   37

<210> SEQ ID NO 96
<211> LENGTH: 34
<212> TYPE: DNA
<213> ORGANISM: Artificial Sequence
<220> FEATURE:
<223> OTHER INFORMATION: SYNECHOCYSTIS

<400> SEQUENCE: 96
gatatcgttc gttaattttt cccatcgctt ttag                      34

<210> SEQ ID NO 97
<211> LENGTH: 34
<212> TYPE: DNA
<213> ORGANISM: Artificial Sequence
<220> FEATURE:
<223> OTHER INFORMATION: SYNECHOCYSTIS

<400> SEQUENCE: 97
gatatctaaa cttagtctaa ggattaatga gagt                      34
```

<210> SEQ ID NO 98
<211> LENGTH: 32
<212> TYPE: DNA
<213> ORGANISM: Artificial Sequence
<220> FEATURE:
<223> OTHER INFORMATION: SYNECHOCYSTIS

<400> SEQUENCE: 98
atgatatctg taatttcgtc gagtcccagc ca                               32

<210> SEQ ID NO 99
<211> LENGTH: 34
<212> TYPE: DNA
<213> ORGANISM: Artificial Sequence
<220> FEATURE:
<223> OTHER INFORMATION: SYNECHOCYSTIS

<400> SEQUENCE: 99
ttgtttctcc tctttaaaat tatacgagcc ggat                             34

<210> SEQ ID NO 100
<211> LENGTH: 32
<212> TYPE: DNA
<213> ORGANISM: Artificial Sequence
<220> FEATURE:
<223> OTHER INFORMATION: SYNECHOCYSTIS

<400> SEQUENCE: 100
aaatgttcgg tttaatcggc catctgacta gc                               32

<210> SEQ ID NO 101
<211> LENGTH: 31
<212> TYPE: DNA
<213> ORGANISM: Artificial Sequence
<220> FEATURE:
<223> OTHER INFORMATION: SYNECHOCYSTIS

<400> SEQUENCE: 101
tcttaggcac cagtcagccc ataaacagac a                                31

<210> SEQ ID NO 102
<211> LENGTH: 34
<212> TYPE: DNA
<213> ORGANISM: Artificial Sequence
<220> FEATURE:
<223> OTHER INFORMATION: SYNECHOCYSTIS

<400> SEQUENCE: 102
atgtttggtt tgattgggca ctctactagt ttcg                             34

<210> SEQ ID NO 103
<211> LENGTH: 27
<212> TYPE: DNA
<213> ORGANISM: Artificial Sequence
<220> FEATURE:
<223> OTHER INFORMATION: SYNECHOCYSTIS

<400> SEQUENCE: 103
tcttaggcac cagtcagccc ataaaca                                     27

<210> SEQ ID NO 104
<211> LENGTH: 26
<212> TYPE: DNA
<213> ORGANISM: Artificial Sequence
<220> FEATURE:
<223> OTHER INFORMATION: SYNECHOCYSTIS

```
<400> SEQUENCE: 104
aaatgttcgg tctgatcggg cacctc                                          26

<210> SEQ ID NO 105
<211> LENGTH: 26
<212> TYPE: DNA
<213> ORGANISM: Artificial Sequence
<220> FEATURE:
<223> OTHER INFORMATION: SYNECHOCYSTIS

<400> SEQUENCE: 105
atatcttatt ggcggggagc actggc                                          26

<210> SEQ ID NO 106
<211> LENGTH: 36
<212> TYPE: DNA
<213> ORGANISM: Artificial Sequence
<220> FEATURE:
<223> OTHER INFORMATION: SYNECHOCYSTIS

<400> SEQUENCE: 106
ccaaatgaaa tttggtttaa ttggtcatct cactag                               36

<210> SEQ ID NO 107
<211> LENGTH: 40
<212> TYPE: DNA
<213> ORGANISM: Artificial Sequence
<220> FEATURE:
<223> OTHER INFORMATION: SYNECHOCYSTIS

<400> SEQUENCE: 107
aaggaattat aaccaaatgc cgcagcttga agccagcctt                           40

<210> SEQ ID NO 108
<211> LENGTH: 41
<212> TYPE: DNA
<213> ORGANISM: Artificial Sequence
<220> FEATURE:
<223> OTHER INFORMATION: SYNECHOCYSTIS

<400> SEQUENCE: 108
ttcaagctgc ggcatttggt tataattcct tcgttcagat t                         41

<210> SEQ ID NO 109
<211> LENGTH: 29
<212> TYPE: DNA
<213> ORGANISM: Artificial Sequence
<220> FEATURE:
<223> OTHER INFORMATION: SYNECHOCYSTIS

<400> SEQUENCE: 109
tcaaattgcc aatgccaagg gttggaagc                                       29

<210> SEQ ID NO 110
<211> LENGTH: 35
<212> TYPE: DNA
<213> ORGANISM: Artificial Sequence
<220> FEATURE:
<223> OTHER INFORMATION: SYNECHOCYSTIS

<400> SEQUENCE: 110
ctgatatctt aagcaccgat caacccgtag gcact                                35

<210> SEQ ID NO 111
```

```
<210> SEQ ID NO 111
<211> LENGTH: 34
<212> TYPE: DNA
<213> ORGANISM: Artificial Sequence
<220> FEATURE:
<223> OTHER INFORMATION: SYNECHOCYSTIS

<400> SEQUENCE: 111
ataagtttgg gttaccactg gtcgtttgag cttc                                34

<210> SEQ ID NO 112
<211> LENGTH: 30
<212> TYPE: DNA
<213> ORGANISM: Artificial Sequence
<220> FEATURE:
<223> OTHER INFORMATION: SYNECHOCYSTIS

<400> SEQUENCE: 112
cttcccttct tccttccatc tgattatggt                                    30

<210> SEQ ID NO 113
<211> LENGTH: 23
<212> TYPE: DNA
<213> ORGANISM: Artificial Sequence
<220> FEATURE:
<223> OTHER INFORMATION: SYNECHOCYSTIS

<400> SEQUENCE: 113
tggctccctg accaattttt cgg                                           23

<210> SEQ ID NO 114
<211> LENGTH: 24
<212> TYPE: DNA
<213> ORGANISM: Artificial Sequence
<220> FEATURE:
<223> OTHER INFORMATION: SYNECHOCYSTIS

<400> SEQUENCE: 114
ccaggcaatt tcctccggtt tacc                                          24

<210> SEQ ID NO 115
<211> LENGTH: 32
<212> TYPE: DNA
<213> ORGANISM: Artificial Sequence
<220> FEATURE:
<223> OTHER INFORMATION: SYNECHOCYSTIS

<400> SEQUENCE: 115
tcatcgtgtt aacagcggta tgcttctagt ct                                 32

<210> SEQ ID NO 116
<211> LENGTH: 35
<212> TYPE: DNA
<213> ORGANISM: Artificial Sequence
<220> FEATURE:
<223> OTHER INFORMATION: SYNECHOCYSTIS

<400> SEQUENCE: 116
caaaggtacc gctaatacct gtaagttcta cgagg                              35

<210> SEQ ID NO 117
<211> LENGTH: 24
<212> TYPE: DNA
<213> ORGANISM: Artificial Sequence
<220> FEATURE:
<223> OTHER INFORMATION: SYNECHOCYSTIS

<400> SEQUENCE: 117
```

```
gggggatcaat tgcgtctctg tggc                                           24

<210> SEQ ID NO 118
<211> LENGTH: 28
<212> TYPE: DNA
<213> ORGANISM: Artificial Sequence
<220> FEATURE:
<223> OTHER INFORMATION: SYNECHOCYSTIS

<400> SEQUENCE: 118
caaagcgttg accgtgccag tttttgac                                        28

<210> SEQ ID NO 119
<211> LENGTH: 36
<212> TYPE: DNA
<213> ORGANISM: Artificial Sequence
<220> FEATURE:
<223> OTHER INFORMATION: SYNECHOCYSTIS

<400> SEQUENCE: 119
ccctaaaaaa agtcaaacta acctttccca gggtgg                               36

<210> SEQ ID NO 120
<211> LENGTH: 34
<212> TYPE: DNA
<213> ORGANISM: Artificial Sequence
<220> FEATURE:
<223> OTHER INFORMATION: SYNECHOCYSTIS

<400> SEQUENCE: 120
cttctttggc cacatcttcg cctagtaaat ggtt                                 34

<210> SEQ ID NO 121
<211> LENGTH: 2447
<212> TYPE: DNA
<213> ORGANISM: Artificial Sequence
<220> FEATURE:
<223> OTHER INFORMATION: ACINETOBACTER BAYLYI

<400> SEQUENCE: 121
ttggcgggtg tcgggctggc ttaactatgc ggcatcaggc agattgtact gagagtgcac      60
catatgagaa ttccggatat ctagaagctt caacggctca caagcccaac taatcaccat     120
ttggacaaaa catcagtaat tctaattaga aagtccaaaa attgtaattt aaaaaacagt     180
caatggagag cattgccata agtaaaggca tcccctgcgt gataagatta ccttcagaaa     240
acagatagtt gctgggttat cgcagatttt tctcgcaacc aaataactgt aaataataac     300
tgtctctggg gcgacggtag gctttatatt gccaaatttc gcccgtggga gaaagctagg     360
ctattcaatg tttatggagg actgacctag atgcgtcctt tacacccgat tgatttcatc     420
tttctgtcct tggagaaacg tcaacaaccc atgcatgtag gcggcttatt cttgttccag     480
attcctgata acgcccccga caccttcatt caagatctgg tgaatgacat ccgcatctcc     540
aaatccattc ctgtgccccc ctttaacaat aaactgaacg gtctgttctg ggatgaggat     600
gaggagtttg acttagatca ccactttcgc cacattgccc tgccccaccc tggccgtatt     660
cgggaattat aatttatat cagccaagaa cacagtacgc tgctggaccg cgctaagccc     720
ttgtggacct gtaacattat cgaaggcatt gaaggcaatc gtttcgccat gtacttcaaa     780
attcaccatg cgatggtcga tggcgtcgcc ggtatgcgcc tgattgaaaa gtccctctcc     840
catgatgtaa ccgaaaaaag tatcgtgccc cctggtgcg tggaaggcaa acgggctaag     900
```

| | |
|---|---|
| cgcttacggg aacctaaaac tggtaaaatt aagaaaatca tgtctggtat taaaagtcag | 960 |
| ctgcaagcga cccccaccgt cattcaagaa ctctcccaaa ccgtattcaa agatattggc | 1020 |
| cgtaatcctg atcacgtgtc cagctttcag gcgccttgct ctattttgaa tcagcgtgtg | 1080 |
| agttcctccc ggcgttttgc cgcgcaaagt tttgacctgg atcgttttcg taatattgcc | 1140 |
| aaatccttga acgtcaccat taacgatgtg gtactggcgg tatgctctgg tgccttacgt | 1200 |
| gcgtatttga tgtcccacaa ttccctgcct tccaaaccct taattgctat ggtgcccgcc | 1260 |
| tctatccgga acgatgactc cgacgtcagc aaccgtatta cgatgattct cgcgaatttg | 1320 |
| gccacccaca aagatgatcc tttacaacgt ctcgaaatta tccgccgttc tgtgcaaaac | 1380 |
| tccaagcaac gcttcaaacg tatgactagc gaccaaattc tcaattatag tgctgtggta | 1440 |
| tatggtcctg ccggcctcaa cattatttct ggcatgatgc ccaaacgcca agccttcaat | 1500 |
| ctcgtgatca gcaatgttcc cggtccccgc gagcccctgt actggaatgg cgccaaactg | 1560 |
| gatgccctct accccgcctc cattgtatta cacggtcagg ccttgaatat taccatgact | 1620 |
| tcttacttag ataaattgga gctcggtttg attgcttgtc gtaatgcctt gccccggatg | 1680 |
| cagaatttac tgacccactt agaagaagaa attcaactct cgaaggtgt aattgcgaag | 1740 |
| caggaagata ttaaaactgc gaattaagga ggaattaaaa tgatcctgac ccccgagcaa | 1800 |
| gtggctgctg cgcaaaaagc taatctcgaa accctgttcg gtctgaccac taaagccttc | 1860 |
| gagggtgtgg aaaaactcgt ggaactcaat ctccaggtcg tgaaaacttc ctttgctgaa | 1920 |
| ggtgttgata atgccaaaaa agccctctcc gctaaagatg ctcaagaact gctcgctatc | 1980 |
| caagccgctg ctgttcagcc cgtggctgaa aaaaccctcg cttatacccg gcacctgtat | 2040 |
| gaaattgcct ccgaaaccca gagcgaattt accaaagtag ctgaagctca actggctgag | 2100 |
| ggttccaaaa atgtgcaagc gctggtcgaa aatctcgcta aaaatgctcc cgccggttcc | 2160 |
| gaatctaccg ttgctattgt taaatccgcc atctccgccg ccaataatgc ctacgaatcc | 2220 |
| gtgcagaaag cgaccaaaca agcggtcgaa attgccgaaa ccaatttcca ggctgccgct | 2280 |
| acggctgcta ccaaagctgc tcagcaagct agcgctacgg ctcgtacggc tacggctaaa | 2340 |
| aaaacgacgg ctgcttgaga attccggata tctagaagct tggtcgactg cagaggcctg | 2400 |
| catgaagctt ggcgtaatca tggtcatagc tgtttcctgt gtaaatt | 2447 |

<210> SEQ ID NO 122
<211> LENGTH: 2565
<212> TYPE: DNA
<213> ORGANISM: Artificial Sequence
<220> FEATURE:
<223> OTHER INFORMATION: SACCHAROMYCES CEREVISIAL

<400> SEQUENCE: 122

| | |
|---|---|
| agatatcgcg tgcaaggccc agtgatcaat ttcattattt ttcattattt catctccatt | 60 |
| gtccctgaaa atcagttgtg tcgcccctct acacagccca gaactatggt aaaggcgcac | 120 |
| gaaaaaccgc caggtaaact cttctcaacc cccaaaacgc cctctgttta cccatggaaa | 180 |
| aaacgacaat tacaagaaag taaaaacttat gtcatctata agcttcgtgt atattaactt | 240 |
| cctgttacaa agctttacaa aactctcatt aatcctttag actaagttta gtcagttcca | 300 |
| atctgaacta ggaattatac aaatggctgc ccctgactat gccttaaccg atttgattga | 360 |
| aagtgatccc cgtttcgaat ctttgaagac ccgtttggcc ggttatacta aagggtccga | 420 |
| cgaatacatt gaagaactgt actctcaatt gcccctgact tcctaccccc gttataaaac | 480 |
| tttcttgaaa aagcaggccg tcgccattag taatcctgat aatgaagccg gttttcctc | 540 |

```
tatttaccgc tcctctctct ccagcgaaaa cctggtatcc tgtgtcgata aaaacttgcg    600
cactgcctat gaccacttta tgtttagtgc ccggcgttgg ccccaacggg attgtctcgg    660
tagccggccc atcgataaag ccactggcac ctgggaagaa acctttcgtt ttgaatctta    720
tagtaccgtt tccaagcggt gccacaatat cggctccggg atcttgtccc tggtgaatac    780
taaacgcaag cgccccttag aagccaacga ctttgttgtc gctatcctgt cccacaataa    840
ccccgaatgg atcttgaccg atttggcttg tcaagcctac agtttaacca ataccgccct    900
gtatgaaacc ctgggtccca cacctctga atatatcctg aacttgaccg aggctccgat    960
cctgatttt gccaaatcca acatgtatca cgttctcaag atggtacccg atatgaaatt   1020
tgtcaacacc ttggtctgca tggacgaact gacccacgac gagttacgga tgttaaacga   1080
aagcttgctg cccgtaaagt gtaactccct gaatgagaaa attacctttt tcagcctcga   1140
acaagtggaa caagtaggtt gcttcaacaa aattcccgcc attcctccca ccccgattc   1200
cctgtatacc attagcttca ccagcggcac tactggtctg cccaagggcg tagagatgtc   1260
tcaccggaac attgcttccg gtattgcctt tgcttttagc acctttcgta tcccgccgga   1320
caagcgcaac caacaactgt atgacatgtg cttcctgccc ttggcccaca ttttcgaacg   1380
gatggtgatt gcttatgact tggctattgg ctttgggatc ggcttcctgc acaaaccgga   1440
ccctaccgtg ctggtagaag acttgaagat cctgaaaccg tacgctgtcg ccctggttcc   1500
ccggatcctg acccgtttcg aggctggcat taaaaacgcc ctggataaaa gcaccgttca   1560
gcggaacgtg gctaatacca tcctggatag caaatctgct cgctttactg cgcgtggcgg   1620
tcccgacaag tctattatga acttttggt ctaccatcgg gtgctgattg ataaaatccg   1680
cgacagcctc ggtttatcta acaacagttt cattatcacc ggtagcgctc ctatcagcaa   1740
agatactctc ctcttcttgc ggtccgccct ggacattggt atccggcagg ttacggcct   1800
cactgaaact ttcgccggtg tttgtctgtc cgaacctttc gaaaagacg tgggttcctg   1860
tggtgccatt ggtatctccg ccgaatgccg cctcaaatcc gtacccgaga tgggctacca   1920
cgctgacaaa gacctgaaag gggaattaca aatccgtggc ccgcaagtgt ttgaacgtta   1980
ctttaagaac cccaacgaaa ccagcaaagc cgtggatcaa gatggttggt ttagtaccgg   2040
cgacgtggcg ttcattgatg gtaaaggtcg tatctccgtg attgaccgcg tgaaaaactt   2100
cttcaaactg gccacggtg aatacattgc ccccgaaaaa atcgaaaaca tttacttgag   2160
ttcttgtccc tacattaccc aaatttttgt ctttggtgac cccctcaaaa ccttttggt   2220
aggcattgtt ggggtcgacg tggacgccgc tcaacccatt ttggctgcca acatccgga   2280
agtgaaaact tggaccaaag aagtcctcgt ggaaaacctg aatcggaata aaaagctgcg   2340
caaagagttt ctgaataaga ttaacaaatg taccgacggg ttgcagggtt tcgaaaaatt   2400
gcacaacatc aaagtgggcc tcgagcctct gaccttagaa gatgatgtag ttaccccctac  2460
cttcaaaatt aagcgtgcca aagcctccaa attttcaag gataccttgg accaactgta   2520
cgctgaaggt agcttagtga aaaccgaaaa actgtaagat atcat                  2565
```

<210> SEQ ID NO 123
<211> LENGTH: 1360
<212> TYPE: DNA
<213> ORGANISM: Artificial Sequence
<220> FEATURE:
<223> OTHER INFORMATION: CAVIA PORCELLUS

<400> SEQUENCE: 123

```
atgaaattgt tgcctggac tattggttta ctgctgctgg ccactgtgcg cggcgctgag     60
gtctgttatt ctcatttggg ctgcttttcc gacgagaaac cgtgggcggg tacctctcaa   120
cggcccatca agagtttgcc gtccgaccct aaaaagatta atacccggtt cttgctgtac   180
accaatgaaa tcaaaattc ctaccaactg atcaccgcta ctgatattgc caccatcaaa    240
gccagtaact tcaatctcaa ccgcaaaacc cgcttcatta ttcacggttt caccgacagc   300
ggtgagaact cttggctgag tgatatgtgt aaaaacatgt ccaagttga aaaagtgaat    360
tgcatttgcg tggattggaa aggcggttcc aaggctcaat acagtcaggc ttcccagaat   420
attcgggtgg tcggtgccga agttgcctat ttagtgcaag tactgagcac ctccctgaac   480
tatgccccgg aaaacgtaca tattattggt cactccctcg gcgcccacac cgctggggaa   540
gccgggaagc ggctgaacgg gctggtaggg cggattaccg gcctcgaccc cgccgaaccc   600
tactttcaag atacccccga agaagtccgg ctggatccct ctgacgctaa atttgtggac   660
gtgattcaca ctgatattag ccccattctg cctagtctgg gtttcggtat gtcccagaag   720
gtcggtcaca tggacttctt ccccaacggc ggcaaagata tgcccgggtg caaaaccggc   780
atctcctgca accaccaccg gagtattgaa tattatcaca gcagtatttt gaaccccgaa   840
ggttttttag gctaccgtg tgcttcctac gatgaattcc aagaatctgg gtgcttcccc    900
tgtcccgcta aggttgtcc taaaatgggt cactttgccg accagtaccc cgggaagacc    960
aatgctgtcg aacaaacctt cttcctcaac accggggcgt ccgataattt cacccggtgg  1020
cgctataaag taaccgttac cctgagtggc gaaaagacc cgtccggtaa catcaatgtg   1080
gctttgttag gtaaaaacgg gaactctgct caataccagg ttttcaaggg caccctgaag  1140
cccgacgcct cctatactaa ttccattgat gtcgaactca cgttgggac cattcaaaaa   1200
gtgaccttcc tgtggaaacg gagcgggatc tccgtctcta aacccaagat gggtgcttct  1260
cgcattactg ttcaaagtgg taaagacggg accaaatata acttctgctc cagcgatatt  1320
gtgcaagaaa acgtcgagca gactctgagc ccctgctaaa                        1360
```

<210> SEQ ID NO 124
<211> LENGTH: 2077
<212> TYPE: DNA
<213> ORGANISM: Artificial Sequence
<220> FEATURE:
<223> OTHER INFORMATION: STAPHYLOCOCCUS HYICUS

<400> SEQUENCE: 124

```
ttcccaattt gaggaggtgt gatggaagta tcccaagatc tgtttaatca attcaatctg    60
ttcgctcaat actccgcggc tgcttactgt gggaaaaata cgatgctcc tgcgggcacc   120
aatattactt gtaccggtaa cgcttgccct gaagtggaga aggctgacgc caccttttg    180
tacagcttcg aagatagcgg cgtaggcgat gtgactggtt tcctcgcctt ggataatacc   240
aataaattga ttgttctctc tttccgtggc agtgactcca ttgagaattg gattgccaac   300
ttgaacttt ggttgaagaa aatcaatgat atttgttccg ctgtcggggt cacgatggt    360
ttcaccagca gctggcgttc cgtggccgac accctccggc aaaaggtgga agatgctgtg   420
cgcgaacatc ctgattaccg cgttgttttt accgggcact ccctgggcgg ggccttggcc   480
accgtagccg tgctgaccct gcgcggtaac ggctacgata ttgatgtgtt ctcctatggg   540
gctccccggg ttgggaaccg ggcttttgct gagtttttga ccgttcaaac cggcggtacc   600
tgtatcgga tcaccatac caatgatatt gttccccgcc tgcccctcg tgaattcggt     660
tatagccact cctcccccga atactggatt aaaagcggca ccttggttcc cgtgacccgt   720
```

```
aacgacattg taaaaattga gggcattgac gccaccggtg gtaataatca acctaatatc    780
cccgatatct tggctcatct gtggtatttt caagccaccg acgcttgtaa cgccggcggt    840
ttcagttaat gaggagatta attcaatgaa gcctaccgtt aaagctgctc ccgaggctgt    900
tcagaacccg gaaaacccga aaacaagga ccccctttgtg tttgtgcacg gctttaccgg    960
ttttgtgggg gaggttgctg cgaaaggtga gaatcactgg ggcggcacca aagccaatct   1020
gcgcaaccat ttgcggaaag ctggttacga aacctacgaa gcctccgtat ccgccttggc   1080
ctccaatcac gaacgtgctg tggaactgta ctattatctg aaaggtggtc gggtagacta   1140
tggtgctgcc cattccgaaa aatatggcca tgagcgttac gggaaaactt atgaaggtgt   1200
gctgaaagat tggaaacccg gcaccccgt acactttatc ggtcattcca tgggtggtca   1260
gaccattcgg ctgctggaac attatctgcg ctttggtgat aaagccgaaa ttgcctatca   1320
acaacagcac gggggtatta ttagcgaatt atttaagggc ggtcaagaca acatggtgac   1380
ctctatcact actattgcca cccctcacaa tggtacccat gcttctgacg atattggcaa   1440
taccccgact atccggaaca ttctgtatag cttcgcccaa atgtccagtc atctgggcac   1500
catcgacttt gggatggacc attggggttt caagcggaaa gatggcgaga gtctgaccga   1560
ttataataag cggattgccg agagcaaaat ctgggattct gaagatactg gctgtatga    1620 cctgacccgt gaaggcgccg agaaaatcaa ccagaaaacc gaattgaatc ccaatatcta   1680
ttacaaaacc tacactgggg tggctaccca tgaaactcag ttaggcaaac acatcgcgga   1740
cctcggcatg gaatttacca aaatcctcac cggcaactat atcgggagcg tagacgatat   1800
tctgtggcgg cccaatgatg gtttggtgag cgaaatctcc agccaacacc ccagcgatga   1860
gaagaacatt tccgtagacg aaaactccga actgcataag ggtacctggc aggtcatgcc   1920
taccatgaaa gggtgggacc actccgattt tattggtaat gacgccctgg ataccaaaca   1980
ctccgccatc gaactcacca acttttatca tagcatttct gactacttga tgcggatcga   2040
aaaagccgaa tctaccaaaa acgcctaatg atatcga                             2077
```

<210> SEQ ID NO 125
<211> LENGTH: 637
<212> TYPE: DNA
<213> ORGANISM: Artificial Sequence
<220> FEATURE:
<223> OTHER INFORMATION: ESCHERICHIA COLI

<400> SEQUENCE: 125

```
gagctgttga caattaatca tccggctcgt ataattttaa agaggagaaa atgaaagctg     60
atactctgtt gattttgggg gactccttgt ctgctggtta tcgtatgtcc gctagcgccg    120
cttggcccgc cttgctcaac gacaaatggc aaagtaagac ttccgttgtg aatgcttcca    180
ttagtggtga caccagccag cagggcctgg ctcgtctccc cgctctgctc aaacagcatc    240
agccccgttg ggtcctggta gaactgggcg gtaacgacgg tctccgcggc ttccaacctc    300
aacagaccga acaaaccctc cggcagatct acaggatgt gaaagccgcc aacgccgaac    360
ccctcctgat gcaaatccgc ctgcccgcca actatggtcg gcgctataac gaagccttca    420
gtgctatcta tcccaaactc gctaaggaat tcgacgtgcc cctgctgccc tttttcatgg    480
aagaagttta tctgaaaccc cagtggatgc aagacgatgg tattcatccc aatcgtgacg    540 ctcaacccett tattgccgat tggatggcta acaattaca acccctcgta aaccacgatt    600
ccgactataa agatgacgat gacaagtaag atatcga                             637
```

<210> SEQ ID NO 126
<211> LENGTH: 2936
<212> TYPE: DNA
<213> ORGANISM: Artificial Sequence
<220> FEATURE:
<223> OTHER INFORMATION: SYNTHESIZED

<400> SEQUENCE: 126

| | | | | | |
|---|---|---|---|---|---|
| agatatcgcg | tgcaaggccc | agtgatcaat | ttcattattt | ttcattattt | catctccatt | 60 |
| gtccctgaaa | atcagttgtg | tcgcccctct | acacagccca | gaactatggt | aaaggcgcac | 120 |
| gaaaaaccgc | caggtaaact | cttctcaacc | cccaaaacgc | cctctgttta | cccatggaaa | 180 |
| aaacgacaat | tacaagaaag | taaaacttat | gtcatctata | agcttcgtgt | atattaactt | 240 |
| cctgttacaa | agctttacaa | aactctcatt | aatcctttag | actaagttta | gtcagttcca | 300 |
| atctgaacta | aggaattata | accaaatggc | taccacctct | ttagcttccg | ccttttgctc | 360 |
| gatgaaagct | gtaatgttag | ctcgtgatgg | tcggggtatg | aaacctcgta | gtagtgattt | 420 |
| gcaactccgt | gcgggaaatg | cgcctacctc | tttgaaaatg | atcaatggga | ccaaattcag | 480 |
| ttatacggag | agcttgaaac | ggttgcctga | ttggagcatg | ctctttgctg | ttatcaccac | 540 |
| catcttttcg | gctgctgaga | aacaatggac | taatctagag | tggaagccga | aaccgaagct | 600 |
| accccagttg | cttgatgatc | attttggact | gcatgggtta | gttttccggc | gcacctttgc | 660 |
| catccggtct | tatgaagttg | gacctgatcg | ctccacctct | attctggctg | ttatgaatca | 720 |
| tatgcaggag | gctaccctta | atcatgcgaa | aagtgtggga | attctaggag | atggattcgg | 780 |
| gacgacgcta | gagatgagta | agcgggatct | gatgtgggtt | gttcggcgca | cgcatgttgc | 840 |
| tgttgaacgg | taccctactt | ggggtgatac | tgtagaagta | gagtgctgga | ttggtgcttc | 900 |
| tggaaataat | ggcatgcgtc | gtgatttcct | tgtccgggac | tgcaaaaccg | gcgaaattct | 960 |
| tactcgctgt | accagccttt | cggtgctgat | gaatactcgc | actcgtcgtt | tgtccaccat | 1020 |
| tcctgatgaa | gttcgtggtg | aaatagggcc | tgctttcatc | gataatgttg | ctgtgaaaga | 1080 |
| cgatgaaatt | aagaaactac | aaaaactcaa | tgatagcact | gccgattata | ttcaaggagg | 1140 |
| tttgacccct | cgttggaatg | atttggatgt | caatcaacat | gttaacaacc | tcaaatacgt | 1200 |
| tgcctgggtt | tttgagaccg | tccccgattc | catctttgag | agtcatcata | tttccagctt | 1260 |
| cactcttgaa | tatcgtcgtg | agtgtacccg | tgatagcgtg | ctgcggtccc | tgaccactgt | 1320 |
| ctctggtggc | tcgtcggagg | ctgggttagt | ttgcgatcat | ttgctccaac | ttgaaggtgg | 1380 |
| gtctgaggta | ttgcgtgcca | gaactgagtg | gcggcctaaa | cttaccgata | gtttccgcgg | 1440 |
| cattagtgtt | attcccgccg | aaccgcgcgt | gtaaggagag | cattgccata | agtaaaggca | 1500 |
| tcccctgcgt | gataagatta | ccttcagaaa | acagatagtt | gctgggttat | cgcagatttt | 1560 |
| tctcgcaacc | aaataactgt | aaataataac | tgtctctggg | gcgacggtag | gctttatatt | 1620 |
| gccaaatttc | gcccgtggga | gaaagctagg | ctattcaatg | tttatggagg | actgacctag | 1680 |
| atggtggctg | ctgctgctag | ttccgctttc | ttccctgttc | cagcccccgg | agcctcccct | 1740 |
| aaacccggga | agttcggaaa | ttggcccagt | agcttgagcc | cttccttcaa | gcccaagtca | 1800 |
| atccccaatg | gcggatttca | ggttaaggct | aatgacagcg | cccatccaaa | agccaatggt | 1860 |
| tctgccgtta | gtctaaagtc | tggcagcctc | aacactcaag | aagacactag | ttcctcccct | 1920 |
| cctcctcgga | ctttccttca | tcagttgcct | gattggagtc | gtcttctgac | tgctattacc | 1980 |
| accgtgttcg | tgaatctaa | gcgtcctgac | atgcatgatc | ggaaatccaa | gcgtcctgac | 2040 |
| atgctggtgg | actcctttgg | gttggagagt | actgttcagg | atggcttagt | gttccgacag | 2100 |

```
agtttttcca ttcgttctta tgaaataggc actgatcgaa cggcctctat agagacccct     2160
atgaaccact tgcaggaaac ctctctcaat cattgtaaga gtaccggtat tctccttgac     2220
ggcttcggtc gtactcttga gatgtgtaaa cgcgacctca tttgggtggt aattaaaatg     2280
cagatcaagg tgaatcgcta ccagcttggg gcgatactg tcgagatcaa tacccgtttc     2340
agccggttgg ggaaaattgg tatgggtcgc gattggctaa ttagtgattg caacaccgga     2400
gaaattcttg tacgggctac gagcgcgtat gccatgatga atcaaaagac gcggagactc     2460
tccaaacttc catacgaggt tcaccaggag attgtgcctc tttttgtcga ctctcctgtc     2520
attgaagaca gtgatctgaa agtgcataag tttaaagtga agactggtga cagcattcaa     2580
aagggtctaa ctccggggtg gaatgacttg gatgtcaatc agcacgtaag caacgtgaag     2640
tacattgggt ggattctcga gagtatgcca acagaagttt tggagaccca ggagctatgc     2700
tctctcgccc ttgaatatcg ccgggaatgc ggacgcgaca gtgtgctgga gtccgtgacc     2760
gctatggatc cctccaaagt tggagtccgt tctcagtacc agcaccttct gcggcttgag     2820
gatgggactg ctatcgtgaa cggtgctact gagtggcggc cgaagaatgc aggagctaac     2880
ggggcgatca gcacgggaaa gacttccaat ggaaactcgg tctcttaatg atatca         2936

<210> SEQ ID NO 127
<211> LENGTH: 1581
<212> TYPE: DNA
<213> ORGANISM: Artificial Sequence
<220> FEATURE:
<223> OTHER INFORMATION: SYNTHESIZED

<400> SEQUENCE: 127
agatatcgcg tgcaaggccc agtgatcaat ttcattattt ttcattattt catctccatt       60
gtccctgaaa atcagttgtg tcgcccctct acacagccca gaactatggt aaaggcgcac      120
gaaaaaccgc caggtaaact cttctcaacc cccaaaacgc cctctgttta cccatggaaa      180
aaacgacaat tacaagaaag taaaacttat gtcatctata agcttcgtgt atattaactt      240
cctgttacaa agcttacaa aactctcatt aatcctttag actaagttta gtcagttcca      300
atctgaacta aggaattata accaaatggt ggctgctgct gctagttccg ctttcttccc      360
tgttccagcc cccggagcct cccctaaacc cgggaagttc ggaaattggc ccagtagctt      420
gagcccttcc ttcaagccca agtcaatccc caatggcgga tttcaggtta aggctaatga      480
cagcgcccat ccaaaagcca atggttctgc cgttagtcta agtctggca gcctcaacac        540 tcaagaagac actagttcct cccctcctcc tcggactttc cttcatcagt tgcctgattg      600
gagtcgtctt ctgactgcta ttaccaccgt gttcgtgaaa tctaagcgtc ctgacatgca      660
tgatcggaaa tccaagcgtc ctgacatgct ggtggactcc tttgggttgg agagtactgt      720
tcaggatggc ttagtgttcc gacagagttt ttccattcgt tcttatgaaa taggcactga      780
tcgaacggcc tctatagaga cccttatgaa ccacttgcag gaaacctctc tcaatcattg      840
taagagtacc ggtattctcc ttgacggctt cggtcgtact cttgagatgt gtaaacgcga      900 cctcattttgg gtggtaatta aaatgcagat caaggtgaat cgctatccag cttggggcga      960
tactgtcgag atcaatacccc gtttcagccg gttggggaaa attggtatgg gtcgcgattg     1020
gctaattagt gattgcaaca ccggagaaat tcttgtacgg gctacgagcg cgtatgccat     1080
gatgaatcaa aagacgcgga gactctccaa acttccatac gaggttcacc aggagattgt     1140
gcctcttttt gtcgactctc ctgtcattga agacagtgat ctgaaagtgc ataagtttaa     1200
```

```
agtgaagact ggtgacagca ttcaaaaggg tctaactccg gggtggaatg acttggatgt    1260
caatcagcac gtaagcaacg tgaagtacat tgggtggatt ctcgagagta tgccaacaga    1320
agttttggag acccaggagc tatgctctct cgcccttgaa tatcgccggg aatgcggacg    1380
cgacagtgtg ctggagtccg tgaccgctat ggatccctcc aaagttggag tccgttctca    1440
gtaccagcac cttctgcggc ttgaggatgg gactgctatc gtgaacggtg ctactgagtg    1500
gcggccgaag aatgcaggag ctaacggggc gatcagcacg ggaaagactt ccaatggaaa    1560
ctcggtctct taatgatatc a    1581

<210> SEQ ID NO 128
<211> LENGTH: 1482
<212> TYPE: DNA
<213> ORGANISM: Artificial Sequence
<220> FEATURE:
<223> OTHER INFORMATION: SYNTHESIZED

<400> SEQUENCE: 128
agatatcgcg tgcaaggccc agtgatcaat ttcattattt ttcattattt catctccatt      60
gtccctgaaa atcagttgtg tcgcccctct acacagccca gaactatggt aaaggcgcac    120
gaaaaaccgc caggtaaaact cttctcaacc cccaaaacgc cctctgttta cccatggaaa    180
aaacgacaat tacaagaaag taaaacttat gtcatctata agcttcgtgt atattaactt    240
cctgttacaa agctttacaa aactctcatt aatcctttag actaagttta gtcagttcca    300
atctgaacta aggaattata accaaatgaa aactacttct ctcgcctctg ccttctgttc    360
tatgaaagct gttatgctgg cgcgggatgg tcgcggtatg aaaccccgtt ccagtgatct    420
gcaattacgg gctggcaacg ctcagacctc cttgaagatg attaacggca ctaaattcag    480
ttataccgaa tctttgaaga aactccccga ttggagcatg ttgttcgccg tgattaccac    540
catttttagt gctgccgaaa acaatggac caatctcgaa tggaaaccca aacccaaccc    600
cccgcagctg ctcgatgacc attttggccc ccacggcttg gtgtttcggc gtaccttcgc    660
tatccggtct tatgaagtcg gtcccgatcg gagcacttcc atcgtcgctg ttatgaatca    720
cttgcaagaa gccgctttga accatgctaa atctgttggg attctgggtg atggcttcgg    780
taccactctg gagatgagta agcgcgatct gatctgggta gtaaagcgta tcatgtggc    840 cgtgaacgt tatccggcct gggtgtac cgtagaagtg gagtgttggg taggcgcctc    900
cggtaacaac ggtcggcgtc acgacttctt ggtgcgtgac tgtaaaactg gcgagatcct    960
gacccgctgt acttccctga gcgttatgat gaacacccgg accgtcgct tatccaagat    1020 tcccgaagaa gttcgcgggg aaattggtcc tgctttcatt gataacgttg ctgttaagga    1080
tgaggagatt aaaaagccgc aaaagctcaa tgattctacc gccgattaca ttcaagggg    1140 tctgactccc cgttggaatg atctggatat taatcagcat gtgaataaca tcaaatatgt    1200
ggattggatt ctgagactg tgcccgactc tatttttcgag tcccaccaca ttagcagttt    1260
taccattgaa tatcgtcgcg aatgtactat ggacagtgtt ttgcaatccc tgaccaccgt    1320
ctccggcggt tcctctgaag ctggcctggt gtgcgaacac ctcttgcaac tcgaaggcgg    1380
tagtgaagtg ctccgtgcca agaccgaatg gcggcccaaa ttgaccgact cctttcgcgg    1440
gatttctgtg attcccgccg aatcctccgt ctaagatatc at    1482

<210> SEQ ID NO 129
<211> LENGTH: 1482
<212> TYPE: DNA
<213> ORGANISM: Artificial Sequence
```

<220> FEATURE:
<223> OTHER INFORMATION: SYNTHESIZED

<400> SEQUENCE: 129

```
agatatcgcg tgcaaggccc agtgatcaat ttcattattt ttcattattt catctccatt      60
gtccctgaaa atcagttgtg tcgcccctct acacagccca gaactatggt aaaggcgcac     120
gaaaaaccgc caggtaaact cttctcaacc cccaaaacgc cctctgttta cccatggaaa     180
aaacgacaat tacaagaaag taaaacttat gtcatctata agcttcgtgt atattaactt     240
cctgttacaa agctttacaa aactctcatt aatcctttag actaagttta gtcagttcca     300
atctgaacta aggaattata accaaatgaa aactacttct ctcgcctctg ccttctgttc     360
tatgaaagct gttatgctgg cgcgggatgg tcgcggtatg aaaccccgtt ccagtgatct     420
gcaattacgg gctggcaacg ctcagacctc cttgaagatg attaacgcca ctaaattcag     480
ttataccgaa tctttgaaga aactccccga ttggagcatg ttgttcgccg tgattaccac     540
cattttagt gctgccgaaa acaatggac caatctcgaa tggaaaccca aacccaaccc     600
cccgcagctg ctcgatgacc attttggccc ccacggcttg gtgtttcggc gtaccttcgc     660
tatccggtct tatgaagtcg gtcccgatcg gagcacttcc atcgtcgctg ttatgaatca     720
cttgcaagaa gccgctttga accatgctaa atctgttggg attctgggtg atggcttcgg     780
taccactctg gagatgagta agcgcgatct gatctgggta gtaaagcgta tcatgtggc     840
cgtggaacgt tatccggcct ggggtgatac cgtagaagtg gagtgttggg taggcgcctc     900
cggtaacaac ggtcggcgtc acgacttctt ggtgcgtgac tgtaaaactg gcgagatcct     960
gacccgctgt acttccctga gcgttatgat gaacacccgg accgtcgct tatccaagat    1020
tcccgaagaa gttcgcgggg aaattggtcc tgctttcatt gataacgttg ctgttaagga    1080
tgaggagatt aaaaagccgc aaaagctcaa tgattctacc gccgattaca ttcaaggggg    1140
tctgactccc cgttggaatg atctggatat taatcagcat gtgaataaca tcaaatatgt    1200
ggattggatt ctggagactg tgcccgactc tattttcgag tccccaccaca ttagcagttt    1260
taccattgaa tatcgtcgcg aatgtactat ggacagtgtt ttgcaatccc tgaccaccgt    1320
ctccggcggt tcctctgaag ctggcctggt gtgcgaacac ctcttgcaac tcgaaggcgg    1380
tagtgaagtg ctccgtgcca agaccgaatg gcggcccaaa ttgaccgact cctttcgcgg    1440
gatttctgtg attcccgccg aatcctccgt ctaagatatc at                       1482
```

<210> SEQ ID NO 130
<211> LENGTH: 391
<212> TYPE: DNA
<213> ORGANISM: Artificial Sequence
<220> FEATURE:
<223> OTHER INFORMATION: SYNTHESIZED

<400> SEQUENCE: 130

```
gatatcgttc gttaattttt cccatcgctt ttagtagatg taggcagatc caaccatcgg      60
taaagttgat tagtgtggcc caggcccatc gccggcaggg attgggaaag tatcacgaat     120
tacactgccg tgaaaattta acgatatttt ggacagggga agattggcg atcgccgttg     180
tggttaagcc agctaaaagg cccactcgtt aggacacacg gtgtaaaaaa aaacaaaata     240
ttttgccca tttttgcggt caactttgac tgaccagcta attttgtaca cgacttagga     300
gtttgtaatt tcgtcgagtc ccagccaccc ccgacccaag tttgcttgct ttacaaaact     360
ctcattaatc cttagactaa gtttagatat c                                   391
```

<210> SEQ ID NO 131
<211> LENGTH: 439
<212> TYPE: DNA
<213> ORGANISM: Artificial Sequence
<220> FEATURE:
<223> OTHER INFORMATION: SYNTHESIZED

<400> SEQUENCE: 131

```
atgatatctg taatttcgtc gagtcccagc cacccccgac ccaagtttgc ttgctttaca    60
aaactctcat taatccttag actaagttta acaaaatatt tttgcccatt tttgcggtca   120
actttgactg accagctaat tttgtacacg acttaggagt tgggaaagat tggcgatcgc   180
cgttgtggtt aagccagcta aaggcccac tcgttaggac acacggtgta aaaaaaagtt   240
cgttaatttt tcccatcgct tttagtagat gtaggcagat ccaaccatcg gtaaagttga   300
ttagtgtggc ccaggcccat cgccggcagg gattgggaaa gtatcacgaa ttacactgcc   360
gtgaaaattt aacgatattt tggacagagc tgttgacaat taatcatccg gctcgtataa   420
ttttaaagag gagaaacaa                                                439
```

<210> SEQ ID NO 132
<211> LENGTH: 1880
<212> TYPE: DNA
<213> ORGANISM: Artificial Sequence
<220> FEATURE:
<223> OTHER INFORMATION: SYNTHESIZED

<400> SEQUENCE: 132

```
gagatatcga gctgttgaca attaatcatc cggctcgtat aattttaaag aggagaaaca    60
aatgttcggt ctgatcgggc acctcaccaa tttgtcccac gcccaacggg ttgcccgcga   120
cttgggctac gacgaatacg cctcccacga tttagaattt tggtgcatgg ccccccccca   180
agccgttgac gaaatcacta ttacttccgt gaccggtcag gtgatccacg gccagtatgt   240
agagtcctgt tttttacccg aaatgctcgc gcaagggcgg ttcaagactg ctatgcgcaa   300
aatcctgaac gccatggccc tggtacaaaa acggggtatt gacattaccg ctttaggggg   360
gttcagtagc atcattttcg agaatttttc cctcgataaa ttgctcaatg tgcgtgatat   420
taccctcgac atccagcgct tcaccaccgg caacactcac accgcgtata ttttgtgtca   480
acaagtggaa caaggtgcgg tacgtacgg tattgatccc gccaaagcca ccgttgccgt   540
ggtcggggcc accggtgata ttggttccgc cgtatgccgc tggttgactg atcgggctgg   600
gatccacgaa ttgttgttgg tggcccgtga cgctgaacgt ctcgaccggc tccaacaaga   660
actcggtacc ggtcggattc tccccgtgga ggaggccctg cccaaagcgg atattgtggt   720
atgggtggct tccatgaacc aggggatggc tatcgacccc gcggggctgc gtacccctg   780
tttgctcatc gatggtggct accccaaaaa catggcgggc accttgcaac ggcccggcat   840
tcacattctg gacgggggca tggttgaaca ctccttggac atcgactggc agattatgag   900
cttcctgaat gtgccgaacc ccgcccggca attcttcgct tgttttgctg aaagcatgct   960
gctggaattc gaaggtttgc acttcaactt ttcctggggt cgtaaccata ttactgtaga  1020
aaagatggcg caaattggct ccctgagcaa gaaacacggc tttcgccctt tgttggaacc  1080
ctcccaacgc tccggtgaac tggtgcacgg ttaaagctgt tgacaactga tcatacgtct  1140
cgtataattt taaagaggag aaacaaatga atcggaccgc tccctcctct gccgctttgg  1200
actaccggtc tgatacctat cgggatgcct atagccgcat taacgctatt gtcctcgaag  1260
gtgaacggga agcgcacgcg aattatttga ccttggccga aatgctgccc gaccatgccg  1320
```

```
aagctctgaa aaagttggcc gctatggaaa atcgccactt caaaggcttc cagtcctgcg    1380
cccgtaatct cgaagtgacc cccgatgatc ccttcgcgcg tgcgtacttc gagcaattgg    1440
atggcaactt ccaacaggcc gctgccgaag gtgacttgac cacttgtatg gtcattcaag    1500
cgctcattat tgaatgtttt gccattgccg cctataacgt gtacattcct gtcgccgacg    1560
ccttcgcccg caaagtgacc gagggtgttg tcaaagacga gtacactcat ttaaactttg    1620
gccaacaatg gctgaaggaa cgtttcgtaa ctgtgcgtga aggtatcgag cgtgccaatg    1680
ctcaaaactt gcccattgtt tggcgcatgc tcaatgctgt tgaagccgat accgaagttt    1740
tgcagatgga taaggaagcc attgtcgaag acttcatgat tgcttacggt gaagccctcg    1800
gtgatattgg gtttagcatg cgtgatgtga tgaaaatgtc cgctcgtggt ttggccagtg    1860
ctccccgcca ataagatatc                                                1880
```

<210> SEQ ID NO 133
<211> LENGTH: 2117
<212> TYPE: DNA
<213> ORGANISM: Artificial Sequence
<220> FEATURE:
<223> OTHER INFORMATION: SYNTHESIZED

<400> SEQUENCE: 133

```
agatatcgcg tgcaaggccc agtgatcaat ttcattattt ttcattattt catctccatt      60
gtccctgaaa atcagttgtg tcgcccctct acacagccca gaactatggt aaaggcgcac     120
gaaaaaccgc caggtaaact cttctcaacc cccaaaacgc cctctgttta cccatggaaa     180
aaacgacaat tacaagaaag taaaacttat gtcatctata agcttcgtgt atattaactt     240
cctgttacaa agctttacaa aactctcatt aatcctttag actaagttta gtcagttcca     300
atctgaacga aggaattata accaaatgaa atttggttta attggtcatc tcactagttt     360
agagcaggcc cggatgtttt cccgtcggat gggttatgat gagtacgccg atcagggttt     420
ggaattttgg tcttccgctc ctccccaaat cgttgatgaa atcaccgtta cttccgccac     480
cggtaaggtg atccacgtc gttacattga aagttgtttc ctgcccgaaa tgttggccgc     540
tcgccggttt aaaaccgcca cccgtaaagt gttgaacgct atgagccacg ctcagaaaca     600
cggcattgat atctccgccc tcggtggttt taccagtatc attttgaaa actttgatct     660 cgctagtctc cgtcaagtgc gggacactac cctggagttt gaacggttca ctactggcaa     720
cacccatacc gcctacgtta tctgtcgtca agttgaggcc gctgcgaaaa ccctggggat     780
cgatattacc caggctaccg ttgccgtggt aggcgccacc ggggatatcg gtagtgctgt     840
ttgccggtgg ttagatctga aattgggtgt gggggatctc atttttgactg ctcggaacca     900 ggaacgcctg gataatctgc aagctgaatt gggtcgcggc aagatcctcc ccttagaagc     960
cgccctcccc gaagccgatt tcattgtgtg ggtcgcctct atgccccaag gtgttgttat    1020
tgaccccgcc actctgaaac agccttgtgt tttgatcgat gggggttacc ctaaaaacct    1080
gggctccaaa gtacagggtg aaggcatcta cgtgctcaat ggggcgtcg tggaacactg    1140 ttttgatatc gactggcaaa ttatgagcgc tgccgaaatg gctcgccccg agcgtcaaat    1200
gtttgcctgt tttgccgagg ccatgttgtt ggaattcgaa gggtggcaca ccaacttctc    1260
ctggggtcgc aaccaaatta ccattgaaaa gatggaagcg atcggcgaag cctctgtgcg    1320
tcatggtttt cagcccttgg ctttagccat ctaagagctg ttgacaatta atcatccggc    1380
tcgtataatt ttaaagagga gaaacaaatg aaacagcaat tgaccgacca aagtaaagag    1440
```

```
ctcgatttta agtccgaaac ctataaagac gcctacagtc ggatcaatgc cattgtgatt    1500
gaaggtgaac aggaagcgca tgaaaattac atcactttgg cccaactgct cccggagtcc    1560
cacgacgaac tgatccgctt gtccaagatg gaatcccggc ataagaaagg ctttgaagcg    1620
tgcggccgta acctggcggt aaccccccgac ttacagtttg ccaaagaatt tttcagcggt    1680
```

```
ctcgatttta agtccgaaac ctataaagac gcctacagtc ggatcaatgc cattgtgatt    1500
gaaggtgaac aggaagcgca tgaaaattac atcactttgg cccaactgct cccggagtcc    1560
cacgacgaac tgatccgctt gtccaagatg gaatcccggc ataagaaagg ctttgaagcg    1620
tgcggccgta acctggcggt aaccccgac  ttacagtttg ccaaagaatt tttcagcggt    1680
ttgcatcaaa attttcagac cgccgctgcc gaaggtaaag tggtgacttg cctgctcatt    1740
cagtctctca ttatcgagtg cttcgcgatc gctgcctata acatttacat ccccgttgct    1800
gatgattttg cccgcaaaat cactgaaggc gtagtaaaag aagaatactc ccatttgaat    1860
ttcggcgaag tgtggctgaa agagcatttc gctgaatcca agctgaact  cgaactggcc    1920 aaccgccaaa atttgcccat tgtttggaaa atgctcaacc aggtggaggg gatgcccac    1980 actatggcca tggaaaaaga cgccttggtt gaagatttta tgattcaata cggtgaagcc    2040
ctctccaaca ttggcttctc tacccgggac attatgcgct tgagtgccta cgggttgatc    2100
ggtgcttaag atatcag                                                   2117

<210> SEQ ID NO 134
<211> LENGTH: 1880
<212> TYPE: DNA
<213> ORGANISM: Artificial Sequence
<220> FEATURE:
<223> OTHER INFORMATION: SYNTHESIZED

<400> SEQUENCE: 134
gagatatcga gctgttgaca attaatcatc cggctcgtat aattttaaag aggagaaaca      60
aatgtttggt ttgattgggc actctactag tttcgaagac gccaaacgca aggcttcctt     120
gttgggtttc gatcacatcg ctgatggcga cttggacgtc tggtgtaccg ccccccccca     180
gctggtagaa aatgttgaag tgaagagcgc tattggcatt agcatcgaag gtagttacat     240
tgatagctgt tttgttcccg aaatgttaag ccgcttcaag accgctcgcc ggaaagtgct     300
gaatgctatg gagttggccc agaaaaaagg tatcaatatc accgcttggg gtggtttcac     360
ctccattatc ttcgaaaatt ttaacctgtt gcagcacaaa caaatccgga cacctccct     420 ggaatgggaa cgttttacca ccggtaacac ccacaccgcg tgggtgattt gtcggcaact     480
ggaaatgaat gcccccaaaa ttgggattga cttgaaatcc gccaccgtgg cggtggtggg     540
cgccaccggt gacattggca gcgccgtttg tcgctggctg attaacaaaa ccggcatcgg     600
tgagttgttg ttggtagccc ggcagaagga acccttagat tccttacaaa agaactgga     660 cgggggcacc atcaaaaatc tggacgaagc cctccccgaa gcggacattg tggtgtgggt     720
cgccagtatg cccaagacca tggaaatcga tgcgaataac ctgaaacagc cgtgtttgat     780
gattgatggc ggttacccca aaaacctgga cgagaaattt caaggcaaca acatccatgt     840
tgtaaaaggt ggtatcgtgc gcttcttcaa tgacattggt tggaacatga tggaactggc     900
cgaaatgcag aaccccaaac gggaaatgtt tgcgtgcttc gccgaagcta tgatcttaga     960
gttcgaaaaa tgtcatacca acttctcttg gggtcggaat aatattagtc tggaaaagat    1020
ggagttcatc ggtgccgcca gcgttaaaca cggcttttcc gccatcggct tggacaagca    1080
ccccaaagtg ttagccgtct aagaactgtt gacaattgat catctgacgc gtataatttt    1140
aaagaggaga acaaatgcaa accctggaa  agcaataaaa aaaccaacct cgaaaacagc    1200
attgatctgc ccgatttcac caccgatagt tataaagatg cctatagccg gatcaacgcc    1260
atcgtgatta aggggaaca  ggaagcgcac gataattata tttccttggc tacccctgatc    1320 cccaatgaac tggaagaatt aaccaaactc gccaaaatgg aactgaaaca aagcggggg    1380
```

```
ttcaccgcct gcgggcgcaa tctcggcgtt caagccgata tgatcttcgc caaagaattt      1440
tttagcaaat tgcacggtaa cttttcaggtg gctttgagca atggtaaaac caccacctgt      1500
ctcctgattc aggcgattct gattgaagcg ttcgccattt ccgcttacca cgtttatatt      1560
cgggtggctg atcccttcgc caagaaaatc acccaaggtg tcgtgaaaga cgaatactta      1620
cacttgaatt atgggcaaga atggctcaaa gaaaatctcg ccacctgcaa agatgaactc      1680
atggaagcta acaaagtgaa tttgccctta attaagaaaa tgttggatca agtttccgag      1740
gacgcgagcg tactggccat ggaccgtgaa gaactgatgg aagaattcat gatcgcgtac      1800
caggacaccc tcttggaaat cggcttggat aaccgcgaaa tcgctcggat ggcgatggcg      1860
gctatcgtgt aagatatcag                                                  1880

<210> SEQ ID NO 135
<211> LENGTH: 2061
<212> TYPE: DNA
<213> ORGANISM: Artificial Sequence
<220> FEATURE:
<223> OTHER INFORMATION: SYNTHESIZED

<400> SEQUENCE: 135
agatatcgcg tgcaaggccc agtgatcaat tcattatttt ttcattattt catctccatt        60
gtccctgaaa tcagttgtg tcgcccctct acacagccca gaactatggt aaaggcgcac       120
gaaaaaccgc caggtaaact cttctcaacc cccaaaacgc cctctgttta cccatggaaa       180
aaacgacaat tacaagaaag taaaacttat gtcatctata agcttcgtgt atattaactt       240
cctgttacaa agctttacaa aactctcatt aatcctttag actaagttta gtcagttcca       300
atctgaacga aggaattata accaaatgcc gcagcttgaa gccagccttg aactggactt       360
tcaaagcgag tcctacaaag acgcttacag ccgcatcaac gcgatcgtga ttgaaggcga       420
acaagaggcg ttcgacaact acaatcgcct tgctgagatg ctgcccgacc agcgggatga       480
gcttcacaag ctagccaaga tggaacagcg ccacatgaaa ggctttatgg cctgtggcaa       540
aaatctctcc gtcactcctg acatgggttt tgcccagaaa tttttcgagc gcttgcacga       600
gaacttcaaa gcggcggctg cggaaggcaa ggtcgtcacc tgcctactga ttcaatcgct       660
aatcatcgag tgctttgcga tcgcggctta caacatctac atcccagtgg cggatgcttt       720
tgcccgcaaa atcacggagg gggtcgtgcg cgacgaatac ctgcaccgca acttcggtga       780
agagtggctg aaggcgaatt ttgatgcttc caaagccgaa ctggaagaag ccaatcgtca       840
gaacctgccc ttggtttggc taatgctcaa cgaagtggcc gatgatgctc gcgaactcgg       900
gatggagcgt gagtcgctcg tcgaggactt tatgattgcc tacggtgaag ctctggaaaa       960
catcggcttc acaacgcgcg aaatcatgcg tatgtccgcc tatggccttg cggccgtttg      1020
atccaggaaa tctgaatgtt cggtcttatc ggtcatctca ccagtttgga gcaggcccgc      1080
gacgtttctc gcaggatggg ctacgacgaa tacgccgatc aaggattgga gttttggagt      1140
agcgctcctc ctcaaatcgt tgatgaaatc acagtcacca gtgccacagg caaggtgatt      1200
cacggtcgct acatcgaatc gtgtttcttg ccggaaatgc tggcggcgcg ccgcttcaaa      1260
acagccacgc gcaaagttct caatgccatg tcccatgccc aaaaacacgg catcgacatc      1320
tcggccttgg ggggctttac ctcgattatt ttcgagaatt tcgatttggc cagtttgcgg      1380
caagtgcgcg acactacctt ggagtttgaa cggttcacca ccggcaatac tcacacggcc      1440
tacgtaatct gtagacaggt ggaagccgct gctaaaacgc tgggcatcga cattacccaa      1500
```

| | |
|---|---|
| gcgacagtag cggttgtcgg cgcgactggc gatatcggta gcgctgtctg ccgctggctc | 1560 |
| gacctcaaac tgggtgtcgg tgatttgatc ctgacggcgc gcaatcagga gcgtttggat | 1620 |
| aacctgcagg ctgaactcgg ccggggcaag attctgccct tggaagccgc tctgccggaa | 1680 |
| gctgacttta tcgtgtgggt cgccagtatg cctcagggcg tagtgatcga cccagcaacc | 1740 |
| ctgaagcaac cctgcgtcct aatcgacggg ggctacccca aaaacttggg cagcaaagtc | 1800 |
| caaggtgagg gcatctatgt cctcaatggc ggggtagttg aacattgctt cgacatcgac | 1860 |
| tggcagatca tgtccgctgc agagatggcg cggcccgagc gccagatgtt tgcctgcttt | 1920 |
| gccgaggcga tgctcttgga atttgaaggc tggcatacta acttctcctg ggccgcaac | 1980 |
| caaatcacga tcgagaagat ggaagcgatc ggtgaggcat cggtgcgcca cggcttccaa | 2040 |
| cccttggcat tggcaatttg a | 2061 |

<210> SEQ ID NO 136
<211> LENGTH: 2085
<212> TYPE: DNA
<213> ORGANISM: Artificial Sequence
<220> FEATURE:
<223> OTHER INFORMATION: SYNTHESIZED

<400> SEQUENCE: 136

| | |
|---|---|
| agatatcgcg tgcaaggccc agtgatcaat ttcattattt ttcattattt catctccatt | 60 |
| gtccctgaaa atcagttgtg tcgcccctct acacagccca gaactatggt aaaggcgcac | 120 |
| gaaaaaccgc caggtaaaact cttctcaacc cccaaaacgc cctctgttta cccatggaaa | 180 |
| aaacgacaat tacaagaaag taaaacttat gtcatctata agcttcgtgt atattaactt | 240 |
| cctgttacaa agcttgacaa ttaatcatcc ggctcgtata attttaaaga ggagaaacaa | 300 |
| atgttcggtt taatcggcca tctgactagc ctggagcatg cgcaggccgt agcccaccaa | 360 |
| ttaggttatc ccgaatacgc cgaccaaggt ctggagttct ggtgtatggc gccccccaa | 420 |
| attgtcgatg aaaattactg taaccagcgtc accggcaaaa ccatttacgg caaatacgtg | 480 |
| gaatcttgtt ttctccccga aatgttggcc aaccaacgcg ttaaggctgc tacccggaaa | 540 |
| gttatcaatg cgatggcgca tgctcagaaa cataacattg atattaccgc tttgggcggc | 600 |
| tttagttcca tcatcttcga aaattttgat ttggagaaga tgagccatat tcgtaatatt | 660 |
| gaattggatt ttcggcggtt taccaccggt aacaccccaca ccgcttatat tatttgccaa | 720 |
| cagatcgaac aagcggctcc ccaagtgggc atcgatctgc ggcaagctac cgttgccgtg | 780 |
| tgcggtgcta ccggtgacat tgggtctgcg gtatgtcgtt ggctgaacac ctgcctcgat | 840 |
| gtgcaagatc tgttgttggt ggcccgtaat cgtgatcggc tcttagagtt gcaagccgaa | 900 |
| ctgggccgtg gtaaaatttt agatttgatg gaggccttgc ccttggctga tattgtggta | 960 |
| tgggttgcca gtatgcctaa gggcgtggaa ttgtccatcg aacaattgaa acgcccgagt | 1020 |
| ctgatgattg atggtggtta ccccaaaaac atggccacca agattcaaca tccgcaaatc | 1080 |
| catgttttga acggcggcat tgttgaacac gccttagata ttgattggaa aattatggaa | 1140 |
| attgtgaata tggacgtccc ctcccgccag atgtttgctt gttttgctga agcgatgttg | 1200 |
| ctggaatttg aaggctggca caccaacttt tcctggggtc ggaaccaaat caccgtggaa | 1260 |
| aagatgcaac aaattgggga agtatcccgt aaacacggtt tccaacccctt gttattaaac | 1320 |
| ccccaataag agctgttgac aattgatcat caggatcgta taattttaaa gaggagaaac | 1380 |
| aatgaccacc gccactgcca cccccgtttt agactatcat tccgatcggt acaaagacgc | 1440 |
| ctacagtcgc atcaacgcta ttgtcattga aggcgaacaa gaggctcacg acaactatat | 1500 |

-continued

```
tgacttggcc aaattgttgc cccaacacca agaagaatta acccgtttgg ccaaaatgga    1560
agcccggcat aagaagggtt tcgaagcttg cgggcgcaat ttgtctgtta cccccgatat    1620
ggaattcgcc aaagctttct tcgaaaagct ccgtgcgaac ttccaacgtg ctctggccga    1680
aggtaaaacc gccacctgcc tcctgatcca agccctgatc atcgaatcct tcgccatcgc    1740
cgcgtacaat atctacattc ccatggccga ccccttgcc cgtaaaatta ccgagtccgt    1800
ggtcaaggat gaatactccc atttaaactt cggcgaaatc tggttgaaag aacacttcga    1860
atccgtgaaa ggggaactgg aagaagccaa tcgggctaat ctcccgctgg tctggaagat    1920
gttgaaccag gttgaggccg acgcgaaagt attagggatg gaaaaggacg ccttagtcga    1980
agactttatg attcaatact ctggtgcctt ggaaaacatt ggctttacca cccgcgaaat    2040
catgaagatg tctgtttatg ggctgactgg tgcctaagat atcag                     2085
```